(12) United States Patent
Han et al.

(10) Patent No.: US 12,065,438 B2
(45) Date of Patent: Aug. 20, 2024

(54) SUBSTITUTED TRICYCLIC COMPOUNDS AS INDOLEAMINE 2,3-DIOXYGENASE INHIBITORS

(71) Applicant: Merck Sharp & Dohme LLC, Rahway, NJ (US)

(72) Inventors: Yongxin Han, Needham, MA (US); David Jonathan Bennett, Winchester, MA (US); Indu Bharathan, Somerville, MA (US); Liangqin Guo, Monroe Township, NJ (US); Brett A. Hopkins, Brownsburg, IN (US); Xianhai Huang, Warren, NJ (US); Derun Li, West Roxbury, MA (US); Min Lu, Brookline, MA (US); Alexander Pasternak, Jamaica Plain, MA (US); David L. Sloman, Newton, MA (US); Hongjun Zhang, Boston, MA (US); Hua Zhou, Acton, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 679 days.

(21) Appl. No.: 17/289,062

(22) PCT Filed: Nov. 1, 2019

(86) PCT No.: PCT/US2019/059296
§ 371 (c)(1),
(2) Date: Apr. 27, 2021

(87) PCT Pub. No.: WO2020/096871
PCT Pub. Date: May 14, 2020

(65) Prior Publication Data
US 2021/0403469 A1    Dec. 30, 2021

(51) Int. Cl.
| | | |
|---|---|---|
| *C07D 471/04* | (2006.01) | |
| *C07D 209/94* | (2006.01) | |
| *C07D 215/14* | (2006.01) | |
| *C07D 401/04* | (2006.01) | |
| *C07D 403/04* | (2006.01) | |

(52) U.S. Cl.
CPC ......... *C07D 471/04* (2013.01); *C07D 209/94* (2013.01); *C07D 215/14* (2013.01); *C07D 401/04* (2013.01); *C07D 403/04* (2013.01)

(58) Field of Classification Search
CPC .. C07D 471/04; C07D 209/94; C07D 215/14; C07D 401/04; C07D 403/04
See application file for complete search history.

(56) References Cited

U.S. PATENT DOCUMENTS 8,536,221 B2 * 9/2013 Mortell ............... C07D 403/12
514/464
9,872,853 B2    1/2018 Bastian et al.

FOREIGN PATENT DOCUMENTS

| WO | 2017213919 A1 | 12/2017 | |
|---|---|---|---|
| WO | WO-2017213919 A1 * | 12/2017 | .......... A61K 31/403 |
| WO | 2018039512 A1 | 3/2018 | |
| WO | 2019089412 A1 | 5/2019 | |

OTHER PUBLICATIONS

Chemical Abstract Registry No. 1647814-40-1 (Feb. 15, 2015) (Year: 2015).*
PubChem-CID-50841060, Create Date: Feb. 22, 2011 (Feb. 22, 2011), p. 2, Fig.
PubChem-CID-70907853, Create Date Mar. 21, 2013 (Mar. 21, 2013), p. 2, Fig.

* cited by examiner

*Primary Examiner* — Clinton A Brooks
*Assistant Examiner* — Izabela Schmidt
(74) *Attorney, Agent, or Firm* — Kristi K. Harman; Catherine D. Fitch

(57) ABSTRACT

Disclosed herein are compounds of formula (I) which are inhibitors of an IDO enzyme: Formula (I). Also disclosed herein are uses of the compounds in the potential treatment or prevention of an IDO-associated disease or disorder. Also disclosed herein are compositions comprising these compounds. Further disclosed herein are uses of the compositions in the potential treatment or prevention of an IDO-associated disease or disorder.

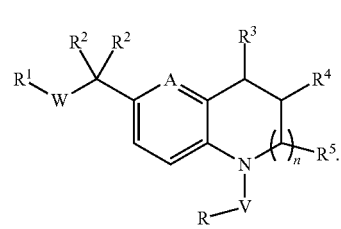

19 Claims, No Drawings

SUBSTITUTED TRICYCLIC COMPOUNDS AS INDOLEAMINE 2,3-DIOXYGENASE INHIBITORS

CROSS REFERENCE TO RELATED APPLICATIONS

The present application is the 371 national phase application of International Application No. PCT/US2019/059296, filed Nov. 1, 2019, which claims the benefit of U.S. Provisional Application No. 62/756,299, filed Nov. 6, 2018, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (IFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with inter-leukin-2 (IL2) was believed to result from IDO released by the tumor cells in response to IFN-γ secretion by the PBLs. This effect was reversed by treatment with 1-methyl-tryptophan (1-MT), a specific IDO inhibitor. It was proposed that IDO activity in tumor cells may serve to impair anti-tumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients, and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1-MT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human DO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1-MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. [1.1.1] Bicyclo compounds disclosed herein are useful in the potential treatment or prevention of IDO-related diseases.

SUMMARY OF THE INVENTION

Disclosed herein are novel compounds of formula (I) which are inhibitors of the IDO enzyme. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein are compounds of formula (I), or a pharmaceutically acceptable salt thereof:

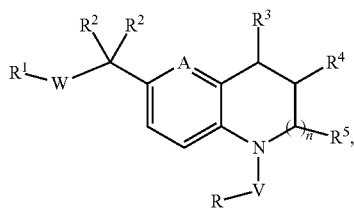

(I)

wherein:
n is 0 or 1;
A is selected from (1) —CH= and (2) —N=;
V is selected from (1) absent and (2) —C(O)—;
W is selected from (1) —C(O)—NH— and (2) —NH—C(O)—;
$R^1$ is selected from (1) aryl and (2) heteroaryl, wherein each of the aryl and heteroaryl is optionally substituted with 1-3 substituents independently selected from:
  (a) halogen, and
  (b) $C_{1-6}$ alkyl, optionally substituted with 1-4 halogens;
each occurrence of $R^2$ is independently selected from: (1) hydrogen and (2) $C_{1-6}$ alkyl;
or alternatively, the two $R^2$ groups together with the carbon to which they are attached form a $C_{3-4}$ cycloalkyl, wherein the $C_{3-4}$ cycloalkyl is optionally substituted with $C_{1-6}$ alkyl;
$R^3$ is hydrogen, n is 1, and $R^4$ and $R^5$ together with the carbons to which they are attached form a $C_{3-4}$ cycloalkyl;
or alternatively, $R^5$ is hydrogen, n is 1, and $R^3$ and $R^4$ together with the carbons to which they are attached form a $C_{3-4}$ cycloalkyl;
or alternatively, $R^5$ is absent, n is 0, and $R^3$ and $R^4$ together with the carbons to which they are attached form a $C_{3-4}$ cycloalkyl;
or alternatively, $R^4$ is selected from (1) hydrogen and (2) $C_{1-6}$ alkyl optionally substituted with 1-3 halogens, n is 1, and $R^3$ and $R^5$ together with the carbons to which they are attached and the carbon to which $R^4$ is attached form a $C_{4-5}$ cycloalkyl;
R is selected from:
  (1) hydrogen,
  (2) aryl,
  (3) $C_{1-6}$ alkyl, optionally substituted with 1-4 substituents halogens,
  (4) $C_{3-6}$ cycloalkyl,
  (5) —O—$C_{1-6}$ alkyl, optionally substituted with phenyl,
  (6) —O—$C_{3-6}$ cycloalkyl,
  (7) —O-heterocyclyl, and
  (8) heteroaryl,
  wherein each of the aryl of (2) and heteroaryl of (8) is optionally substituted with 1-3 substituents independently selected from:
    (a) halogen,
    (b) —OH,
    (c) $C_{1-6}$ alkyl, optionally substituted with 1-4 substituents independently selected from (i) —OH and (ii) halogen,
    (d) —O—$C_{1-6}$ alkyl, optionally substituted with 1-4 substituents independently selected from (i) —OH and (ii) halogen,
    (e) $C_{3-6}$ cycloalkyl,
    (f) —O—$C_{3-6}$ cycloalkyl, and
    (g) —C(O)—O—$C_{1-6}$ alkyl.

In one embodiment of the compound of formula (I), or a pharmaceutically acceptable salt thereof, $R^1$ is phenyl, optionally substituted with 1-3 halogens.

In one embodiment of the compound of formula (I), or a pharmaceutically acceptable salt thereof:
  each occurrence of $R^2$ is independently selected from: (1) hydrogen and (2) $C_{1-4}$ alkyl;
  or alternatively, the two $R^2$ groups together with the carbon to which they are attached form a $C_{3-4}$ cycloalkyl, wherein the $C_{3-4}$ cycloalkyl is optionally substituted with methyl or ethyl.

In one embodiment of the compound of formula (I), or a pharmaceutically acceptable salt thereof:

each occurrence of $R^2$ is independently selected from: (1) hydrogen, (2) methyl, and (3) ethyl;

or alternatively, the two $R^2$ groups together with the carbon to which they are attached form a cyclopropyl or cyclobutyl, wherein each of the cyclopropyl and cyclobutyl is optionally substituted with methyl.

In one embodiment of the compound of formula (I), or a pharmaceutically acceptable salt thereof:

$R^3$ is hydrogen, n is 1, and $R^4$ and $R^5$ together with the carbons to which they are attached form a cyclopropyl or cyclobutyl;

or alternatively, $R^5$ is hydrogen, n is 1, and $R^3$ and $R^4$ together with the carbons to which they are attached form a cyclopropyl or cyclobutyl;

or alternatively, $R^5$ is absent, n is 0, and $R^3$ and $R^4$ together with the carbons to which they are attached form a cyclopropyl or cyclobutyl;

or alternatively, $R^4$ is selected from (1) hydrogen, (2) methyl, and (3) ethyl, n is 1, and $R^3$ and $R^5$ together with the carbons to which they are attached and the carbon to which $R^4$ is attached form a cyclobutyl or cyclopentyl.

In one embodiment of the compound of formula (I), or a pharmaceutically acceptable salt thereof:

$R^3$ is hydrogen, n is 1, and $R^4$ and $R^5$ together with the carbons to which they are attached form a cyclobutyl;

or alternatively, $R^5$ is hydrogen, n is 1, and $R^3$ and $R^4$ together with the carbons to which they are attached form a cyclopropyl;

or alternatively, $R^5$ is absent, n is 0, and $R^3$ and $R^4$ together with the carbons to which they are attached form a cyclopropyl or cyclobutyl;

or alternatively, $R^4$ is selected from (1) hydrogen and (2) methyl, n is 1, and $R^3$ and $R^5$ together with the carbons to which they are attached and the carbon to which $R^4$ is attached form a cyclobutyl.

In one embodiment of the compound of formula (I), or a pharmaceutically acceptable salt thereof:

R is selected from:
(1) hydrogen,
(2) phenyl,
(3) $C_{1-4}$ alkyl, optionally substituted with 1-3 halogens,
(4) $C_{3-4}$ cycloalkyl,
(5) —O—$C_{1-4}$ alkyl, optionally substituted with phenyl,
(6) —O—$C_{3-4}$ cycloalkyl,
(7) —O-heterocyclyl, wherein the heterocyclyl is a 6-membered saturated monocyclic ring containing 1-3 hetero atoms independently selected from O, S, and N, and
(8) a 5- or 6-membered monocyclic heteroaryl containing 1-3 hetero atoms independently selected from O, S, and N, wherein each of the phenyl of (2) and the heteroaryl of (8) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) $C_{3-4}$ cycloalkyl,
(f) —O—$C_{3-4}$ cycloalkyl, and
(g) —C(O)—O—$C_{1-4}$ alkyl.

In one embodiment of the compound of formula (I), or a pharmaceutically acceptable salt thereof:

R is selected from:
(1) hydrogen,
(2) $C_{1-4}$ alkyl, optionally substituted with 1-3 halogens,
(3) $C_{3-4}$ cycloalkyl,
(4) —O—$C_{1-4}$ alkyl, optionally substituted with phenyl,
(5) —O-cyclopropyl,
(6) —O-heterocyclyl, wherein the heterocyclyl is a 6-membered saturated monocyclic ring containing 1-2 hetero atoms independently selected from O, S, and N, and
(7) a heteroaryl selected from (a) pyridinyl and (b) pyrimidinyl, wherein the heteroaryl of (7) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

In one embodiment of the compound of formula (I), or a pharmaceutically acceptable salt thereof:

R is selected from:
(1) hydrogen,
(2) $C_{1-4}$ alkyl, optionally substituted with 1-3 halogens,
(3) cyclopropyl,
(4) —O—$C_{1-4}$ alkyl, optionally substituted with phenyl,
(5) —O-cyclopropyl,
(6) —O-heterocyclyl, wherein the heterocyclyl is tetrahydropyranyl, and
(7) a heteroaryl selected from (a) pyridinyl and (b) pyrimidinyl, wherein the heteroaryl of (7) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

In one embodiment of the compound of formula (I), or a pharmaceutically acceptable salt thereof, the compound is of formula (Ia):

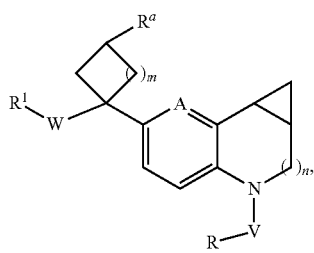
(Ia)

wherein:
m is 0 or 1; n is 0 or 1;
A is selected from (1) —CH= and (2) —N=;
R$^a$ is selected from: (1) hydrogen and (2) C$_{1-4}$ alkyl;
R$^1$ is phenyl, optionally substituted with 1-3 halogens;
V is selected from (1) absent and (2) —C(O)—;
W is selected from (1) —C(O)—NH— and (2) —NH—C(O)—; and
R is selected from:
(1) hydrogen,
(2) C$_{1-4}$ alkyl, optionally substituted with 1-3 halogens,
(3) C$_{3-4}$ cycloalkyl,
(4) —O—C$_{1-4}$ alkyl, optionally substituted with phenyl,
(5) —O-cyclopropyl,
(6) —O-heterocyclyl, wherein the heterocyclyl is a 6-membered saturated monocyclic ring containing 1-2 hetero atoms independently selected from O, S, and N, and
(7) a heteroaryl selected from (a) pyridinyl and (b) pyrimidinyl,
wherein the heteroaryl of (7) is optionally substituted with 1-3 substituents independently selected from:
(a) halogen,
(b) —OH,
(c) C$_{1-4}$ alkyl, optionally substituted with 1-3 substituents independently selected from (i) —OH and (ii) halogen,
(d) —O—C$_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

In one embodiment of the compound of formula (Ia), or a pharmaceutically acceptable salt thereof:
R$^a$ is selected from: (1) hydrogen and (2) methyl;
R$^1$ is phenyl, optionally substituted with a halogen; and
R is selected from:
(1) hydrogen,
(2) C$_{1-4}$ alkyl, optionally substituted with 1-3 halogens,
(3) cyclopropyl,
(4) —O—C$_{1-4}$ alkyl, optionally substituted with phenyl,
(5) —O-cyclopropyl,
(6) —O-heterocyclyl, wherein the heterocyclyl is tetrahydropyranyl, and
(7) a heteroaryl selected from (a) pyridinyl and (b) pyrimidinyl,
wherein heteroaryl of (7) is optionally substituted with 1-3 substituents independently selected from:
(a) halogen,
(b) —OH,
(c) C$_{1-4}$ alkyl, optionally substituted with 1-3 substituents independently selected from (i) —OH and (ii) halogen,
(d) —O—C$_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

In one embodiment of the compound of formula (I), or a pharmaceutically acceptable salt thereof, the compound is of formula (Ib):

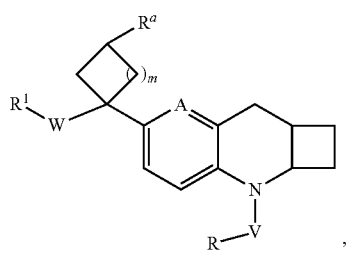
(Ib)

wherein:
m is 0 or 1;
A is selected from (1) —CH= and (2) —N=;
R$^a$ is selected from: (1) hydrogen and (2) C$_{1-4}$ alkyl;
R$^1$ is phenyl, optionally substituted with 1-3 hydrogens;
V is selected from (1) absent and (2) —C(O)—;
W is selected from (1) —C(O)—NH— and (2) —NH—C(O)—; and
R is selected from:
(1) hydrogen,
(2) C$_{1-4}$ alkyl, optionally substituted with 1-3 halogens,
(3) C$_{3-4}$ cycloalkyl,
(4) —O—C$_{1-4}$ alkyl, optionally substituted with phenyl,
(5) —O-cyclopropyl,
(6) —O-heterocyclyl, wherein the heterocyclyl is a 6-membered saturated monocyclic ring containing 1-2 hetero atoms independently selected from O, S, and N, and
(7) a heteroaryl selected from (a) pyridinyl and (b) pyrimidinyl,
wherein the heteroaryl of (7) is optionally substituted with 1-3 substituents independently selected from:
(a) halogen,
(b) —OH,
(c) C$_{1-4}$ alkyl, optionally substituted with 1-3 substituents independently selected from (i) —OH and (ii) halogen,
(d) —O—C$_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

In one embodiment of the compound of formula (Ib), or a pharmaceutically acceptable salt thereof:
A is —CH=;
R$^a$ is hydrogen;
R$^1$ is phenyl, optionally substituted with a halogen; and R is selected from:
(1) —O—$C_{1-4}$ alkyl,
(2) —O-cyclopropyl, and
(3) a heteroaryl selected from (a) pyridinyl and (b) pyrimidinyl, each of which is optionally substituted with a $C_{1-4}$ alkyl.

In one embodiment of the compound of formula (I), or a pharmaceutically acceptable salt thereof, the compound is of formula (Ic):

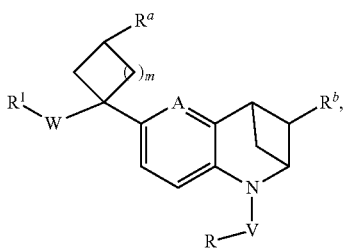

(Ic)

wherein:
m is 0 or 1;
A is selected from (1) —CH= and (2) —N=;
$R^a$ is selected from: (1) hydrogen and (2) $C_{1-4}$ alkyl;
$R^b$ is selected from: (1) hydrogen and (2) $C_{1-4}$ alkyl;
$R^1$ is phenyl, optionally substituted with 1-3 halogens;
V is selected from (1) absent and (2) —C(O)—;
W is selected from (1) —C(O)—NH— and (2) —NH—C(O)—; and
R is selected from:
(1) hydrogen,
(2) $C_{3-4}$ cycloalkyl,
(3) —O—$C_{1-4}$ alkyl, optionally substituted with phenyl,
(4) —O-cyclopropyl,
(5) —O-heterocyclyl, wherein the heterocyclyl is a 6-membered saturated monocyclic ring containing 1-2 hetero atoms independently selected from O, S, and N, and
(6) a heteroaryl selected from (a) pyridinyl and (b) pyrimidinyl,
wherein the heteroaryl of (6) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

In one embodiment of the compound of formula (Ic), or a pharmaceutically acceptable salt thereof:
m is 0;
A is —N=;
$R^a$ is hydrogen;
$R^b$ is selected from: (1) hydrogen and (2) methyl;
$R^1$ is phenyl, optionally substituted with a halogen; and
R is selected from:
(1) hydrogen,
(2) cyclopropyl,
(3) —O—$C_{1-4}$ alkyl, optionally substituted with phenyl,
(4) —O-cyclopropyl, and
(5) a heteroaryl selected from (a) pyridinyl and (b) pyrimidinyl,
wherein the heteroaryl of (5) is optionally substituted with 1-3 substituents independently selected from:
(a) halogen,
(b) —OH, and
(c) $C_{1-4}$ alkyl.

In one embodiment of the compound of formula (I), or a pharmaceutically acceptable salt thereof, the compound of claim 1 is of formula (Id):

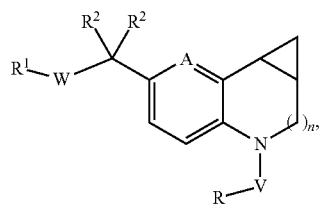

(Id)

wherein:
n is 0 or 1;
A is selected from (1) —CH= and (2) —N=;
$R^1$ is phenyl, optionally substituted with 1-3 halogens;
$R^2$ is selected from: (1) hydrogen and (2) $C_{1-4}$ alkyl;
V is selected from (1) absent and (2) —C(O)—;
W is selected from (1) —C(O)—NH— and (2) —NH—C(O)—; and
R is selected from:
(1) hydrogen,
(2) $C_{1-4}$ alkyl, optionally substituted with 1-3 halogens,
(3) $C_{3-4}$ cycloalkyl,
(4) —O—$C_{1-4}$ alkyl, optionally substituted with phenyl,
(5) —O-cyclopropyl,
(6) —O-heterocyclyl, wherein the heterocyclyl is a 6-membered saturated monocyclic ring containing 1-2 hetero atoms independently selected from O, S, and N, and
(7) a heteroaryl selected from (a) pyridinyl and (b) pyrimidinyl,
wherein the heteroaryl of (7) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

In one embodiment of the compound of formula (Id), or a pharmaceutically acceptable salt thereof:
$R^1$ is phenyl, optionally substituted with a halogen;
$R^2$ is selected from: (1) hydrogen, (2) methyl, and (e) ethyl; and
R is selected from:
(1) hydrogen,
(2) $C_{1-4}$ alkyl, optionally substituted with 1-3 halogens, (3) cyclopropyl,
(4) —O—$C_{1-4}$ alkyl, optionally substituted with phenyl,
(5) —O-cyclopropyl,
(6) —O-heterocyclyl, wherein the heterocyclyl is tetrahydropyranyl, and
(7) a heteroaryl selected from (a) pyridinyl and (b) pyrimidinyl,
wherein heteroaryl of (7) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

In one embodiment, the compound disclosed herein is selected from the group consisting of the compounds exemplified herein, for example, in Examples 1-55, or a pharmaceutically acceptable salt thereof.

Also disclosed herein is a pharmaceutical composition comprising a compound disclosed herein, or a pharmaceutically acceptable salt thereof, and at least one pharmaceutically acceptable carrier.

Also disclosed herein is a method of inhibiting activity of indoleamine 2,3-dioxygenase (IDO) comprising contacting IDO with a compound disclosed herein, or a pharmaceutically acceptable salt thereof.

Also disclosed herein is a method of inhibiting immunosuppression in a patient comprising administering to said patient an effective amount of a compound disclosed herein, or a pharmaceutically acceptable salt thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt thereof.

Also disclosed herein is a method of treating melanoma in a patient comprising administering to said patient an effective amount of a compound disclosed herein, or a pharmaceutically acceptable salt thereof.

Further disclosed herein is a compound disclosed herein, or a pharmaceutically acceptable salt thereof, for use in therapy. In one embodiment, disclosed herein is the use of a compound disclosed herein, or a pharmaceutically acceptable salt thereof, for the preparation of a medicament for use in therapy.

As used herein, "alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$ cycloalkenyl ring. Aryl groups may be optionally substituted with one or more substituents as defined herein. Bonding can be through any of the carbon atoms of any ring. In one embodiment, the aryl is phenyl. In another embodiment, the aryl is naphthyl.

"Carbocyclyl" or "carbocyclic ring" refers to a saturated, partially unsaturated or aromatic ring moiety having only ring carbon atoms. Carbocyclyl moieties include both monocyclic and multicyclic (e.g., bicyclic) ring moieties. Bicyclic carbocyclyl moieties include fused, spirocyclic and bridged bicyclic rings. Examples of carbocyclyl moieties include, but are not limited to, cyclopropyl, cyclobutyl, cyclopentyl, cyclohexyl, cycloheptyl, cyclooctyl, cyclopentenyl, cyclohexenyl, cyclohexadienyl, bicyclo[3.1.0]hexanyl, phenyl, naphthyl and 2,3-dihydro-1H-indenyl. Carbocyclic rings may be optionally substituted with one or more substituents as defined herein. "$C_{5-9}$ carbocycle" refers to a carbocycle group as defined herein having 5 to 9 ring carbon atoms.

In one embodiment, a carbocyclyl is an aryl. In another embodiment, a carbocyclyl is selected from phenyl and naphthyl. In another embodiment, a carbocyclyl is a bicyclic fused ring wherein one 6-membered aromatic ring is fused to a 4- or 5-membered partially unsaturated ring. In one embodiment, the bicyclic fused ring is selected from 2,3-dihydro-1H-indenyl and bicyclo[4.2.0]octa-1,3,5-trienyl.

"Cycloalkyl" refers to a monocyclic saturated carbocyclic ring having the specified number of carbon atoms. For example, $C_{3-6}$ cycloalkyl refers to a cycloalkyl group as defined herein having 3 to 6 carbon atoms. Examples of cycloalkyl include, but are not limited to, cyclopropyl, cyclobutyl, cyclopentyl, and cyclohexyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocyclic and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, a heterocyclyl is a 6-membered saturated monocyclic ring containing 1-3 hetero atoms independently selected from O, S, and N. In one embodiment, a heterocyclyl is a 6-membered saturated monocyclic ring containing 1-2 hetero atoms independently selected from O, S, and N.

In one embodiment, a heterocyclyl is a tetrahydropyranyl.

In one embodiment, a heteroaryl is a 5- or 6-membered monocyclic heteroaryl containing 1-3 hetero atoms independently selected from O, S, and N.

In one embodiment, a heteroaryl is a 5- or 6-membered monocyclic heteroaryl containing 1-2 hetero atoms independently selected from O, S, and N.

In one embodiment, a heteroaryl is selected from pyridinyl and pyrimidinyl.

In one embodiment, a heteroaryl is pyrimidinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound disclosed herein, including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers—Diastereomers—Geometric Isomers—Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound disclosed herein may have one or more asymmetric carbon atom and may occur as a racemic mixture or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound disclosed herein can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are included within the scope of the present invention.

Isotopic Variations

Compounds disclosed herein include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2$H (i.e., Deuterium or "D"), $^3$H, $^{11}$C, $^{13}$C, $^{14}$C, $^{13}$N, $^{15}$N, $^{15}$O, $^{17}$O, $^{18}$O, $^{32}$P, $^{35}$S, $^{18}$F, $^{123}$I, $^{125}$I and $^{36}$Cl. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}$C, $^{18}$F, $^{15}$O and $^{13}$N, may be particularly desirable for PET or SPECT studies.

Isotopically-labeled compounds disclosed herein can generally be prepared by conventional techniques known to those skilled in the art. Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as DO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanoacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein, or a pharmaceutically acceptable salt thereof, may be used in combination with one or more other active agents, or a pharmaceutically acceptable salt thereof, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound disclosed herein and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, or a pharmaceutically acceptable salt thereof, for treating a disease or disorder associated with IDO enzyme activity, wherein the medicament is prepared for administration with another active agent, or a pharmaceutically acceptable salt thereof. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

Experimental

The following examples are intended to be illustrative only and not limiting in any way. Abbreviations used are those conventional in the art or the following.

ACN acetonitrile
BAST bis(2-methoxyethyl)aminosulfur trifluoride
Boc tert-butyloxycarbonyl
° C. degree Celsius
Cbz N-carboxybenzyl
Celite diatomaceous earth used as a filtration medium
(COCl)$_2$ oxalyl chloride
CPBA chloroperoxybenzoic acid
CPME cyclopentyl methyl ether
DAST diethylaminosulfur trifluoride
DCM dichloromethane
DIAD diisopropyl azodicarboxylate
DIEA diisopropylethylamine
DMA dimethylacetamide
DMAP 4-dimethylaminopyridine
DME dimethoxyethane
DMEA dimethylethanolamine
DMF N,N-dimethylformamide
DMP Dess-Martin Periodinane
DMSO dimethylsulfoxide
dppf or DPPF 1,1'-bis(diphenylphosphino)ferrocene
EDC N-(3-Dimethylaminopropyl)-N'-ethylcarbodiimide hydrochloride
EMEM Eagle's minimal essential medium
EtOAc ethyl acetate
EtOH ethanol
Et$_3$N triethylamine
Et$_3$SiH triethylsilane
g gram
h hour(s)
H$_2$O water
HATU (1-[Bis(dimethylamino)methylene]-1H-1,2,3-triazolo[4,5-b]pyridinium 3-oxide hexafluorophosphate)
HOAt 1-hydroxy-7-azabenzotriazole
HPLC high pressure liquid chromatography
Hunig's base N,N-diisopropylethylamine
(Ir[dF(CF$_3$)ppy]$_2$(dtbpy))PF$_6$ [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate
kg kilogram
L liter
LC liquid chromatography
LCMS liquid chromatography and mass spectrometry
LED light-emitting diode
LiHMDS lithium hexamethyldisilamide
MeOH methanol
MeCN acetonitrile
Me-THF methyltetrahydrofuran
MS mass spectrometry
MTBE methyl tert-butyl ether
min minutes
mL or ml milliliter(s)
m/z mass to charge ratio
NB S N-bromosuccinimide
nm nanometer
nM nanomolar
NMP N-methyl-2-pyrrolidone
N normal
N$_2$ nitrogen
NaI sodium iodide
N-XantPhos G4 a fourth generation (G4) Buchwald precatalyst that is similar to the third generation (G3) precatalysts except that the amino group on the biphenyl backbone is methylated; empirical formula C$_{49}$H$_{40}$N$_2$O$_4$P$_2$PdS
Pd(PPh$_3$)$_4$ palladium-tetrakis(triphenylphosphine)

PMB 4-methoxybenzyl ether
RBF rubidium fluoride
RPMI Roswell Park Memorial Institute
RT, rt, or r.t. room temperature
sat. saturated
SFC supercritical fluid chromatography
SPhos G2 2nd generation SPhos Precatalyst, Chloro(2-dicyclohexylphosphino-2',6'-dimethoxy-1,1'-biphenyl)[2-(2'-amino-1,1'-biphenyl)]palladium(II)
TBTU 2-(1H-benzotriazole-1-yl)-1,1,3,3-tetramethylaminium tetrafluoroborate
TEA triethylamine
TFA trifluoroacetic acid
THF tetrahydrofuran
TLC thin layer chromatography
TMSCN trimethylsilyl cyanide
Tos Tosyl or toluenesulfonyl
TPP triphenyl phosphate
TsOH tosylic acid
Xantphos Pd G3 [(4,5-bis(diphenylphosphino)-9,9-dimethylxanthene)-2-(2'-amino-1,1'-biphenyl)]palladium(II) methanesulfonate

INTERMEDIATES

Intermediate A. tert-butyl-2-cyano-6,6a,7-7a-tetrahydro-5H-cyclopropan(c){1,5}napthyridine-5-carboxylate

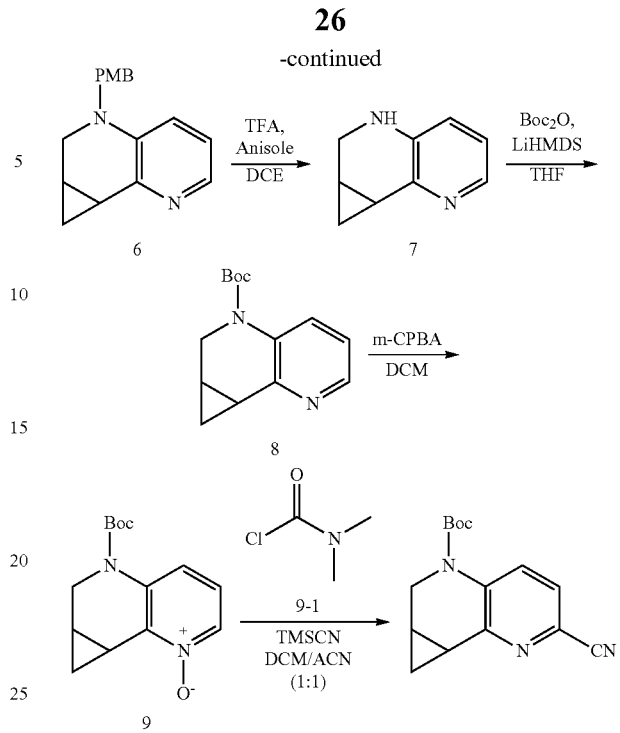

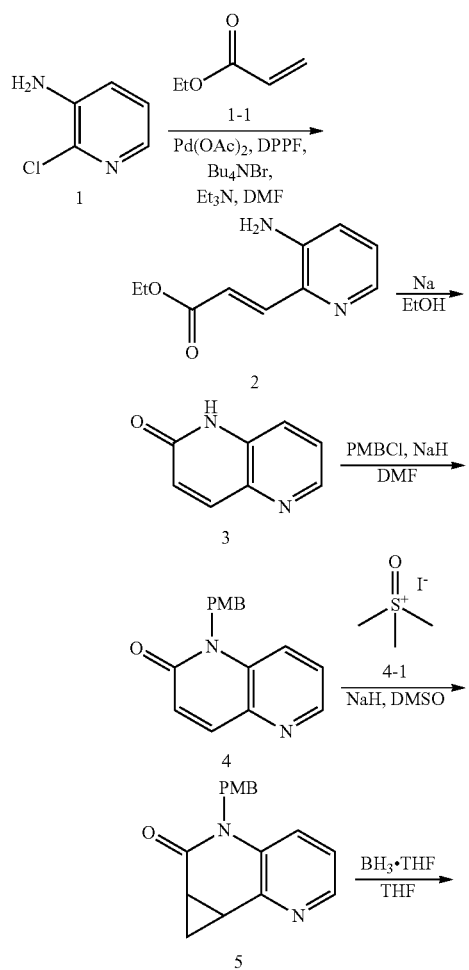

Step 1: ethyl (E)-3-(3-aminopyridin-2-yl)acrylate

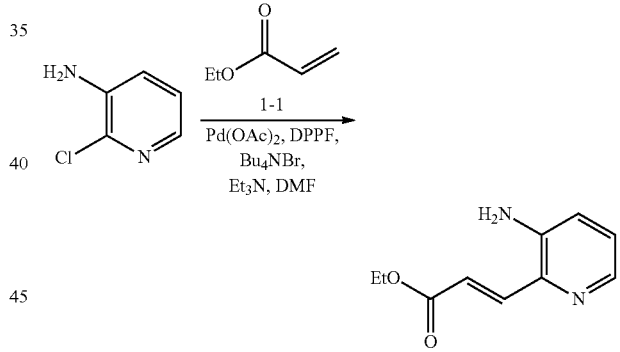

To 2-chloro3-amino pyridine (500.0 g, 3.89 mol, 1.0 eq.), compound 1-1 (1.17 kg, 11.7 mol, 1.27 L, 3.0 eq.), DPPF (215.6 g, 388.9 mmol, 0.1 eq.), Et$_3$N (787.1 g, 7.78 mol, 1.08 L, 2.0 eq.), and Bu$_4$NBr (1.25 kg, 3.89 mol, 1.0 eq.) were added in a 10 L three-necked round bottom flask charged with anhydrous DMF (3.5 L). To this Pd(OAc)$_2$ (87.3 g, 388.9 mmol, 0.1 eq.) was added, and this was purged with N$_2$ thrice. The reaction was allowed to stir at 120° C. for 12 h. The reaction mixture was poured into 10 L water and extracted with ethyl acetate twice (3 L×2). The organic layers were separated, washed with brine, dried over Na$_2$SO$_4$, and filtered. Excess solvent was removed under reduced pressure. The residue was purified on a silica gel column eluted with petroleum ether/ethyl acetate=20/1~1/1 to give the title compound as a solid.

Step 2: 1,5-napthyridin-2(1H)-one

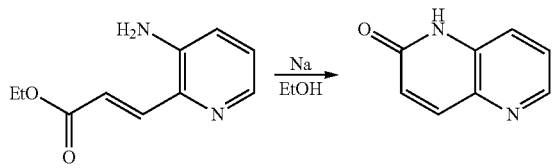

Na (191.4 g, 8.32 mol, 197.3 mL, 4.0 eq.) was added to a solution of EtOH (2.8 L) in a 5 L three neck round bottom flask. The reaction was stirred at 70° C. for 30 min. To this ethyl (E)-3-(3-aminopyridin-2-yl)acrylate (400.0 g, 2.08 mol, 1.0 eq.) was added and stirred at 60° C. for 6 h. The reaction mixture was concentrated to dryness. The crude product was used in the next step without further purification. The title compound was obtained as a solid.

Step 3: 1-(4-methoxybenzyl)-1,5-napthyridin-2(1H)-one

1,5-Napthyridin-2(1H)-one (110.0 g, 752.7 mmol, 1.0 eq.) was added to a solution of DMF (770 mL) in a 3 L three neck round bottom flask to give a suspension. NaH (31.6 g, 790.3 mmol, 60% purity, 1.05 eq.) was added portion-wise at 20° C. for 30 min. The reaction was exothermic. This was allowed to stir at 40° C. for another 1 h.

PMB-Cl (147.3 g, 940.8 mmol, 128.1 mL, 1.25 eq.) was added dropwise at 40° C. This was stirred at 50° C. for another 2 h. The reaction was cooled to 20° C. 110 mL was added dropwise. The residue was poured into water (3 L), and extracted with EtOAc (1 L, 500 mL). The organic layers were combined and washed with brine (500 mL), dried over anhydrous sodium sulfate, and filtered. Excess solvent was removed under reduced pressure. This was purified on a silica gel column using gradient elution with petroleum ether/ethyl acetate=20/1~0/1. The title compound was obtained as a solid. MS ESI calcd. for $C_{16}H_{15}N_2O_2$ [M+H]$^+$ 267.1, found 267.0.

Step 4: 5-(4-methoxybenzyl)-5,6a,7,7a-tetrahydro-6H-cyclopropa(c){1,5}napthyridin-6-one

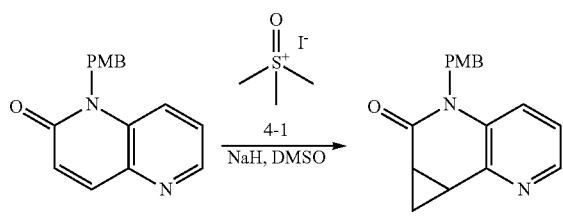

NaH (25.2 g, 630.9 mmol, 60% purity, 2.1 eq.) was added to a solution of DMSO (1.3 L) in a 3-L three neck round bottom flask to give a suspension. Compound 4-1 was added portion wise (132.2 g, 600.8 mmol, 2.0 eq.) at 20° C. and stirred at 60° C. for 1 h. 1-(4-Methoxybenzyl)-1,5-napthyridin-2(1H)-one,5-naphthyridin-2(1H)-one was added drop wise (80.0 g, 300.4 mmol, 1.0 eq.) in DMSO (240 mL)/THF (80 mL) at 60° C. and allowed to stir at 60° C. for 2 h. The reaction mixture was diluted with water (800 mL) at 20° C. The aq. phase was extracted with EtOAc (2×300 mL). The organic layers were combined, washed with brine (500 mL), dried over Na$_2$SO$_4$, filtered, and concentrated to dryness. This was purified on a silica gel column, eluting with petroleum ether/ethyl acetate=20/1~1/1 to give the title compound as a solid. MS ESI calcd. For $C_{17}H_{16}N_2O_2$ [M+H]$^+$ 281.12, found 281.1.

Step 5: 5-(4-methoxybenzyl)-6,6a,7,7a-tetrahydro-5H-cyclopropa{c}{1,5}napthyridine

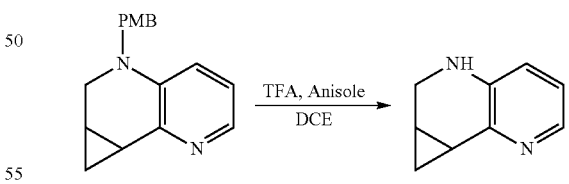

5-(4-Methoxybenzyl)-5,6a,7,7a-tetrahydro-6H-cyclopropa(c){1,5}napthyridin-6-one (50.0 g, 178.4 mmol, 1.0 eq.) was added to a solution of THF (350 mL) in a 2-L three neck round bottom flask. BH$_3$-Me$_2$S (10 M, 35.67 mL, 2.0 eq.) was added dropwise at 20° C. for 30 min and allowed to stir at 60° C. for 1 h and then cooled to 20° C. To this MeOH (59.4 g, 1.85 mol, 75.0 mL, 10.0 eq.) was added at 20° C. and then stirred at 60° C. for 4 h. The reaction mixture was concentrated to dryness and the crude product was used in the next step without further purification. The title compound was obtained as a solid.

MS ESI calcd. for $C_{17}H_{19}N_2O$ [M+H]$^+$ 267.14, found 267.1.

Step 6: 6,6a,7,7a-tetrahydro-5H-cyclopropa(c){1,5}napthyridine 5-(4-methoxybenzyl)-6,6a,7,7a-tetrahydro-5H-cyclopropa{c}{1,5}napthyridine (46.0 g, 172.7 mmol, 1.0 eq.) was added to anisole (186.8 g, 1.73 mol, 187.7 mL, 10.0 eq.) in a solution of DCE (190 mL) in a 500 mL three neck round bottom flask. To this TFA (295.4 g, 2.59 mol, 191.8 mL, 15.0 eq.) was added at 20° C. and stirred at 20° C. for 12 h. The residue was poured into 1N HCl (5 L) and extracted with DCM (1 L). The pH of the aqueous phase was adjusted to 13~14 with NaOH (200 g), and this was extracted with DCM (2 L, 1 L). The organic layers were combined, washed with brine (2 L), dried over anhydrous sodium sulfate, filtered and concentrated to dryness. The crude product was used in the next step without further purification. The title compound was obtained as a solid.

Step 7: tert-butyl 6,6a,7,7a-tetrahydro-5H-cyclopropa(c){1,5}napthyridine-5-carboxylate

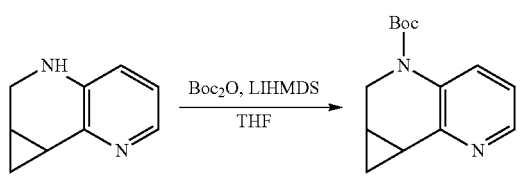 [SMILES: c1cnc2c(c1)NCC1CC21 ; CC(C)(C)OC(=O)N1CC2CC2c2ncccc21 ; "THF"]

6,6a,7,7a-Tetrahydro-5H-cyclopropa(c){1,5}napthyridine (32. g, 218.9 mmol, 1.0 eq.) was added to a solution of THF (270 mL) in a 1-L three neck round bottom flask. To the above solution LiHMDS (1 M, 218.9 mL, 1.0 eq.) was added dropwise at 20° C. for 10 min. To this Boc$_2$O (71.7 g, 328.3 mmol, 75.4 mL, 1.5 eq.) was added dropwise at 20° C. for 10 min, and this was allowed to stir at 40° C. for 2 h. The reaction mixture was poured into 1 L water. This was extracted with EtOAc (2×300 mL). The organic layers were combined, washed with brine (500 mL), dried over anhydrous sodium sulfate, and filtered. Excess solvent was removed under reduced pressure. The residue obtained was purified on a silica gel column using petroleum ether/ethyl acetate=20/1~1/1. The title compound was obtained as an oil.

Step 8: 5-(tert-butoxycarbonyl)-6,6a,7,7a-tetrahydro-5H-cyclopropa(c){1,5}napthyridine-1-oxide

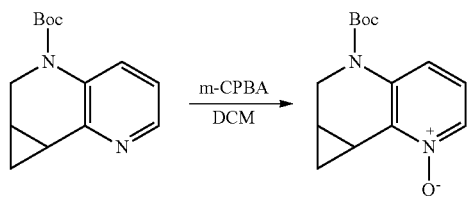

Tert-butyl 6,6a,7,7a-tetrahydro-5H-cyclopropa(c){1,5}napthyridine-5-carboxylate (43.0 g, 174.6 mmol, 1.0 eq.) was added to a solution of DCM (300 mL) in a 1-L three neck round bottom flask. To this m-CPBA (41.4 g, 192.0 mmol, 80% purity, 1.1 eq.) was added at 0° C., and this was allowed to stir at 20° C. for 12 h. The reaction mixture was poured into 10% sodium sulfate solution (600 mL) and extracted with DCM (500 mL, 200 mL). The organic layers were combined, washed with brine (300 mL), dried over anhydrous sodium sulfate, and filtered and concentrated to dryness. The crude product was used in the next step without further purification. The title compound was obtained as a solid.

Step 9: tert-butyl-2-cyano-6,6a,7-7a-tetrahydro-5H-cyclopropan(c){1,5}napthyridine-5-carboxylate

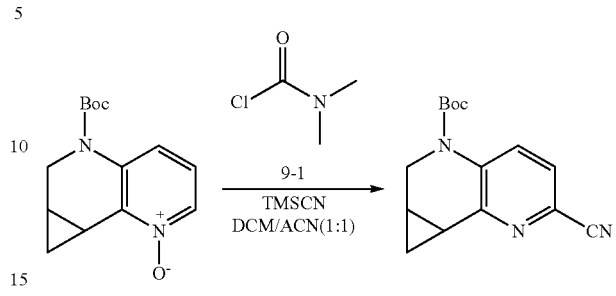

5-(Tert-butoxycarbonyl)-6,6a,7,7a-tetrahydro-5H-cyclopropa(c){1,5}napthyridine-1-oxide (84.0 g, 320.2 mmol, 1.0 eq.) was added to a solution of DCM (420 mL) in a 3-L three neck round bottom flask. To this ACN (420 mL) and TMSCN (47.7 g, 480.4 mmol, 60.1 mL, 1.5 eq.) were added, and this was allowed to stir 20° C. for 10 min. To this compound 9-1 (43.1 g, 400.3 mmol, 36.8 mL, 1.25 eq.) was added, and this was allowed to stir at 20° C. for 12 h. To this 10% potassium carbonate (840 mL) was added, and this was stirred for 20 min. This was poured into water (500 mL). The aqueous phase was extracted with DCM (2×500 mL), washed with brine (500 mL), dried over anhydrous sodium sulfate and filtered and concentrated to dryness. MTBE (300 mL) was added, and this was stirred at 20° C. for 30 min, and the suspension was filtered. The residue was washed with MTBE (100 mL), and the solid obtained was dried under vacuum. The title compound was obtained as a solid.

MS ESI calcd. for $C_{15}H_{18}N_3O_2$ [M+H]$^+$ 272.13, found 272.1.

HNMR: (400 MHz, CDCl$_3$) δ: 7.79 (d, J=8.0 Hz, 1H), 7.46 (d, J=8.4 Hz, 1H), 6.61 (d, J=12.8 Hz, 1H), 2.99 (d, J=12.8 Hz, 1H), 2.33-2.43 (m, 1H), 2.09-2.11 (m, 1H), 1.50 (s, 9H), 1.19-1.24 (m, 1H), 0.96-0.99 (m, 1H).

This was resolved by chiral SFC to give two enantiomers.

Peak 1: MS ESI calcd. for $C_{15}H_{18}N_3O_2$ [M+H]$^+$ 272.1, found 272.1.

$^1$H NMR (499 MHz, DMSO-d$_6$) δ 7.88 (d, J=8.4 Hz, 1H), 7.80 (d, J=8.4 Hz, 1H), 4.45 (d, J=14.2 Hz, 1H), 2.98 (d, J=12.8 Hz, 1H), 2.51 (s, 2H), 2.28 (t, J=8.5 Hz, 1H), 2.17 (q, J=7.9, 6.9 Hz, 1H), 1.44 (s, 9H), 1.28-1.14 (m, 1H), 0.76 (q, J=5.0 Hz, 1H).

Peak 2: MS ESI calcd. for $C_{15}H_{18}N_3O_2$ [M+H]$^+$ 272.1, found 272.1.

$^1$H NMR (499 MHz, DMSO-d$_6$) δ 7.88 (d, J=8.4 Hz, 1H), 7.80 (d, J=8.4 Hz, 1H), 4.45 (d, J=12.9 Hz, 1H), 2.98 (d, J=12.9 Hz, 1H), 2.37-2.24 (m, 1H), 2.24-2.12 (m, 1H), 1.44 (s, 9H), 1.29-1.14 (m, 1H), 0.82-0.70 (m, 1H).

EXAMPLES

Examples 1-2: 4-fluoro-N-(1-(((1aR,7bS)-3-(2-methylpyrimidin-4-yl)-1a,2,3,7b-tetrahydro-1H-cyclopropa[c]quinolin-6-yl)cyclopropyl)benzamide (Isomer 1 and Isomer 2)

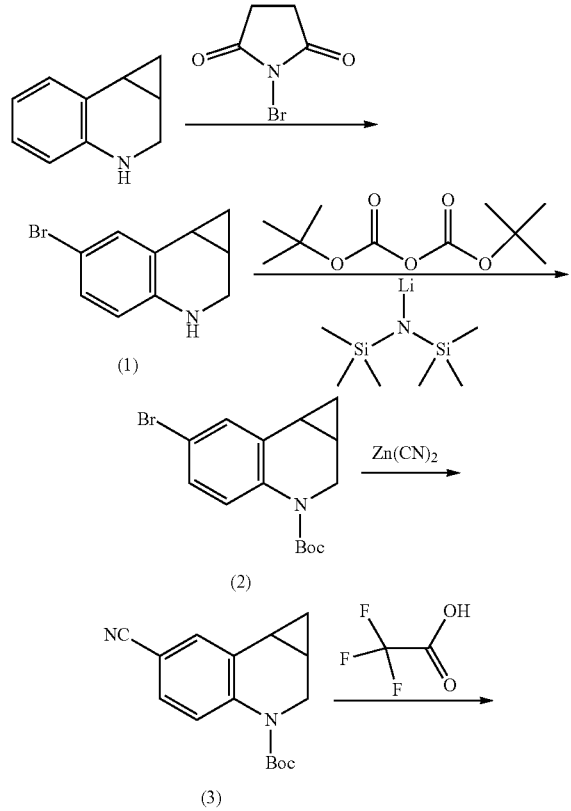

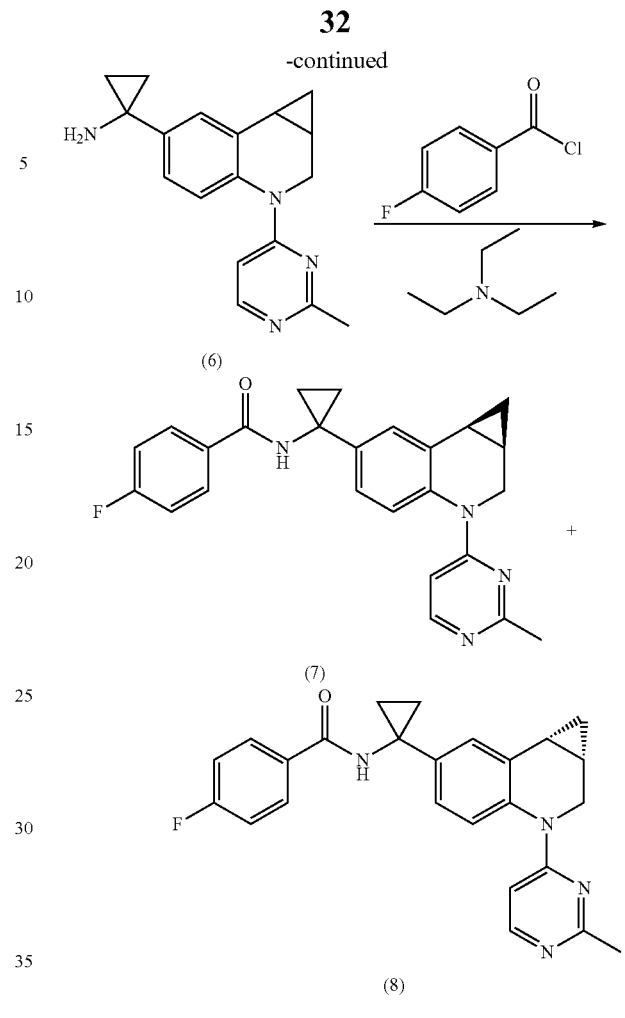

Step 1: 6-bromo-1a,2,3,7b-tetrahydro-1H-cyclopropa[c]quinoline

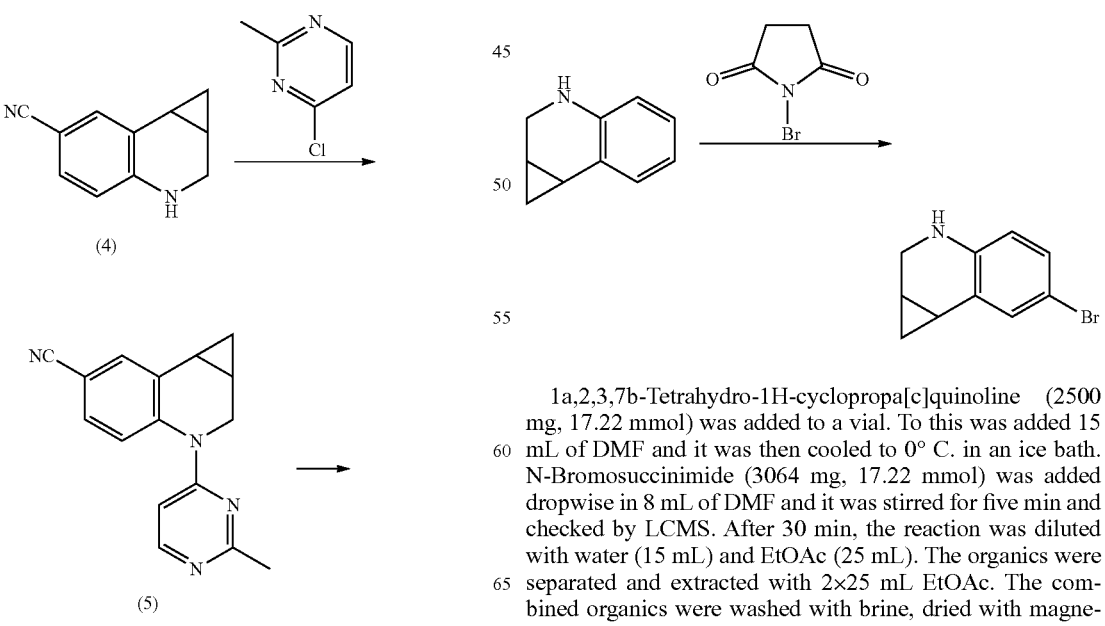

1a,2,3,7b-Tetrahydro-1H-cyclopropa[c]quinoline (2500 mg, 17.22 mmol) was added to a vial. To this was added 15 mL of DMF and it was then cooled to 0° C. in an ice bath. N-Bromosuccinimide (3064 mg, 17.22 mmol) was added dropwise in 8 mL of DMF and it was stirred for five min and checked by LCMS. After 30 min, the reaction was diluted with water (15 mL) and EtOAc (25 mL). The organics were separated and extracted with 2×25 mL EtOAc. The combined organics were washed with brine, dried with magnesium sulfate, filtered, and then evaporated in vacuo to afford a crude material. The crude was purified on a silica gel column (Hexanes: EtOAc 9:1-7:3) to afford the title compound as a an oil. MS (ESI) m/z calc'd for $C_{10}H_{11}BrN$ [M+H]$^+$ 224, found 224.

Step 2: tert-butyl 1a,2-dihydro-1H-cyclopropa[c]quinoline-3(7bH)-carboxylate

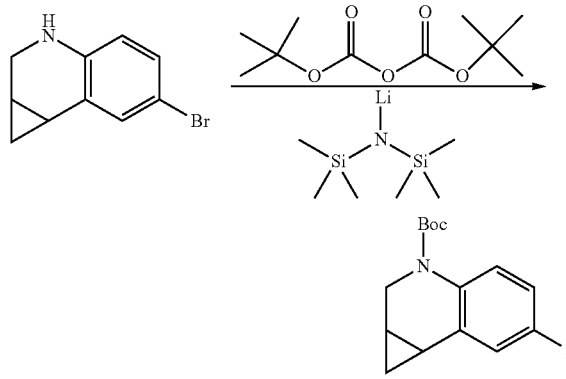

1a,2,3,7b-Tetrahydro-1H-cyclopropa[c]quinoline (1 g, 6.89 mmol) was added to a vial along with triethylamine (2.160 ml, 15.50 mmol). To this 7 mL of dioxane and 2 mL of DMF were added, and the mixture heated at 80° C. overnight with 1.1 eq. of di-tert butyl dicarbonate. The reaction mixture was evaporated in vacuo, and then water was added. The mixture was extracted with ethyl acetate, and the combined organics were dried with magnesium sulfate, filtered, and then evaporated in vacuo to afford a crude material. The crude was purified via column chromatography (hexanes:EtOAc) to afford the title compound as an oil. MS (ESI) m/z calc'd for $C_{15}H_{19}BrNO_2$ [M+H]$^+$ 324.05, found 324.

Step 3: 1a,2,3,7b-tetrahydro-1H-cyclopropa[c]quinoline-6-carbonitrile

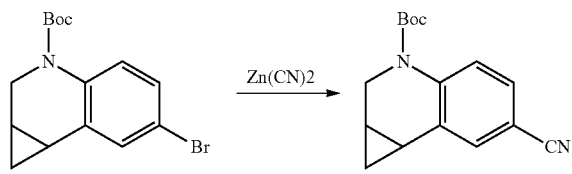

Tert-butyl 6-bromo-1a,2-dihydro-1H-cyclopropa[c]quinoline-3(7bH)-carboxylate (330 mg, 1.018 mmol), Tetrakis(triphenylphosphine)palladium(0) (82 mg, 0.071 mmol) and zinc cyanide (239 mg, 2.036 mmol) were added to a dried 20 ml vial. To this was added 2.0 ml of DMF, and it was heated to 110° C. overnight. The reaction was filtered through a pad of Celite, evaporated in vacuo and purified via column chromatography (hexanes and EtOAc 8:2-6:4). The title compound was isolated as a mixture of the protected boc and deprotected non boc and this mixture was taken forward as is.

Step 4: 1a,2,3,7b-tetrahydro-1H-cyclopropa[c]quinoline-6-carbonitrile, TFA

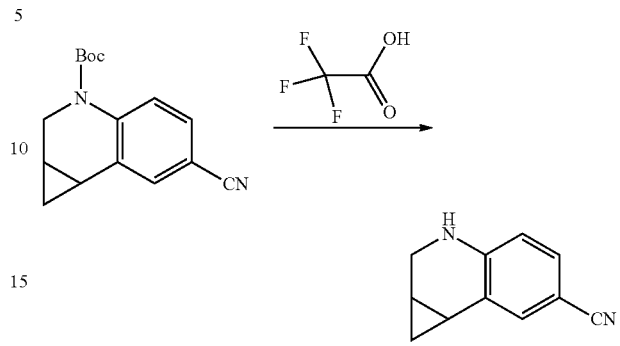

Tert-butyl 6-cyano-1a,2-dihydro-1H-cyclopropa[c]quinoline-3 (7bH)-carboxylate (203 mg, 0.75 mmol) was added to a vial with trifluoroacetic acid (2 ml, 26.0 mmol) along with 2 ml of DCM. The mixture was stirred at RT until complete as determined by LCMS (~1 h). The reaction mixture was evaporated in vacuo and used as is. MS (ESI) m/z calc'd for $C_{11}H_{11}N_2$·TFA [M+H]$^+$ 171.08, found 171.1.

Step 5: 3-(2-methylpyrimidin-4-yl)-1a,2,3,7b-tetrahydro-1H-cyclopropa[c]quinoline-6-carbonitrile

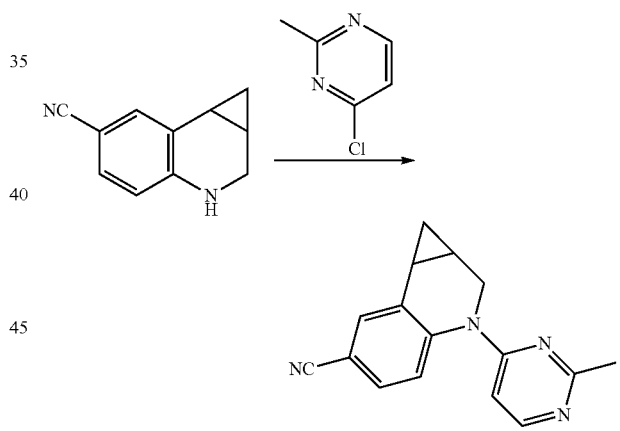

1a,2,3,7b-Tetrahydro-1H-cyclopropa[c]quinoline-6-carbonitrile, TFA (0.200 g, 0.704 mmol), 4-chloro-2-methylpyrimidine (0.181 g, 1.407 mmol), and 4-methylbenzenesulfonic acid (0.133 g, 0.774 mmol) were added to a 20 ml vial and put under nitrogen. To this was added 5 ml of dioxane, and it was stirred at RT. After 1 min, it was purged with argon and then sealed and heated at 100° C. for 15 h. After cooling to RT, the reaction mixture was evaporated in vacuo. Then 5 mL of water was added, and it was made basic with 1 M NaOH and was extracted with 3×15 ml ethyl acetate. The organics were combined, dried with magnesium sulfate, filtered, and evaporated in vacuo. The crude material was purified via column chromatography (hexanes and ethyl acetate) to give the title compound.

MS (ESI) m/z calc'd for $C_{16}H_{15}N_4$ [M+H]$^+$ 263.12, found 263.1.

Step 6: 1-(3-(2-methylpyrimidin-4-yl)-1a,2,3,7b-tetrahydro-1H-cyclopropa[c]quinolin-6-yl)cyclopropanamine

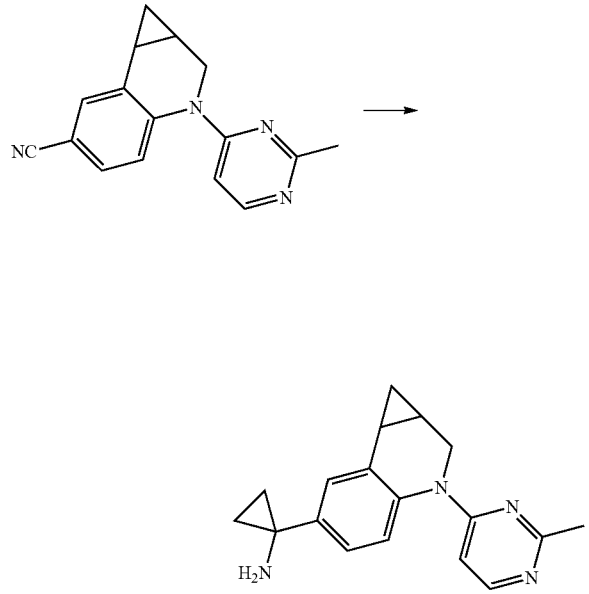

To a solution of 3-(2-methylpyrimidin-4-yl)-1a,2,3,7b-tetrahydro-1H-cyclopropa[c]quinoline-6-carbonitrile (100 mg, 0.381 mmol) in Me-THF (2000 µl) at RT was added titanium (IV) isopropoxide (119 µl, 0.400 mmol), followed by the addition of ethylmagnesium bromide 3.4 M in Me-THF (224 µl, 0.762 mmol). The reaction was slightly extheromic during addition. After the addition, the reaction mixture was kept stirring at RT for 30 min. Then boron trifluoride diethyl etherate (94 µl, 0.762 mmol) was added all at once at RT. The mixture was kept stirring for an additional 30 min. LCMS showed no starting material and mostly product. The mixture was quenched by the slow additional of 1 ml 1N NaOH in water bath, then diluted with water, and extracted with 1:1 EtOAc 10 ml×3. The combined organics were dried over $Na_2SO_4$, and concentrated. The crude material was carried over to the next step. MS (ESI) m/z calc'd for $C_{18}H_{21}N_4$ [M+H]$^+$ 293.17, found 293.3.

Step 7: 4-fluoro-N-(1-((1aR,7bS)-3-(2-methylpyrimidin-4-yl)-1a,2,3,7b-tetrahydro-1H-cyclopropa[c]quinolin-6-yl)cyclopropyl)benzamide

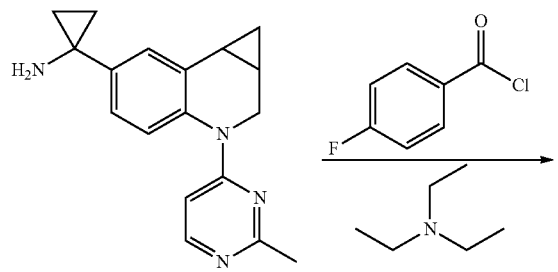

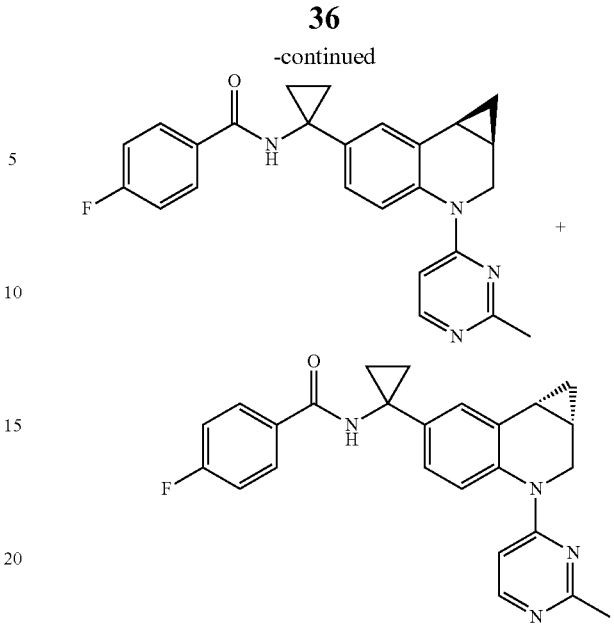

To a flask was added crude 1-(3-(2-methylpyrimidin-4-yl)-1a,2,3,7b-tetrahydro-1H-cyclopropa[c]quinolin-6-yl)cyclopropanamine) (90 mg, 0.308 mmol), and it was dissolved in DCM (2000 µl). To this was added the triethylamine (64.4 µl, 0.462 mmol), followed by 4-fluorobenzoyl chloride (36.4 µl, 0.308 mmol). This was allowed to stir at RT for 5 min, then checked by LCMS. When the reaction was done, it was quenched with 0.25 ml of water, evaporated in vacuo, and then purified on a silica gel column using hexanes: EtOAc (5:5-100% EtOAc) to afford a crude material, which was then further resolved on a chiral SFC column to give the two enantiomers of 4-fluoro-N-(1-((1aR,7bS)-3-(2-methylpyrimidin-4-yl)-1a,2,3,7b-tetrahydro-1H-cyclopropa[c]quinolin-6-yl)cyclopropyl)benzamide using the conditions described below.

Chiral column: Column & dimensions (mm): AS-H, 21×250

Outlet Pressure (bar): 100; UV wavelength (nm): 220; Flow rate (ml/min): 70

Modifier: MeOH w/0.25% DMEA % modifier in $CO_2$: 20; Diluent: 1:1 MeOH/ACN

Example 1 (Isomer 1, 1$^{st}$ eluting): 1H NMR (600 MHz, DMSO-d$_6$) δ 9.16 (s, 1H), 8.02 (d, J=6.1 Hz, 1H), 7.96-7.91 (m, 2H), 7.26 (t, J=8.8 Hz, 2H), 7.21 (d, J=2.2 Hz, 1H), 7.10 (d, J=8.4 Hz, 1H), 6.99-6.96 (m, 2H), 6.59 (d, J=6.1 Hz, 1H), 5.17 (d, J=12.4 Hz, 1H), 2.78 (d, J=12.5 Hz, 1H), 2.38 (s, 3H), 2.00-1.94 (m, 1H), 1.92-1.87 (m, 1H), 1.28-1.18 (m, 4H), 0.89-0.83 (m, 1H), 0.33-0.29 (m, 1H).

MS (ESI) m/z calc'd for $C_{25}H_{24}FN_4O$ [M+H]$^+$ 415.19, found 415.2.

Example 2 (Isomer 2, 2$^{nd}$ eluting): $^1$H NMR (600 MHz, DMSO-d$_6$) δ 9.16 (s, 1H), 8.02 (d, J=6.1 Hz, 1H), 7.96-7.91 (m, 2H), 7.26 (t, J=8.8 Hz, 2H), 7.21 (d, J=2.2 Hz, 1H), 7.10 (d, J=8.4 Hz, 1H), 6.99-6.96 (m, 2H), 6.59 (d, J=6.1 Hz, 1H), 5.17 (d, J=12.4 Hz, 1H), 2.78 (d, J=12.5 Hz, 1H), 2.38 (s, 3H), 2.00-1.94 (m, 1H), 1.92-1.87 (m, 1H), 1.28-1.18 (m, 4H), 0.89-0.83 (m, 1H), 0.33-0.29 (m, 1H).

MS (ESI) m/z calc'd for $C_{25}H_{24}FN_4O$ [M+H]$^+$ 415.19, found 415.2.

Examples 3-4: 1-(3-(cyclopropanecarbonyl)-1a,2,3,7b-tetrahydro-1H-cyclopropa[c]quinolin-6-yl)-N-(4-fluorophenyl)cyclobutanecarboxamide (Isomers 1 and 2)

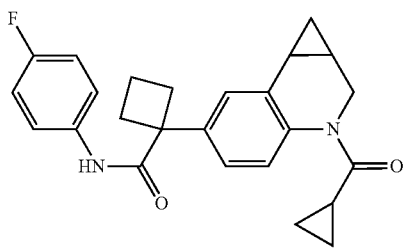 [SMILES: O=C(C1CC1)N1CC2CC2c2cc(C3(C(=O)Nc4ccc(F)cc4)CCC3)ccc21]

Step 1: cyclopropyl(1a,2-dihydro-1H-cyclopropa[c]quinolin-3(7bH)-yl)methanone

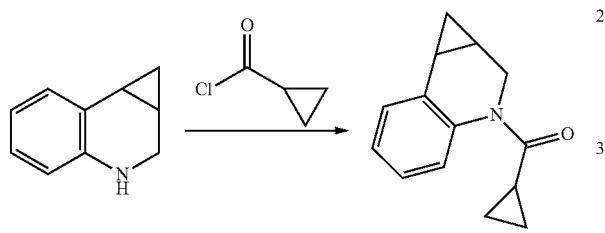

1a,2,3,7b-Tetrahydro-1H-cyclopropa[c]quinoline (0.30 g, 2.066 mmol) was added to a vial along with potassium carbonate (0.857 g, 6.20 mmol). To this was added 4 mL of DCM, and it was then cooled to 0° C. in an ice bath. Cyclopropanecarbonyl chloride (0.376 ml, 4.13 mmol) was added dropwise to this cooled mixture, and it was allowed to slowly warm to RT while stirring overnight for 15 h. When done, the mixture was filtered through a pad of Celite and then evaporated in vacuo to afford a crude material which was then purified via column chromatography (Hexanes: EtOAc 9:1-8:2) to afford the title compound as an oil. MS (ESI) m/z calc'd for $C_{14}H_{16}NO$ [M+H]$^+$ 214.12, found 214.2.

Step 2: (6-bromo-1a,2-dihydro-1H-cyclopropa[c]quinolin-3(7bH)-yl)(cyclopropyl)methanone

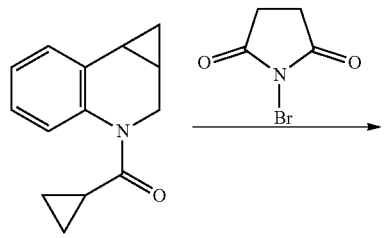

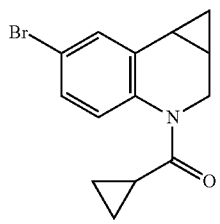

Cyclopropyl(1a,2-dihydro-1H-cyclopropa[c]quinolin-3(7bH)-yl)methanone (275 mg, 1.289 mmol) was added to a vial. To this was added 1.5 mL of DMF. N-bromosuccinimide (367 mg, 2.063 mmol) was added all at once while under nitrogen, and then the vial was sealed under nitrogen and heated at 55° C. for 14 h. When reaction completion was confirmed by LCMS, it was diluted with water (5 mL) and EtOAc (5 mL). The organics were separated, and it was extracted with 2×20 mL EtOAc. The combined organics were washed with brine, dried with magnesium sulfate, filtered, and then evaporated in vacuo to afford a crude material. The crude material was then purified via column chromatography (hexanes and ethyl acetate 9:1-8:2) to afford the title compound as an oil. MS (ESI) m/z calc'd for $C_{14}H_{15}BrNO$ [M+H]$^+$ 292.03, found 292.2.

Step 3: 1-(3-(cyclopropanecarbonyl)-1a,2,3,7b-tetrahydro-1H-cyclopropa[c]quinolin-6-yl)cyclobutanecarbonitrile

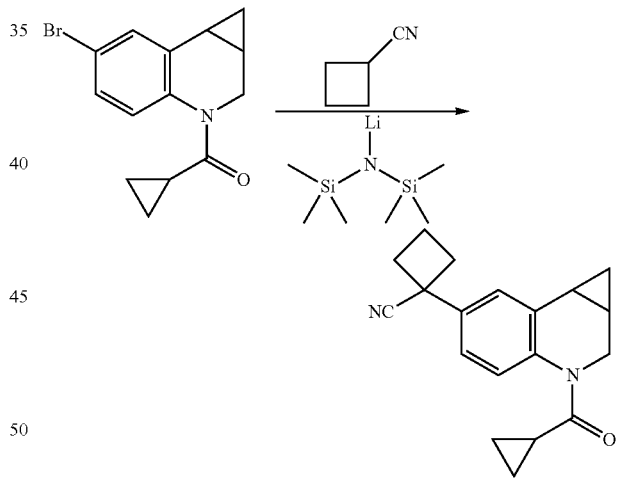

An oven dried microwave vial equipped with a stir bar was charged with NXantPhos G4 (5.76 mg, 6.16 μmol), and this flask was placed under a stream of nitrogen. To this was added the(6-bromo-1a,2-dihydro-1H-cyclopropa[c]quinolin-3(7bH)-yl)(cyclopropyl)methanone (12 mg, 0.041 mmol) in 0.25 mL of CPME. Cyclobutanecarbonitrile (4.61 μl, 0.049 mmol) was then added, followed by a dropwise addition of LiHMDS 1M (THF) (53.4 μl, 0.053 mmol). This was allowed to stir at RT for 1 h and then was checked by LCMS. When done by LCMS it was evaporated in vacuo and purified via column chromatography (hexanes and ethyl acetate (9:1-7:3) to afford the title compound as an oil. MS (ESI) m/z calc'd for $C_{19}H_{21}N_2O$ [M+H]$^+$ 293.16, found 293.2.

Step 4: 1-(3-(cyclopropanecarbonyl)-1a,2,3,7b-tetrahydro-1H-cyclopropa[c]quinolin-6-yl)cyclobutanecarbonitrile

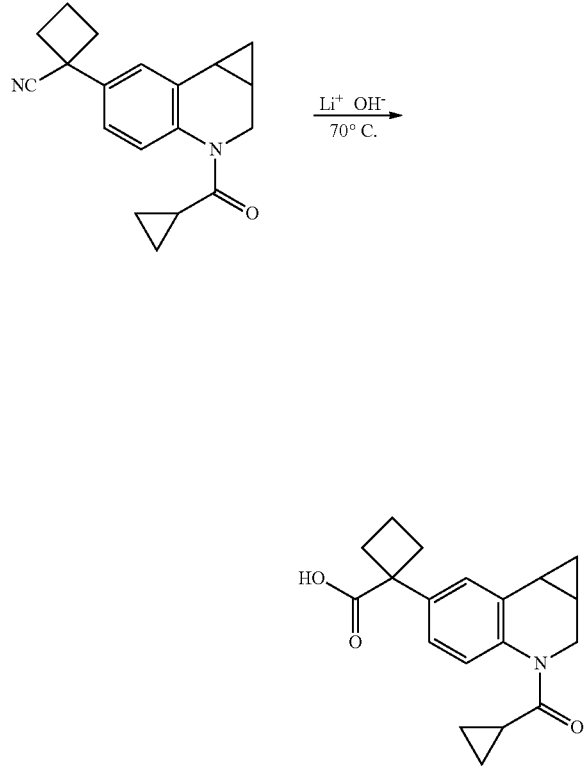

Lithium hydroxide (38.3 mg, 1.601 mmol) was added to a flask containing the 1-(3-(cyclopropanecarbonyl)-1a,2,3,7b-tetrahydro-1H-cyclopropa[c]quinolin-6-yl)cyclobutanecarbonitrile (78 mg, 0.267 mmol). To this was added 1 mL of water and 1 mL of ethanol. This was then heated in a sealed flask under argon at 65° C. for 72 h. When done, it was evaporated in vacuo and then added to a funnel with ethyl acetate and 1 M HCl (until pH ~3). The aqueous layer was extracted with 2×10 mL EtOAc and the organics were combined, filtered, and evaporated in vacuo to afford a crude solid which was used as is for the next step. MS (ESI) m/z calc'd for $C_{19}H_{22}NO_3$ [M+H]$^+$ 312.15, found 312.3.

Step 5: 1-(3-(cyclopropanecarbonyl)-1a,2,3,7b-tetrahydro-1H-cyclopropa[c]quinolin-6-yl)-N-(4-fluorophenyl)cyclobutanecarboxamide

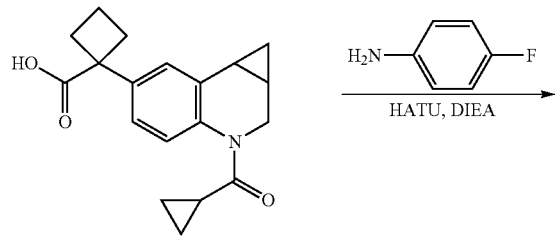

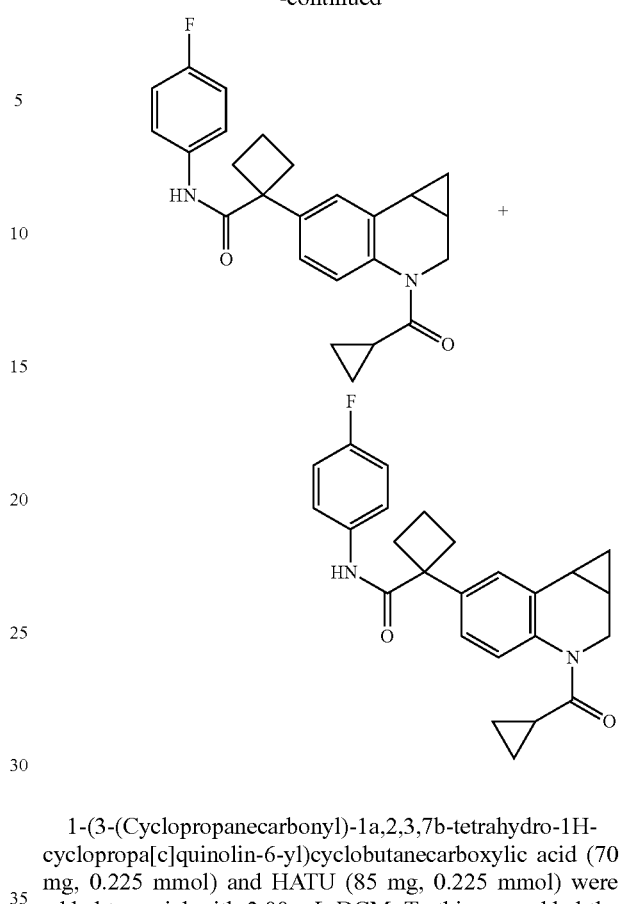

1-(3-(Cyclopropanecarbonyl)-1a,2,3,7b-tetrahydro-1H-cyclopropa[c]quinolin-6-yl)cyclobutanecarboxylic acid (70 mg, 0.225 mmol) and HATU (85 mg, 0.225 mmol) were added to a vial with 2.00 mL DCM. To this was added the 4-fluoroaniline (32.0 μl, 0.337 mmol) followed by the DIPEA (118 μl, 0.674 mmol). It was allowed to stir for 24 h. Excess solvent was evaporated in vacuo and purified via automated column chromatography with hexanes and ethyl acetate to afford a solid. Chiral resolution of this solid on SFC gave two separate enantiomers.

Column & dimensions (mm): OJ-H, 21×250; Outlet Pressure (bar): 100

UV wavelength (nm): 220; Flow rate (ml/min): 70; Modifier: MeOH w/0.25% DMEA

% modifier in $CO_2$: 20; Diluent: MeOH/ACN 1:1 plus heat and filter

Example 3 (Isomer 1, first eluting): MS (ESI) m/z calc'd for $C_{25}H_{26}FN_2O_2$ [M+H]$^+$ 405.19. found 405.2.

$^1$H NMR (600 MHz, DMSO-d$_6$) δ 9.47 (s, 1H), 7.66-7.58 (m, 2H), 7.47 (s, 1H), 7.23-7.15 (m, 2H), 7.10-7.03 (m, 2H), 4.75 (d, J=11.9 Hz, 1H), 2.82-2.73 (m, 2H), 2.68-2.54 (m, 1H), 2.46-2.37 (m, 2H), 2.05-2.00 (m, 1H), 1.91-1.70 (m, 4H), 0.99-0.93 (m, 1H), 0.90-0.68 (m, 3H), 0.65-0.55 (m, 1H), 0.52-0.45 (m, 1H).

Example 4 (Isomer 2, second eluting): MS (ESI) m/z calc'd for $C_{25}H_{26}FN_2O_2$ [M+H]$^+$ 405.19. found 405.2.

$^1$H NMR (600 MHz, DMSO-d$_6$) δ 9.47 (s, 1H), 7.66-7.58 (m, 2H), 7.47 (s, 1H), 7.23-7.15 (m, 2H), 7.10-7.03 (m, 2H), 4.75 (d, J=11.9 Hz, 1H), 2.82-2.73 (m, 2H), 2.68-2.54 (m, 1H), 2.46-2.37 (m, 2H), 2.05-2.00 (m, 1H), 1.91-1.70 (m, 4H), 0.99-0.93 (m, 1H), 0.90-0.68 (m, 3H), 0.65-0.55 (m, 1H), 0.52-0.45 (m, 1H).

Example 5: 4-fluoro-N-(1-(3-(2-methylpyrimidin-4-yl)-1,2,2a,3,8,8a-hexahydrocyclobuta[b]quinolin-6-yl)cyclopropyl)benzamide

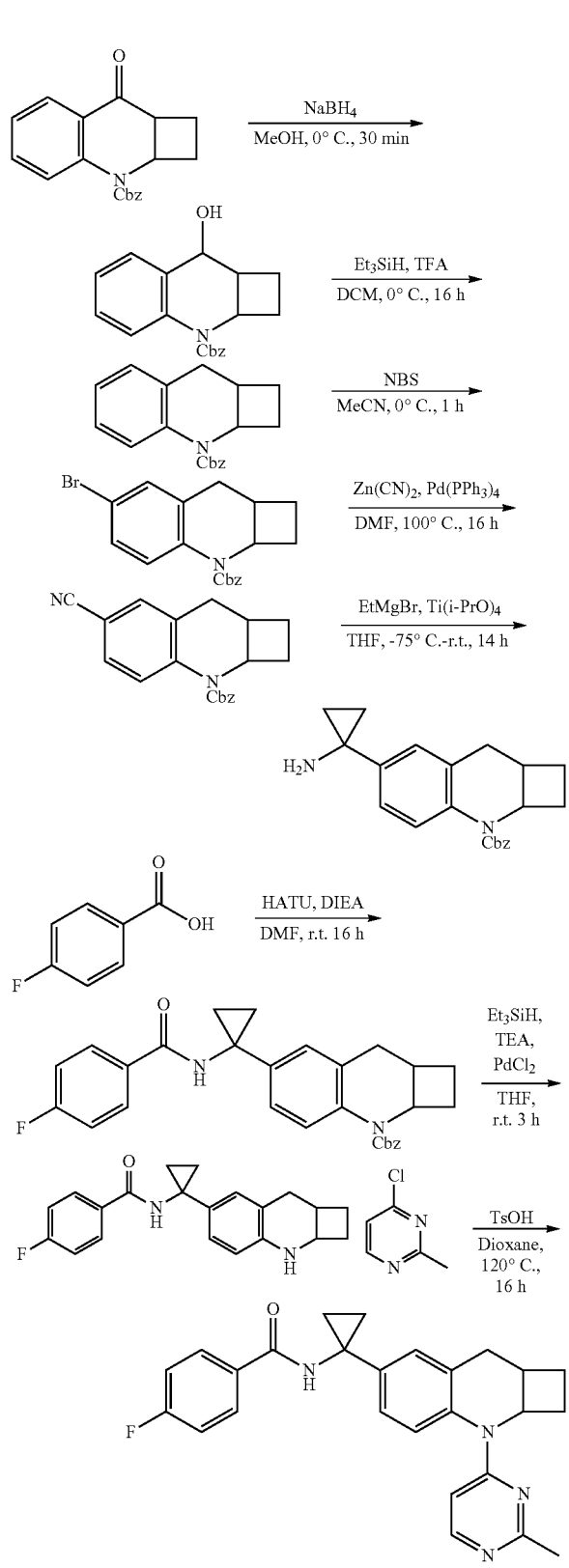

Step 1: benzyl 8-hydroxy-2,2a,8,8a-tetrahydrocyclobuta[b]quinoline-3(1H)-carboxylate

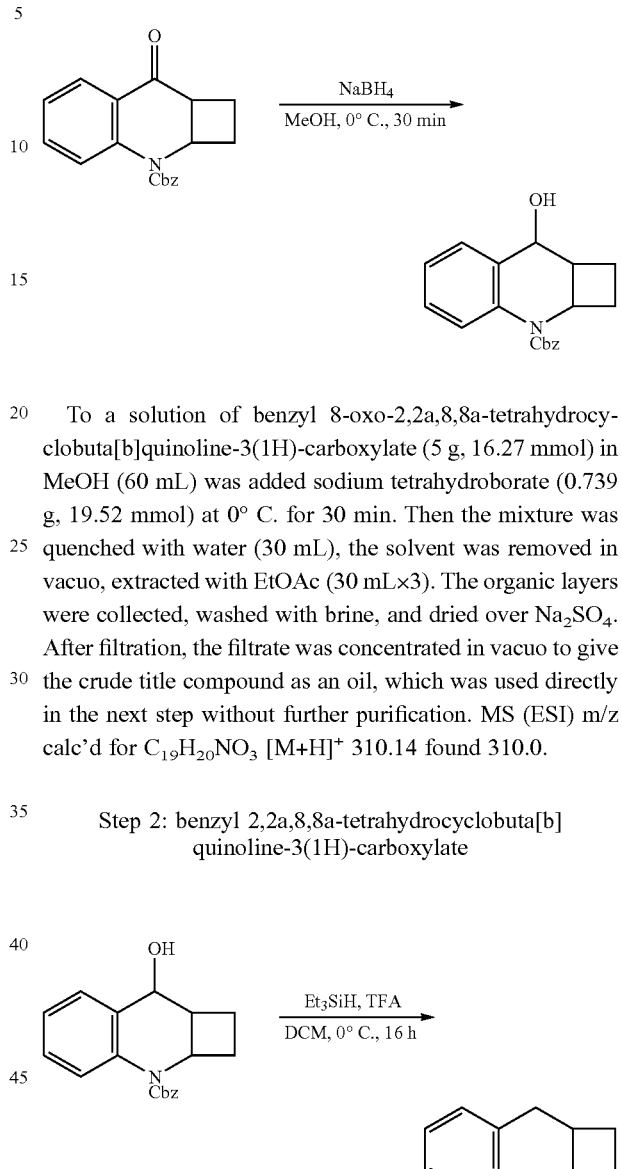

To a solution of benzyl 8-oxo-2,2a,8,8a-tetrahydrocyclobuta[b]quinoline-3(1H)-carboxylate (5 g, 16.27 mmol) in MeOH (60 mL) was added sodium tetrahydroborate (0.739 g, 19.52 mmol) at 0° C. for 30 min. Then the mixture was quenched with water (30 mL), the solvent was removed in vacuo, extracted with EtOAc (30 mL×3). The organic layers were collected, washed with brine, and dried over $Na_2SO_4$. After filtration, the filtrate was concentrated in vacuo to give the crude title compound as an oil, which was used directly in the next step without further purification. MS (ESI) m/z calc'd for $C_{19}H_{20}NO_3$ [M+H]$^+$ 310.14 found 310.0.

Step 2: benzyl 2,2a,8,8a-tetrahydrocyclobuta[b]quinoline-3(1H)-carboxylate

To a solution of benzyl 8-hydroxy-2,2a,8,8a-tetrahydrocyclobuta[b]quinoline-3(1H)-carboxylate (4.95 g, 16.00 mmol) in DCM (50 mL) were added triethylsilane (18 mL, 113 mmol) and TFA (24 mL, 322 mmol) at 0° C. for 16 h. Then the mixture was concentrated in vacuo. Water (30 mL) was added and extracted with DCM (60 mL×3). The combined organic layer was dried over $Na_2SO_4$ and concentrated in vacuo. The residue was purified by flash silica gel chromatography (ISCO®; Agela® Flash Column Silica-CS (20 g), Eluent of 0-30% Ethyl acetate/Petroleum ether gradient @ 30 mL/min) to give the title compound as an oil. MS (ESI) m/z calc'd for $C_{19}H_{20}NO_2$ [M+H]$^+$ 294.14, found 294.1.

Step 3: benzyl 6-bromo-2,2a,8,8a-tetrahydrocyclobuta[b]quinoline-3(1H)-carboxylate

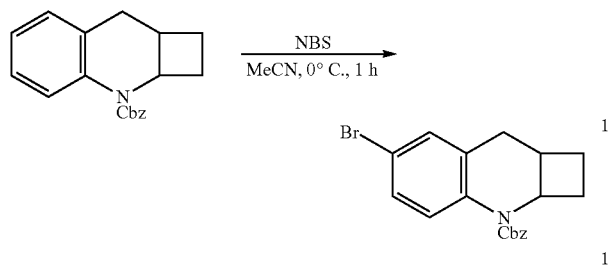

To a solution of benzyl 2,2a,8,8a-tetrahydrocyclobuta[b]quinoline-3(1H)-carboxylate (4.7 g, 16.02 mmol) in ACN (50 mL) was added 1-bromopyrrolidine-2,5-dione (2.71 g, 15.22 mmol) and stirred at 0° C. for 1 h. Then the mixture was concentrated in vacuo, diluted with water (80 mL), and extracted with EtOAc (100 mL×3). The combined organic layer was dried over Na$_2$SO$_4$ and concentrated in vacuo. The residue was purified by flash silica gel chromatography (ISCO®; Agela® Flash Column Silica-CS (20 g), Eluent of 0-10% Ethyl acetate/Petroleum ether gradient @ 45 mL/min) to give benzyl 6-bromo-2,2a,8,8a-tetrahydrocyclobuta[b]quinoline-3(1H)-carboxylate as an oil.

MS (ESI) m/z calc'd for C$_{19}$H$_{19}$BrNO$_2$ [M+H]$^+$ 371.05, found 371.0.

Step 4: benzyl 6-cyano-2,2a,8,8a-tetrahydrocyclobuta[b]quinoline-3(1H)-carboxylate

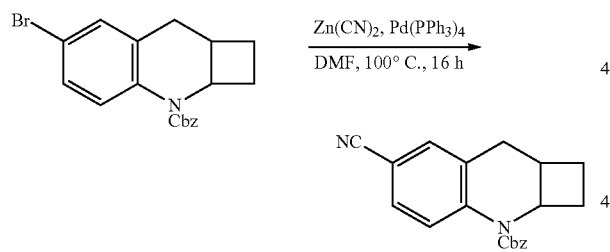

To a stirred solution of benzyl 6-bromo-2,2a,8,8a-tetrahydrocyclobuta[b]quinoline-3(1H)-carboxylate (5 g, 13.43 mmol) in DMF (20 mL) was added Zn(CN)$_2$ (4.73 g, 40.3 mmol) and Pd(PPh$_3$)$_4$ (1.552 g, 1.343 mmol) at RT. After the addition was finished, the reaction was stirred at 100° C. under N$_2$ atmosphere. The reaction was monitored by LC-MS, after stirring at 100° C. for 16 h, the reaction was finished. After cooling to RT, the reaction mixture was diluted with water (150 mL), and extracted with EtOAc (80 mL×3). The organic layers were collected, washed with brine (30 mL), and dried over Na$_2$SO$_4$. After filtration, the filtrate was concentrated in vacuo. The residue was purified by flash silica gel chromatography (ISCO®; Agela® Flash Column Silica-CS (20 g) Eluent of 0-50% Ethyl acetate/Petroleum ether gradient @ 45 mL/min) to give the title compound as a solid.

MS (ESI) m/z calc'd for C$_{20}$H$_{19}$N$_2$O$_2$ [M+H]$^+$ 319.14, found 319.2.

Step 5: benzyl 6-(1-aminocyclopropyl)-2,2a,8,8a-tetrahydrocyclobuta[b]quinoline-3(1H)-carboxylate

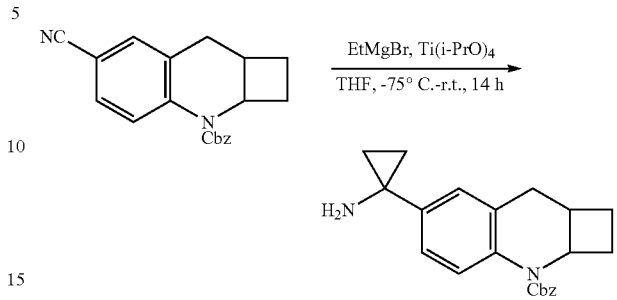

To a solution of benzyl 6-cyano-2,2a,8,8a-tetrahydrocyclobuta[b]quinoline-3(1H)-carboxylate (1 g, 3.14 mmol) in THF (10 mL) was added Ti(i-PrO)$_4$ (0.982 g, 3.46 mmol) at −75° C. dropwise over 5 min. Ethyl magnesium bromide (2.3 mL, 6.90 mmol) (3 M) was added dropwise with stirring under N$_2$. After the addition was complete, the reaction mixture was warmed to RT slowly and stirred for 14 h. The mixture was diluted with water (20 mL), and extracted with EtOAc (20 mL×3). The organic layers were collected, washed with brine (10 mL), and dried over Na$_2$SO$_4$. After filtration, the filtrate was concentrated in vacuo. The residue was purified by flash silica gel chromatography (ISCO®; Agela® Flash Column Silica-CS (4 g) Eluent of 0-30% Ethyl acetate/Petroleum ether gradient @ 30 mL/min) to give the title compound as a solid. MS (ESI) m/z calc'd for C$_{22}$H$_{25}$N$_2$O$_2$ [M+H]$^+$ 349.18, found 349.0.

Step 6: benzyl 6-(1-(4-fluorobenzamido)cyclopropyl)-2,2a,8,8a-tetrahydrocyclobuta[b]quinoline-3(1H)-carboxylate

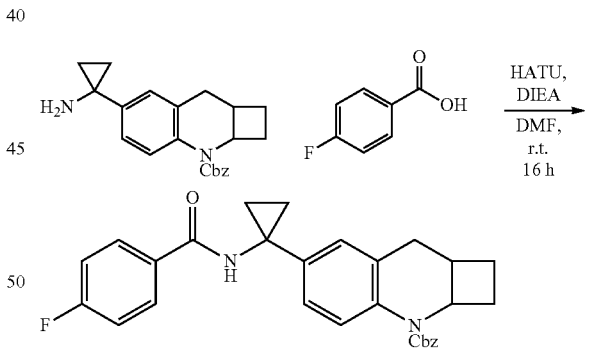

To a stirred solution of benzyl 6-(1-aminocyclopropyl)-2,2a,8,8a-tetrahydrocyclobuta[b] quinoline-3(1H)-carboxylate (240 mg, 0.689 mmol) in DMF (5 mL) were added N-ethyl-N-isopropylpropan-2-amine (0.34 mL, 2.057 mmol), HATU (340 mg, 0.895 mmol), and 4-fluorobenzoic acid (106 mg, 0.758 mmol) at RT while stirring for 16 h. The mixture was diluted with water (50 mL), and extracted with EtOAc (30 mL×2). The organic layers were collected, washed with brine (20 mL), and dried over Na$_2$SO$_4$. After filtration, the filtrate was concentrated in vacuo. The residue was purified by prep-TLC (Petroleum ether/EtOAc=3/1) to give the title compound as a solid. MS (ESI) m/z calc'd for C$_{29}$H$_{28}$FN$_2$O$_3$ [M+H]$^+$ 471.20, found 471.3.

Step 7: 4-fluoro-N-(1-(1,2,2a,3,8,8a-hexahydrocyclobuta[b]quinolin-6-yl)cyclopropyl)benzamide

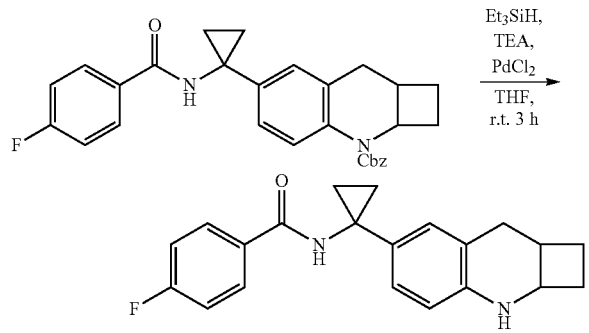

To a stirred solution of benzyl 6-(1-(4-fluorobenzamido)cyclopropyl)-2,2a,8,8a-tetrahydrocyclobuta[b]quinoline-3(1H)-carboxylate (200 mg, 0.425 mmol) in THF (5 mL) were added palladium(II) chloride (8 mg, 0.045 mmol), TEA (0.4 mL, 2.87 mmol), and triethylsilane (200 mg, 1.720 mmol) at RT while stirring for 3 h. The mixture was diluted with water (30 mL), and extracted with EtOAc (20 mL×3). The organic layers were collected, washed with brine (10 mL), and dried over Na$_2$SO$_4$. After filtration, the filtrate was concentrated in vacuo. The residue was purified by prep-TLC (Petroleum ether/EtOAc=2/1) to give the title compound as a solid.

MS (ESI) m/z calc'd for C$_{21}$H$_{22}$FN$_2$O [M+H]$^+$ 336.16, found 336.9.

Step 8: 4-fluoro-N-(1-(3-(2-methylpyrimidin-4-yl)-1,2,2a,3,8,8a-hexahydrocyclobuta[b]quinolin-6-yl)cyclopropyl)benzamide

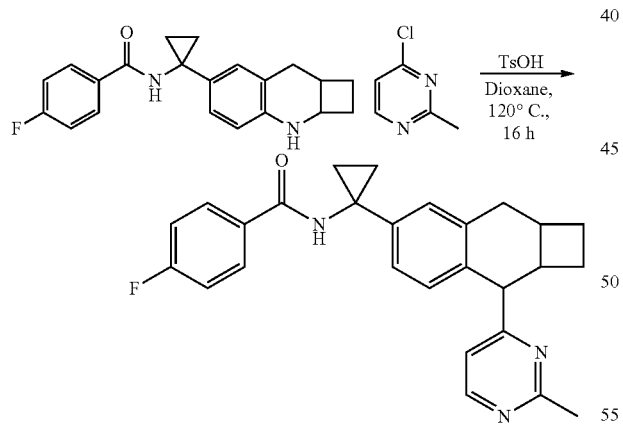

To a stirred solution of 4-fluoro-N-(1-(1,2,2a,3,8,8a-hexahydrocyclobuta[b]quinolin-6-yl)cyclopropyl)benzamide (60 mg, 0.178 mmol) in dioxane (2 mL) were added 4-methylbenzenesulfonic acid (31 mg, 0.180 mmol) and 4-chloro-2-methylpyrimidine (46 mg, 0.358 mmol) at RT. The reaction was allowed to stir at 120° C. for 16 h. After cooling to RT, the mixture was diluted with water (20 mL), and extracted with EtOAc (20 mL×3). The organic layers were collected, washed with brine (10 mL), and dried over Na$_2$SO$_4$. After filtration, the filtrate was concentrated in vacuo. The residue was purified by reverse phase HPLC on a GILSON 281 instrument fitted with a Column Phenomenex Synergi C18 (150×30 mm×5 µm) using water (0.225% FA and ACN as eluents (Mobile phase A water(0.225% FA), Mobile phase B ACN, Detective wavelength: 220 nm) followed by lyophilization to give the title compound as a solid.

MS (ESI) m/z calc'd for C$_{59}$H$_{60}$ClF$_2$N$_8$O$_5$S [M+H]$^+$ 429.20, found 429.1.

$^1$H NMR (500 MHz, CD$_3$OD) δ=8.04 (d, J=6.7 Hz, 1H), 7.98-7.93 (m, 2H), 7.35 (d, J=8.4 Hz, 1H), 7.29-7.20 (m, 4H), 6.87 (d, J=6.7 Hz, 1H), 5.16 (br s, 1H), 2.96 (br s, 1H), 2.84-2.76 (m, 1H), 2.75-2.66 (m, 1H), 2.63 (br d, J=7.3 Hz, 1H), 2.53 (s, 3H), 2.13 (qd, J=8.8, 11.6 Hz, 1H), 1.92-1.87 (m, 1H), 1.60-1.51 (m, 1H), 1.40 (s, 4H).

Examples 6-7: methyl 6-(1-(4-fluorobenzamido)cyclopropyl)-1,2,2a,7b-tetrahydro-3H-cyclobuta[b]indole-3-carboxylate (Isomer 1 and Isomer 2)

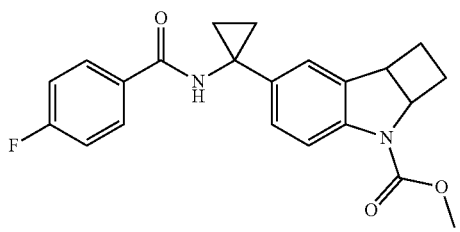 [SMILES: COC(=O)N1c2ccc(C3(NC(=O)c4ccc(F)cc4)CC3)cc2C2CCC21]

Step 1: 2-bromo-N-cyclobutylaniline

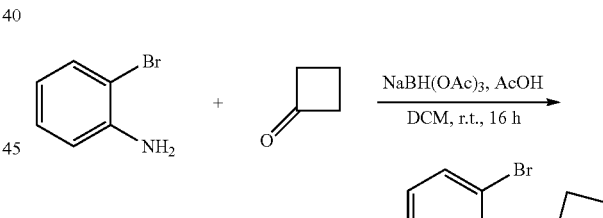

To a solution of 2-bromoaniline (10 g, 58.1 mmol) in DCM (200 mL) were added cyclobutanone (20.37 g, 291 mmol), sodium triacetoxyhydroborate (18.48 g, 87 mmol), and acetic acid (5.24 g, 87 mmol) at 0° C. After addition the reaction was stirred at RT for 16 h. The reaction was concentrated in vacuo. The residue was diluted with water (300 mL), and extracted with DCM (200 mL×3). The organic layers were collected, washed with brine (200 mL), and dried over Na$_2$SO$_4$. After filtration, the filtrate was concentrated in vacuo. The residue was purified by flash silica gel chromatography (ISCO®; Agela® Flash Column Silica-CS (40 g) Eluent of 0-20% Ethyl acetate/Petroleum ether gradient @ 30 mL/min) to give crude title compound as an oil. MS (ESI) m/z calc'd for C$_{10}$H$_{13}$BrN [M+H]$^+$ 226.02, found 226/228.

Step 2: Synthesis of methyl (2-bromophenyl)(cyclobutyl)carbamate

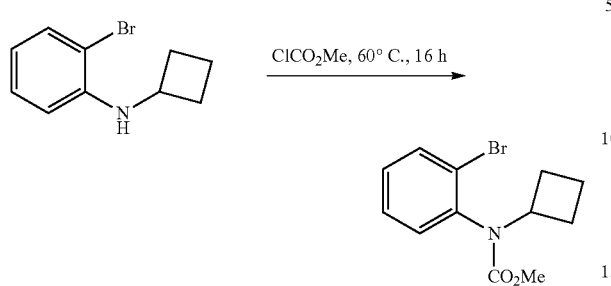

2-Bromo-N-cyclobutylaniline (1 g, 4.42 mmol) was added into methyl carbonochloridate (13.16 g, 139 mmol) at 0° C. After the addition was complete, the mixture was stirred at 60° C. The reaction was monitored by LCMS, after stirring at 60° C. for 16 h, the reaction was finished. The reaction was diluted with water (200 mL), and extracted with DCM (80 mL×3). The combined organic layer was washed with brine (80 mL), dried over $Na_2SO_4$, filtered, and concentrated. The residue was purified by flash silica gel chromatography (ISCO®; Agela® Flash Column Silica-CS (12 g), Eluent of 50% Ethyl acetate/Petroleum ether gradient @ 30 mL/min) to give the title compound as an oil.

MS (ESI) m/z calc'd for $C_{12}H_{15}BrNO_2$ [M+H]$^+$ 284.02, found 284.

Step 3: methyl 1,2,2a,7b-tetrahydro-3H-cyclobuta[b]indole-3-carboxylate

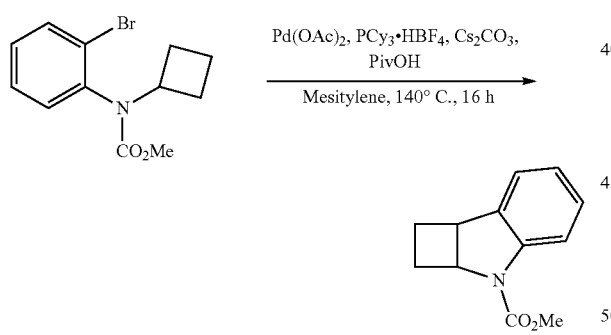

To a stirred solution of methyl (2-bromophenyl)(cyclobutyl)carbamate (800 mg, 2.82 mmol) in mesitylene (10 mL) were added Pd(OAc)$_2$ (32 mg, 0.143 mmol), tricyclohexylphosphonium tetrafluoroborate (104 mg, 0.282 mmol), pivalic acid (86 mg, 0.845 mmol), and cesium carbonate (1.376 g, 4.22 mmol) at RT while stirring at 140° C. for 16 h. The reaction was diluted with water (30 mL), and extracted with DCM (40 mL×3). The combined organic layer was washed with brine (30 mL), dried over $Na_2SO_4$, filtered, and concentrated. The residue was purified by flash silica gel chromatography (ISCO®; Agela® Flash Column Silica-CS (4 g), Eluent of 10% Ethyl acetate/Petroleum ether gradient @ 30 mL/min) to give the title compound as an oil. MS (ESI) m/z calc'd for $C_{12}H_{14}NO_2$ [M+H]$^+$ 204.09, found 204.1.

Step 4: methyl 6-bromo-1,2,2a,7b-tetrahydro-3H-cyclobuta[b]indole-3-carboxylate

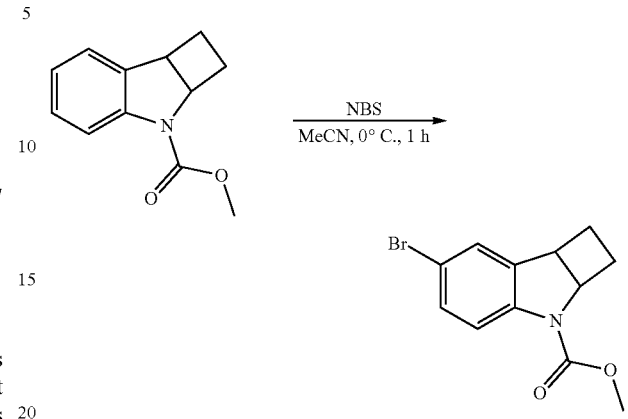

To a stirred solution of methyl 2,2a-dihydro-1H-cyclobuta[b]indole-3(7bH)-carboxylate (1.5 g, 7.38 mmol) in ACN (15 mL) were added 1-bromopyrrolidine-2,5-dione (1.06 g, 5.96 mmol) at 0° C. After the addition was complete, the mixture was stirred at 0° C. for 1 h. The reaction was diluted with water (20 mL), and extracted with $CH_2Cl_2$ (30 mL×3). The combined organic layer was washed with brine (20 mL), dried over $Na_2SO_4$, filtered, and concentrated. The residue was purified by flash silica gel chromatography (ISCO®; Agela® Flash Column Silica-CS (12 g), Eluent of 5% Ethyl acetate/Petroleum ether gradient @ 30 mL/min) to give the title compound as an oil. MS (ESI) m/z calc'd for $C_{12}H_{13}BrNO_2$ [M+H]$^+$ 282.01, found 282.

Step 5: methyl 6-cyano-1,2,2a,7b-tetrahydro-3H-cyclobuta[b]indole-3-carboxylate

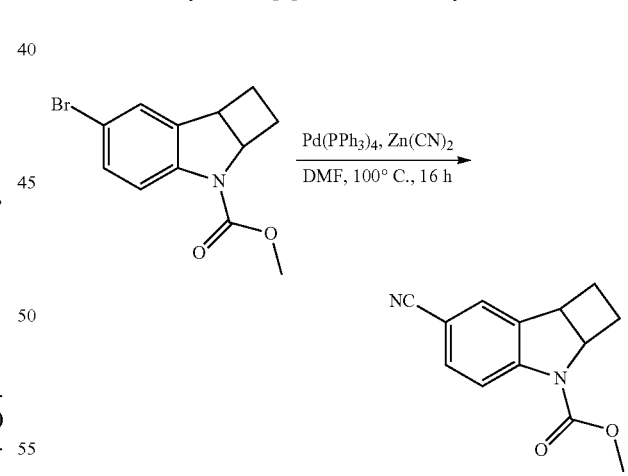

To a stirred solution of methyl 6-bromo-2,2a-dihydro-1H-cyclobuta[b]indole-3(7bH)-carboxylate (1.8 g, 6.38 mmol) and Zn(CN)$_2$ (2.26 g, 19.25 mmol) in DMF (20 mL) was added Pd(PPh$_3$)$_4$ (400 mg, 0.346 mmol) at RT and the reaction was stirred at 100° C. under N$_2$ for 16 h. After cooling to RT, the residue was diluted with water (200 mL), and extracted with EtOAc (40 mL×3). The organic layers were collected, washed with brine, and dried over $Na_2SO_4$. After filtration, the filtrate was concentrated in vacuo. The residue was purified by flash silica gel chromatography (ISCO; Agela Silica Flash Column (12 g), Eluent of 20% ethyl acetate/petroleum ether gradient @ 30 mL/min) to give the title compound as a solid.

Step 6: methyl 6-(1-aminocyclopropyl)-1,2,2a,7b-tetrahydro-3H-cyclobuta[b]indole-3-carboxylate

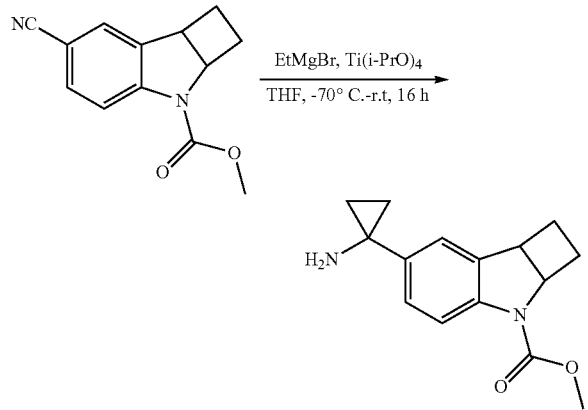

To a stirred solution of methyl 6-cyano-2,2a-dihydro-1H-cyclobuta[b]indole-3(7bH)-carboxylate (400 mg, 1.752 mmol) in THF (10 mL) was added Ti(i-PrO)$_4$ (2.6 mL, 7.10 mmol) while stirring at RT for 0.5 h. The reaction mixture was cooled to −70° C., EtMgBr (3.5 mL, 10.50 mmol) (3.0 M) was then added dropwise. After the addition was finished, the reaction was stirred at −70° C. for 0.5 h, then warmed up to RT and stirred for 16 h. The reaction mixture was diluted with water (20 mL), and extracted with EtOAc (20 mL×3). The organic layers were collected, washed with brine, and dried over Na$_2$SO$_4$. After filtration, the filtrate was concentrated in vacuo. The residue was purified by reversed phase HPLC on a GILSON 281 instrument fitted with a Waters Xbridge Prep OBD C18 150×30 using water (0.04% NH$_3$·H$_2$O+10 mM NH$_4$HCO$_3$)-ACN as eluents, followed by lyophilization to give the title compound as a solid. MS (ESI) m/z calc'd for C$_{15}$H$_{19}$N$_2$O$_2$ [M+H]$^+$ 259.14, found 259.0.

Step 7: methyl 6-(1-(4-fluorobenzamido)cyclopropyl)-1,2,2a,7b-tetrahydro-3H-cyclobuta[b]indole-3-carboxylate

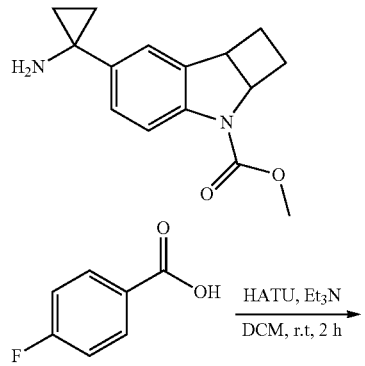

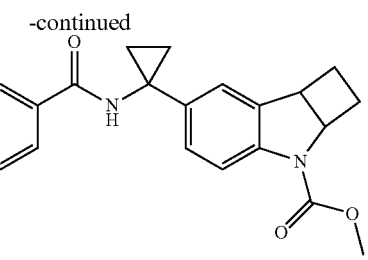

To a stirred solution of methyl 6-(1-aminocyclopropyl)-2,2a-dihydro-1H-cyclobuta[b]indole-3(7bH)-carboxylate (160 mg, 0.619 mmol) and 4-fluorobenzoic acid (87 mg, 0.619 mmol) in DCM (2 mL) were added HATU (236 mg, 0.619 mmol) and TEA (0.26 mL, 1.865 mmol) at RT for 2 h. The residue was purified by reversed phase HPLC on a GILSON 281 instrument fitted with a Waters XSELECT C18 150×30 mm×5 um using water (0.1% TFA)-ACN as eluents, followed by lyophilization to give the title compound as a solid.

MS (ESI) m/z calc'd for C$_{22}$H$_{22}$FN$_2$O$_3$ [M+H]$^+$ 381.15, found 381.2.

$^1$H NMR (500 MHz, CD$_3$OD) δ ppm 7.89 (dd, J=8.70, 5.34 Hz, 2H) 7.37-7.80 (m, 1H) 7.10-7.24 (m, 4H) 4.85 (br s, 1H) 3.68-4.00 (m, 4H) 2.50-2.65 (m, 2H) 2.10-2.21 (m, 1H) 1.85-1.99 (m, 1H) 1.24-1.35 (m, 4H).

After SFC separation, two chiral isomers were obtained
Column DAICEL CHIRALCEL OD-H (250 mm×30 mm, 5 um)
Condition 0.1% NH$_3$H$_2$O MeOH Begin B 40%, End B 40% Gradient Time (min)
100% B Hold Time (min); FlowRate (mL/min) 40
Example 6 (Isomer 1, 1$^{st}$ eluting): MS (ESI) m/z calc'd for C$_{22}$H$_{22}$FN$_2$O$_3$ [M+H]$^+$ 381.15, found 381.2. $^1$H NMR (500 MHz, CDCl$_3$) δ 7.79 (dd, J=8.5, 5.3 Hz, 2H), 7.20 (br d, J=7.0 Hz, 2H), 7.11 (t, J=8.5 Hz, 2H), 6.72 (s, 1H), 4.79 (br s, 1H), 3.69-3.95 (m, 4H), 2.42-2.64 (m, 2H), 2.19 (br s, 1H), 2.01 (br d, J=10.1 Hz, 1H), 1.34 (s, 4H)
Example 7 (Isomer 2, 2$^{nd}$ eluting): MS (ESI) m/z calc'd for C$_{22}$H$_{22}$FN$_2$O$_3$ [M+H]$^+$ 381.15, found 381.2. $^1$H NMR (500 MHz, CDCl$_3$) δ 7.79 (dd, J=8.6, 5.4 Hz, 2H), 7.19 (br d, J=7.2 Hz, 2H), 7.11 (t, J=8.5 Hz, 2H), 6.74 (s, 1H), 4.75-4.97 (m, 1H), 3.75-3.94 (m, 4H), 2.45-2.66 (m, 2H), 2.19 (br s, 1H), 1.97-2.04 (m, 1H), 1.34 (s, 4H).

Examples 8-9: 4-fluoro-N-(1-(2-(2-methylpyrimidin-4-yl)-1,1a,2,6b-tetrahydrocyclopropa[b]indol-5-yl)cyclopropyl)benzamide (Isomer 1 and Isomer 2)

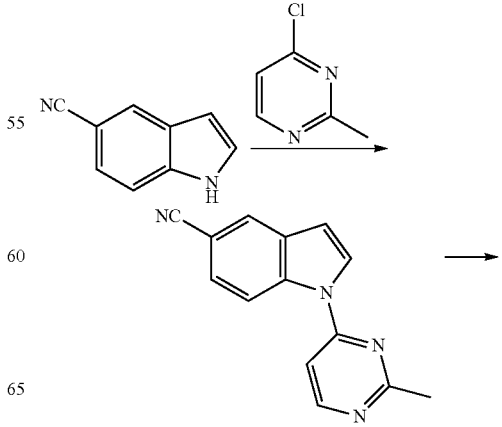

-continued

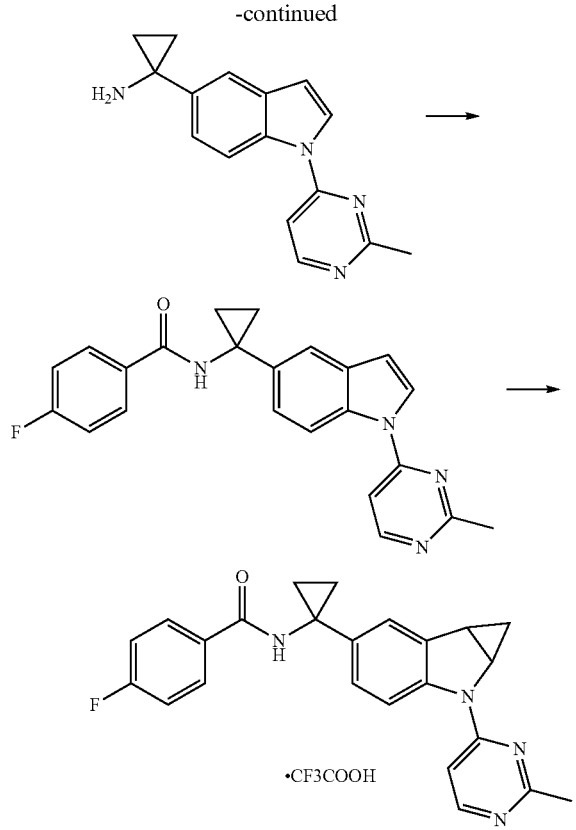

Step 1: 1-(2-methylpyrimidin-4-yl)-1H-indole-5-carbonitrile

To a 40 mL reaction vial with a pressure vent cap were added 1H-indole-5-carbonitrile (1327 mg, 9.33 mmol), followed by DMF (15 ml) and sodium hydride (436 mg, 10.89 mmol). The mixture was allowed to stir for 5 min, then 4-chloro-2-methylpyrimidine (1000 mg, 7.78 mmol) was added. The mixture was heated to 80° C. for 2 h before it was cooled and quenched with water. The mixture was diluted with ethyl acetate, washed with water (3×), dried over MgSO$_4$, filtered, and the solvent was evaporated under reduced pressure to give the title compound as a solid. MS (ESI) m/z calc'd for C$_{14}$H$_{11}$N$_4$ [M+H]$^+$ 235.1, found 235.2.

Step 2: 1-(1-(2-methylpyrimidin-4-yl)-1H-indol-5-yl)cyclopropanamin

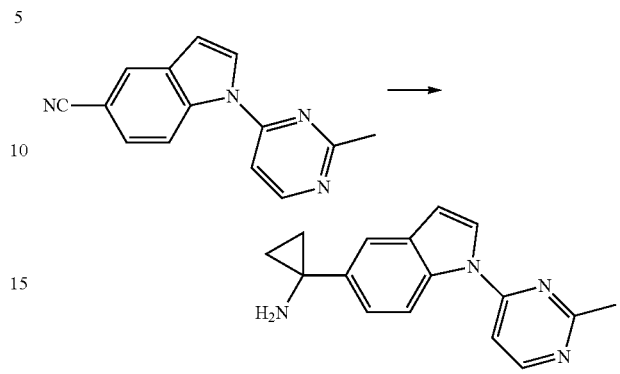

To a solution of 1-(2-methylpyrimidin-4-yl)-1H-indole-5-carbonitrile (500 mg, 2.134 mmol) in THF (7115 µl) at RT was added titanium (IV) isopropoxide (664 µl, 2.241 mmol), followed by the addition of ethylmagnesium bromide 3.0 M in ether (1423 µl, 4.27 mmol). The reaction was slightly extheromic during addition. Water batch was used to maintain internal temperature below 30° C. After the addition, the reaction mixture was kept stirring at RT for 30 min. Then boron trifluoride diethyl etherate (527 µl, 4.27 mmol) was added all at once at RT. The mixture was kept stirring for an additional 30 min. The mixture was quenched by slow additional of 5 ml 1N NaOH, then diluted with water, and extracted with DCM. The combined organics were dried over Na$_2$SO$_4$, and concentrated to give the title compound as a solid. The crude material was carried over to next step. MS (ESI) m/z calc'd for C$_{16}$H$_{17}$N$_4$ [M+H]$^+$ 265.1, found 265.2.

Step 3: 4-fluoro-N-(1-(1-(2-methylpyrimidin-4-yl)-1H-indol-5-yl)cyclopropyl)benzamide

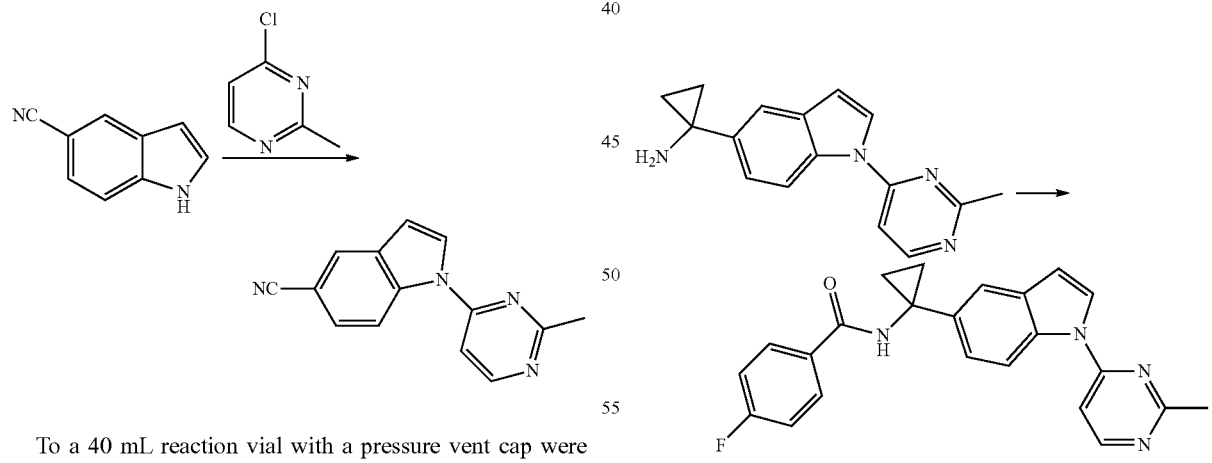

4-Fluorobenzoyl chloride (0.188 ml, 1.589 mmol) was added to a stirred mixture of 1-(1-(2-methylpyrimidin-4-yl)-1H-indol-5-yl)cyclopropanamine (350 mg, 1.324 mmol) and Hunig's Base (0.555 ml, 3.18 mmol) in CH$_2$Cl$_2$ (6 ml) and the mixture was stirred at RT for 1 h. The mixture was diluted with ethyl acetate, washed with aqueous sodium hydrogen carbonate, water, brine, dried over MgSO$_4$, and filtered. The solvent was evaporated under reduced pressure. The residue was purified by column chromatography on ISCO silica gel column (80 g, gold) eluting with EtOAc/isohexane gradient 0-60% to give the title compound as a gum.

MS (ESI) m/z calc'd for $C_{23}H_{20}FN_4O$ [M+H]$^+$ 387.2, found 387.2.

Step 4: 4-fluoro-N-(1-(2-(2-methylpyrimidin-4-yl)-1,1a,2,6b-tetrahydrocyclopropa[b]indol-5-yl)cyclopropyl)benzamide 2,2,2-trifluoroacetate

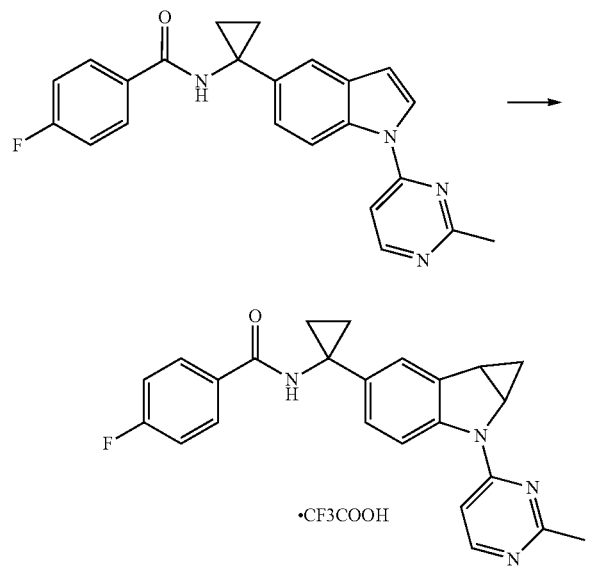

To a solution of diethylzinc (1.397 ml, 1.397 mmol) in $CH_2Cl_2$ (0.5 ml) at 0° C. under argon was added dropwise, and very slowly, a solution of trifluoroacetic acid (0.108 ml, 1.397 mmol) in $CH_2Cl_2$ (0.25 ml). The reaction mixture was stirred for 20 min then a solution of diiodomethane (374 mg, 1.397 mmol) in $CH_2Cl_2$ (0.25 ml) was added dropwise. The reaction mixture was again stirred for 20 min before a solution of 4-fluoro-N-(1-(1-(2-methylpyrimidin-4-yl)-1H-indol-5-yl)cyclopropyl)benzamide (90 mg, 0.233 mmol) in $CH_2Cl_2$ (1.0 ml) was added dropwise. The mixture was allowed to warm to RT and then stirred until the reaction was complete as checked by TLC. The reaction was then quenched at 0° C. by the addition of a sat. solution of $NH_4Cl$ (stirred for 30 min). The crude product was extracted with $CH_2Cl_2$ (×3), the water layer was basified with 1N NaOH to pH 10 and extracted with DCM. The combined DCM layers were washed with water and brine, dried over $MgSO_4$, concentrated under reduced pressure, and purified by reverse phase HPLC under standard conditions to give the title compound as a solid. MS (ESI) m/z calc'd for $C_{24}H_{21}FN_4O$. $CF_3COOH$ [M+H]$^+$ 401.2, found 401.2.

$^1$H NMR (500 MHz, $CD_3OD$) δ 9.29 (s, 1H), 8.34 (d, J=5 Hz, 1H), 7.94 (dd, J=10, 5 Hz, 2H), 7.44 (s, 1H), 7.34 (d, J=5 Hz, 1H), 7.33 (m, 3H), 4.44 (m, 1H), 2.96 (m, 1H), 2.73 (s, 3H), 1.45 (m, 1H), 1.39 (s, 4H), 0.56 (m, 1H).

Chiral Resolution

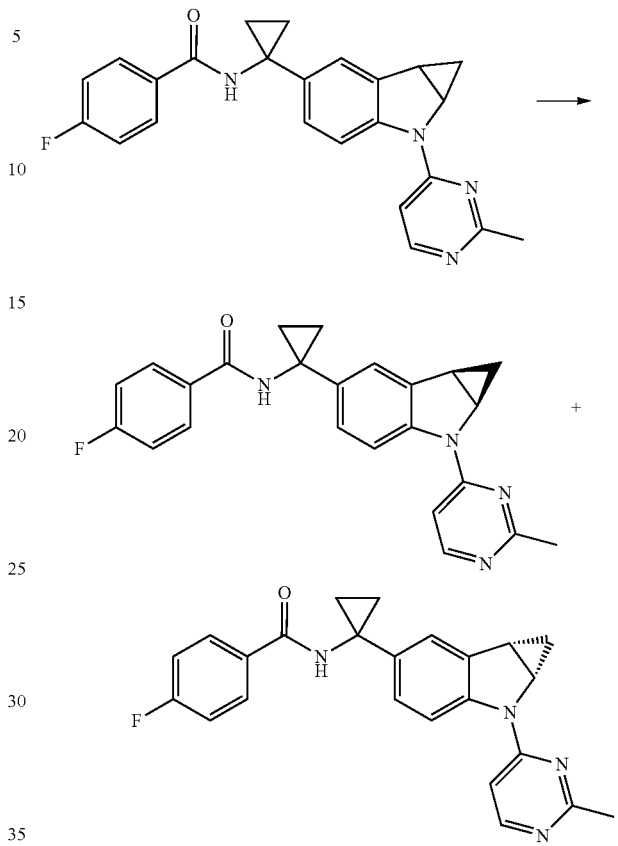

Racemic 4-fluoro-N-(1-(2-(2-methylpyrimidin-4-yl)-1,1a,2,6b-tetrahydrocyclopropa[b]indol-5-yl)cyclopropyl)benzamide 2,2,2-trifluoroacetate (11 mg, 0.021 mmol) was resolved with chiral SFC (EtOH with 0.1% DIPA, AD-H 4.6×250 mm) to give the two enantiomers.

Example 8 (Isomer 1, 1$^{st}$ eluting): MS (ESI) m/z calc'd for $C_{24}H_{21}FN_4O$. $CF_3COOH$ [M+H]$^+$ 401.2, found 401.2.

Example 9 (Isomer 2, 2$^{nd}$ eluting): MS (ESI) m/z calc'd for $C_{24}H_{21}FN_4O$. $CF_3COOH$ [M+H]$^+$ 401.2, found 401.2.

Examples 10-12: 4-fluoro-N-(1-(5-(2-methylpyrimidin-4-yl)-6,6a,7,7a-tetrahydro-5H-cyclopropa[c][1,5]naphthyridin-2-yl)cyclopropyl)benzamide (Isomer 1 and Isomer 2)

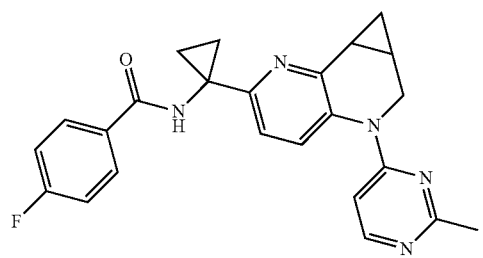 [SMILES: Cc1nccc(N2CC3CC3c3nc(C4(NC(=O)c5ccc(F)cc5)CC4)ccc32)n1]

Step 1: tert-butyl 2-(1-aminocyclopropyl)-6,6a,7,7a-tetrahydro-5H-cyclopropa[c][1,5]naphthyridine-5-carboxylate

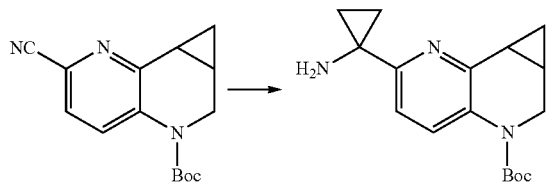 [SMILES: CC(C)(C)OC(=O)N1CC2CC2c2nc(C#N)ccc21 ; CC(C)(C)OC(=O)N1CC2CC2c2nc(C3(N)CC3)ccc21]

To a solution of tert-butyl 2-cyano-6,6a,7,7a-tetrahydro-5H-cyclopropa[c][1,5]naphthyridine-5-carboxylate (340 mg, 1.253 mmol) in Me-THF (3500 µl) at RT was added titanium (IV) isopropoxide (390 µl, 1.316 mmol), followed by addition of ethyl magnesium bromide 3.4 M in Me-THF (737 µl, 2.506 mmol). The reaction was slightly extheromic during addition. After the addition, the reaction mixture was kept stirring at RT for 30 min. Then boron trifluoride diethyl etherate (309 µl, 2.506 mmol) was added all at once at RT. The mixture was kept stirring for additional 30 min. The mixture was quenched by slow addition of 1 ml 1N NaOH in water bath, then diluted with water, and extracted with 1:1 EtOAc 10 ml×3. The combined organics were dried over Na$_2$SO$_4$, and concentrated. The crude material was carried over to next step. MS (ESI+) calcd. for C$_{17}$H$_{24}$N$_3$O$_2$ [M+H]+ 302.18, found 302.

Step 2: tert-butyl 2-(1-(4-fluorobenzamido)cyclopropyl)-6,6a,7,7a-tetrahydro-5H-cyclopropa[c][1,5]naphthyridine-5-carboxylate (Example 10)

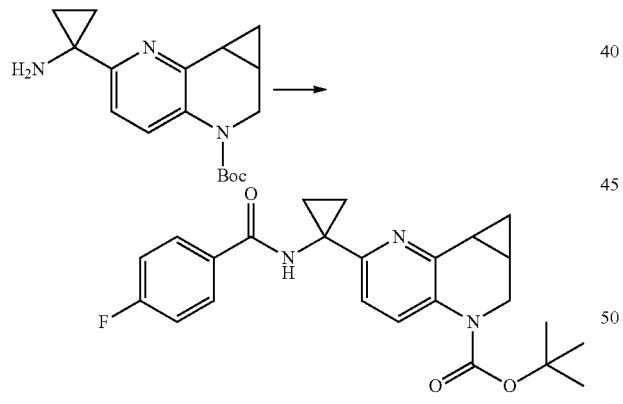

To a 3 L 3-neck round-bottomed flask was charged tert-butyl 2-cyano-6,6a,7,7a-tetrahydro-5H-cyclopropa[c][1,5]naphthyridine-5-carboxylate (40.12 g, 148 mmol). The flask was equipped with an overhead stirrer, a pressure-equalizing addition funnel (250 mL), and a Claisen adapter with a thermocouple probe and a manifold adapter. The contents of the flask were inserted by three consecutive vacuum/nitrogen flushes, and the flask was maintained under nitrogen. To the flask, 2-methyltetrahydrofuran (800 mL) was charged. The solution was cooled with a dry ice/acetone bath. Titanium (IV) isopropoxide (88 ml, 296 mmol) was charged to the addition funnel and then added to the reaction mixture dropwise, maintaining a batch temperature <−70° C. throughout the addition. The addition funnel was rinsed with 2-methyltetrahydrofuran (20 mL) and the rinse was added to the reaction mixture. Ethylmagnesium bromide (3.4 M in 2-methyltetrahydrofuran, 103 mL, 355 mmol) was charged to the addition funnel and then added dropwise to the reaction mixture, maintaining a batch temperature <−70° C. throughout the addition. The addition funnel was rinsed with 2-methyltetrahydrofuran (20 mL) and the rinse was added to the reaction mixture. The reaction mixture was allowed to warm to RT overnight. The reaction mixture was cooled with an ice/water bath and quenched by the addition of saturated aq. sodium chloride solution (800 mL). Celite (120 g) was charged to the mixture, and the suspension was stirred vigorously. The suspension was filtered, and the filter cake was washed with ethyl acetate (500 mL in three portions). The filtrate was transferred to a 4 L separatory funnel, and the phases were separated. The aqueous phase was extracted with EtOAc (500 mL×2). The organic extracts were combined and dried over anhydrous sodium sulfate, filtered, and concentrated to dryness under reduced pressure to afford the title compound.

Tert-butyl 2-(1-aminocyclopropyl)-6,6a,7,7a-tetrahydro-5H-cyclopropa[c][1,5]naphthyridine-5-carboxylate (50.0 g, 148 mmol) was dissolved in dichloromethane (500 mL) under nitrogen and stirred at RT. Triethylamine (62 mL, 445 mmol) was charged, and the solution was cooled with an ice/water bath. 4-Fluorobenzoyl chloride (18.36 mL, 155 mmol) was dissolved in dichloromethane (100 mL) and charged to an addition funnel on the flask. The benzoyl chloride solution was added dropwise to the reaction mixture over 40 min. Saturated aqueous sodium bicarbonate (250 mL) was charged. The phases were separated, and the aqueous phase was extracted with dichloromethane (200 mL). The organic extracts were combined and dried over anhydrous sodium sulfate, filtered, and concentrated under reduced pressure. The residue was purified by column chromatography on silica gel (0-100% ethyl acetate in hexanes) to afford tert-butyl 2-(1-(4-fluorobenzamido)cyclopropyl)-6,6a,7,7a-tetrahydro-5H-cyclopropa[c][1,5]naphthyridine-5-carboxylate.

MS (ESI+) calcd. for C$_{24}$H$_{27}$FN$_3$O$_3$ [M+H]+ 424.2, found 424.2.

Step 3: 4-fluoro-N-(1-(6,6a,7,7a-tetrahydro-5H-cyclopropa[c][1,5]naphthyridin-2-yl)cyclopropyl)benzamide (Example 11)

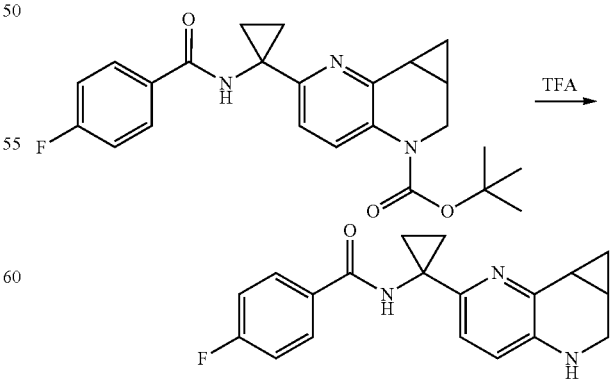

Tert-butyl 2-(1-(4-fluorobenzamido)cyclopropyl)-6,6a,7,7a-tetrahydro-5H-cyclopropa[c][1,5]naphthyridine-5-carboxylate (41.77 g, 99 mmol) was charged to a 1 L 2-neck RBF equipped with a stir bar, thermocouple, and a manifold adapter. The flask was placed under an inert atmosphere of nitrogen by performing three vacuum/nitrogen cycles. Dichloromethane (418 mL) was charged, and the resulting solution was cooled with an ice/acetone bath to a batch temperature of approx. −5 to −10° C. Trifluoroacetic acid (22.80 mL, 296 mmol) was charged dropwise and the reaction mixture was warmed to RT. After 3 h, trifluoroacetic acid (100 mL, 1298 mmol) was charged, and the mixture was stirred at RT overnight. The reaction solution was concentrated under reduced pressure to afford an oil to which saturated aqueous sodium bicarbonate (500 mL) was charged. The aqueous phase was extracted with dichloromethane (500 mL then 250 mL×2). The combined organic extracts were dried over anhydrous sodium sulfate, filtered, and concentrated under reduced pressure to afford the title compound.

MS (ESI+) calcd. for $C_{19}H_{19}FN_3O$ [M+H]+ 324.1, found 324.1.

Step 4: 4-fluoro-N-(1-(5-(2-methylpyrimidin-4-yl)-6,6a,7,7a-tetrahydro-5H-cyclopropa[c][1,5]naphthyridin-2-yl)cyclopropyl)benzamide (Examples 12 and 13)

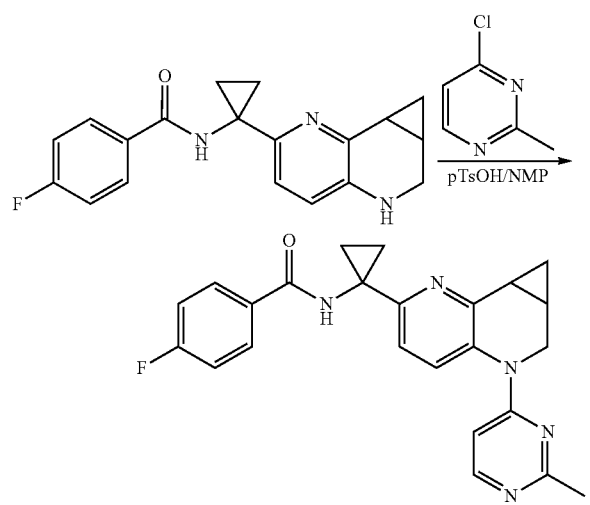

4-Fluoro-N-(1-(6,6a,7,7a-tetrahydro-5H-cyclopropa[c][1,5]naphthyridin-2-yl)cyclopropyl)benzamide (29.08 g, 90 mmol), 4-chloro-2-methylpyrimidine (29.34 g, 228 mmol), and p-toluenesulfonic acid monohydrate (19.85 g, 104 mmol) were dissolved in N-methyl-2-pyrrolidinone (291 mL). The resulting mixture was heated to 65° C. After 15 h, the reaction temperature was increased to 75° C., and 4-chloro-2-methylpyridine (26.12 g, 203 mmol) was charged. After 24 h, the mixture was cooled to RT and poured into water (500 mL) then stirred vigorously. The aqueous phase was extracted with dichloromethane (500 mL×2). The aqueous phase was neutralized with aqueous sodium hydroxide (2 M to pH >10) then extracted with ethyl acetate (500 mL×2). The combined organic extracts were washed with water (100 mL×3), then brine (100 mL), dried over anhydrous sodium sulfate, filtered, and concentrated under reduced pressure. The residue was purified twice by column chromatography on silica gel (0-100% ethyl acetate in hexanes then 0-100% methanol in water) to afford 4-fluoro-N-(1-(5-(2-methylpyrimidin-4-yl)-6,6a,7,7a-tetrahydro-5H-cyclopropa[c][1,5]naphthyridin-2-yl)cyclopropyl)benzamide. The racemic mixture was purified by chiral SFC (OJ-H 21×250 column, 20%/80% MeOH with 0.25% dimethylethylamine/$CO_2$) to afford two isomers of 4-fluoro-N-(1-(5-(2-methylpyrimidin-4-yl)-6,6a,7,7a-tetrahydro-5H-cyclopropa[c][1,5]naphthyridin-2-yl)cyclopropyl)benzamide.

Example 12 (Isomer 1, First Eluting)

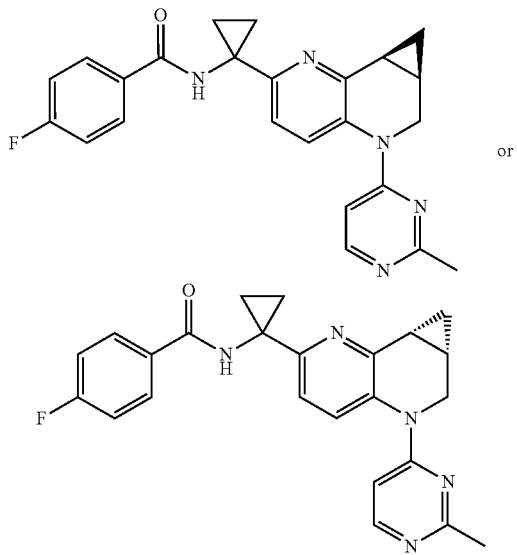

MS ESI calcd. for $C_{24}H_{23}FN_5O$ [M+H]+ 416.18, found 416; $^1$H NMR (600 MHz, DMSO-$d_6$) δ 9.27 (s, 1H), 8.12 (d, J=6.1 Hz, 1H), 8.01 (dd, J=8.8 ($J_{HH}$), 5.7 Hz ($J_{HF}$), 2H), 7.57 (d, J=8.4 Hz, 1H), 7.32 (t, J=8.8 Hz ($J_{HH}$, $J_{HF}$), 2H), 7.14 (d, J=8.4 Hz, 1H), 6.63 (d, J=6.1 Hz, 1H), 5.11 (d, J=12.9 Hz, 1H), 2.92 (d, J=12.9 Hz, 1H), 2.42 (s, 3H), 2.14 (td, J=8.5, 4.4 Hz, 1H), 2.09 (td, J=7.9, 5.8 Hz, 1H), 1.59 (dd, J=5.6, 2.5 Hz, 2H), 1.25 (dd, J=4.3, 3.1 Hz, 2H), 1.04 (td, J=8.4, 4.9 Hz, 1H), 0.54 (q, J=4.8 Hz, 1H).

$^{13}$C NMR (150.8 MHz, DMSO-$d_6$) δ 166.77, 165.96, 163.90 (d, $^1J_{CF}$=248.7 Hz), 161.10, 156.97, 156.35, 152.41, 130.76, 130.69 (d, $4J_{CF}$=2.6 Hz), 129.96 (d, $^3J_{CF}$=8.9 Hz, 2C), 128.74, 116.01, 115.11 (d, $^2J_{CF}$=21.7 Hz, 2C), 101.68, 38.24, 35.90, 25.76, 20.63, 18.49 (2C), 16.88, 8.52

Example 13 (Isomer 2, Second Eluting)

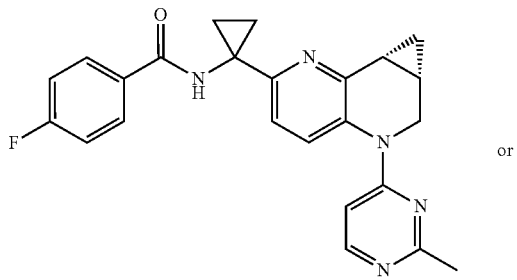

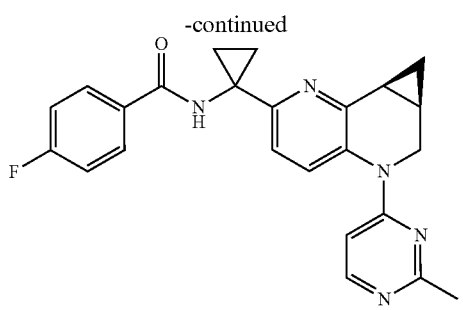

MS ESI calcd. for $C_{24}H_{23}FN_5O$ [M+H]$^+$ 416, found 416.
$^1$H NMR (600 MHz, DMSO-d$_6$) δ 9.27 (s, 1H), 8.12 (d, J=6.1 Hz, 1H), 8.01 (dd, J=8.8 (J$_{HH}$), 5.7 Hz (J$_{HF}$), 2H), 7.57 (d, J=8.4 Hz, 1H), 7.32 (t, J=8.8 Hz (J$_{HH}$, J$_{HF}$), 2H), 7.14 (d, J=8.4 Hz, 1H), 6.63 (d, J=6.1 Hz, 1H), 5.11 (d, J=12.9 Hz, 1H), 2.92 (d, J=12.9 Hz, 1H), 2.42 (s, 3H), 2.14 (td, J=8.5, 4.4 Hz, 1H), 2.09 (td, J=7.9, 5.8 Hz, 1H), 1.59 (dd, J=5.6, 2.5 Hz, 2H), 1.25 (dd, J=4.3, 3.1 Hz, 2H), 1.04 (td, J=8.4, 4.9 Hz, 1H), 0.54 (q, J=4.8 Hz, 1H). $^{13}$C NMR (150.8 MHz, DMSO-d$_6$) δ 166.77, 165.96, 163.90 (d, $^1$J$_{CF}$=248.7 Hz), 161.10, 156.97, 156.35, 152.41, 130.76, 130.69 (d, 4J$_{CF}$=2.6 Hz), 129.96 (d, $^3$J$_{CF}$=8.9 Hz, 2C), 128.74, 116.01, 115.11 (d, $^2$J$_{CF}$=21.7 Hz, 2C), 101.68, 38.24, 35.90, 25.76, 20.63, 18.49 (2C), 16.88, 8.52.

The following compounds were synthesized in a similar manner using common Intermediate B and the appropriate halogenated heterocycle and following procedure as described for Step 4 of Examples 6-7.

| Ex. # | Structure | Chemical Name | Mass [M + H]+ |
|---|---|---|---|
| 14 | 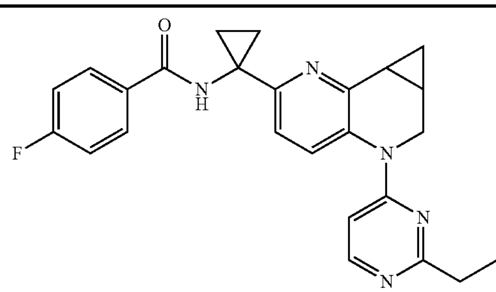 | N-(1-(5-(2-ethylpyrimidin-4-yl)-6,6a,7,7a-tetrahydro-5H-cyclopropa[c][1,5]-naphthyridin-2-yl)cyclopropyl)-4-fluorobenzamide | 430.2 |
| 15 | 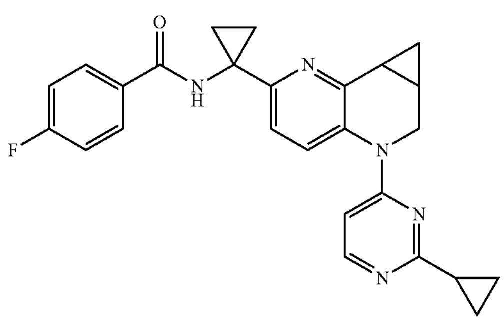 | N-(1-(5-(2-cyclopropyl-pyrimidin-4-yl)-6,6a,7,7a-tetrahydro-5H-cyclopropa[c][1,5]naphthyridin-2-yl)cyclopropyl)-4-fluorobenzamide Isomer 1 | 442.2 |
| 16 | 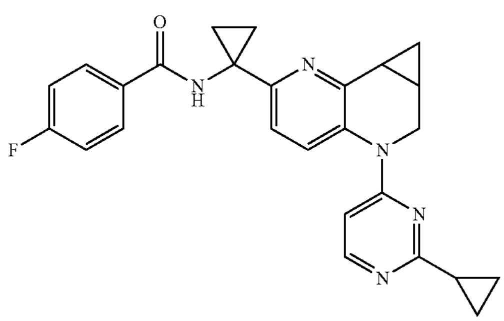 | N-(1-(5-(2-cyclopropyl-pyrimidin-4-yl)-6,6a,7,7a-tetrahydro-5H-cyclopropa[c][1,5]naphthyridin-2-yl)cyclopropyl)-4-fluorobenzamide Isomer 2 | 442.2 |

Example 17: methyl 4-(2-(1-(4-fluorobenzamido)cyclopropyl)-6,6a,7,7a-tetrahydro-5H-cyclopropa[c][1,5]naphthyridin-5-yl)pyrimidine-2-carboxylate

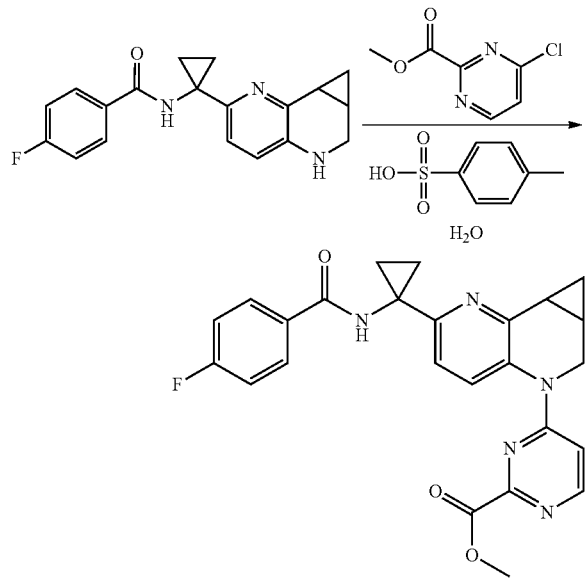

To a reaction vial was added p-toluenesulfonic acid monohydrate (64.7 mg, 0.340 mmol) and methyl 4-chloropyrimidine-2-carboxylate (160 mg, 0.928 mmol), followed by 1,4-dioxane (2 ml) and 4-fluoro-N-(1-(6,6a,7,7a-tetrahydro-5H-cyclopropa[c][1,5]naphthyridin-2-yl)cyclopropyl)benzamide (100 mg, 0.309 mmol). The mixture was stirred at 80° C. for 7 h before cooled down and diluted with EtOAc and water. The organic layer was concentrated, purified on normal phase chromatography on silica gel with 0 to 100% EtOAc in hexane. The title product was re-purified by reverse phase chromatography with 10 to 100% ACN in water with 0.05% TFA. The title compound was isolated and lyophilized as a solid.

MS (ESI) m/z calc'd for $C_{25}H_{23}FN_5O_3 \cdot TFA$ [M+H]$^+$ 460.17, found 460.3.

Example 18: 4-fluoro-N-(1-(5-(2-(2-hydroxypropan-2-yl)pyrimidin-4-yl)-6,6a,7,7a-tetrahydro-5H-cyclopropa[c][1,5]naphthyridin-2-yl)cyclopropyl)benzamide

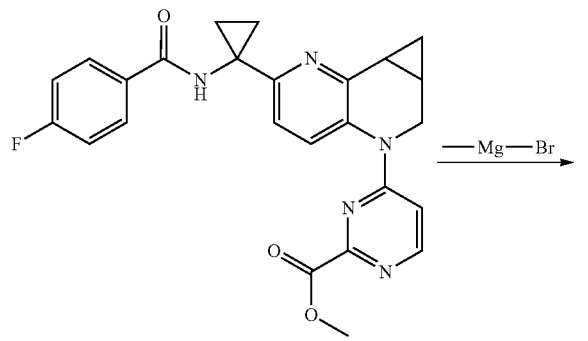

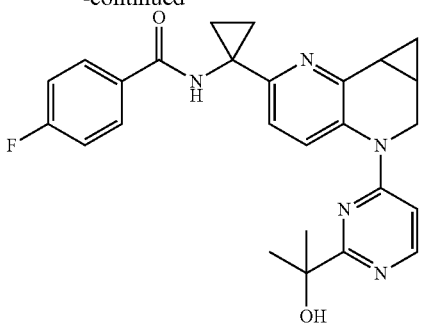

To a THF (0.3 ml) solution of methyl 4-(2-(1-(4-fluorobenzamido)cyclopropyl)-6,6a,7,7a-tetrahydro-5H-cyclopropa[c][1,5]naphthyridin-5-yl)pyrimidine-2-carboxylate (16 mg, 0.035 mmol) at 0° C. was added methylmagnesium bromide (0.058 ml, 0.174 mmol). The mixture was then stirred at RT for 30 min. The mixture was cooled back to 0° C., quenched with saturated ammonium chloride, and diluted with EtOAc. The organic layer was concentrated, purified by reverse phase chromatography on C18 column with 10 to 100% ACN in water with 0.05% TFA, the title compound was isolated and lyophilized as a solid.

MS (ESI) m/z calc'd for $C_{26}H_{27}FN_5O_2 \cdot TFA$ [M+H]$^+$ 460.21, found 460.3.

Example 19: 4-fluoro-N-(1-(5-(2-(hydroxymethyl)pyrimidin-4-yl)-6,6a,7,7a-tetrahydro-5H-cyclopropa[c][1,5]naphthyridin-2-yl)cyclopropyl)benzamide

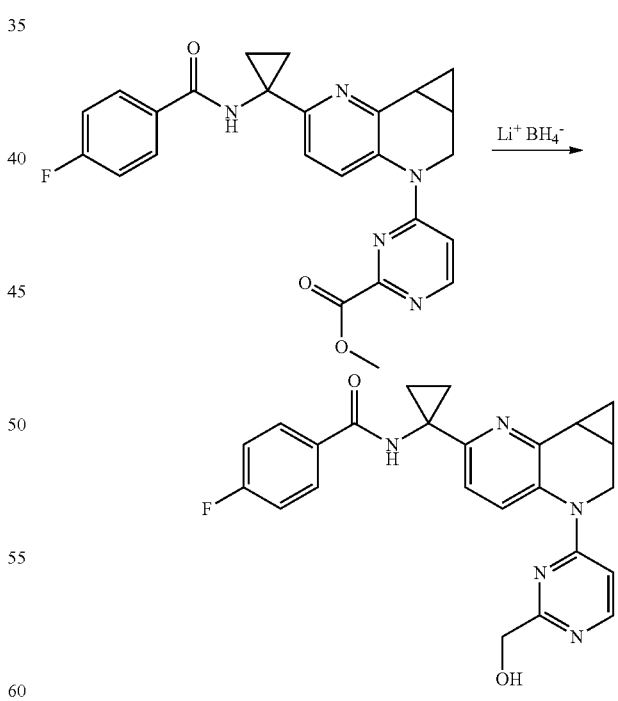

To a THF (0.5 ml) solution of methyl 4-(2-(1-(4-fluorobenzamido)cyclopropyl)-6,6a,7,7a-tetrahydro-5H-cyclopropa[c][1,5]naphthyridin-5-yl)pyrimidine-2-carboxylate (11 mg, 0.024 mmol) at 0° C. was added lithium borohydride (0.036 ml, 0.072 mmol). The mixture was then stirred at RT for 30 min, before being cooled to 0° C. and diluted with 3 ml EtOAc, and quenched with saturated ammonium chloride. The organic layer was concentrated, purified on reverse phase chromatography on C18 column with 10 to 100% ACN in water with 0.05% TFA, The title compound was isolated and lyophilized as a solid.

MS (ESI) m/z calc'd for $C_{24}H_{23}FN_5O_2 \cdot TFA$ [M+H]$^+$ 432.18, found 432.2.

$^1$H NMR (500 MHz, Chloroform-d) δ 8.85 (s, 1H), 8.31 (m, 1H), 7.95 (s, 2H), 7.84 (d, J=8.6 Hz, 1H), 7.63 (d, J=8.1 Hz, 1H), 7.22-7.04 (m, 2H), 6.88 (d, J=6.3 Hz, 1H), 5.27 (d, J=13.1 Hz, 1H), 4.82 (s, 2H), 3.20 (d, J=13.3 Hz, 1H), 2.34 (s, 1H), 1.65 (d, J=8.8 Hz, 2H), 1.53 (m, 2H), 1.44 (d, J=7.0 Hz, 1H), 1.28 (s, 1H), 0.93 (d, J=22.0 Hz, 2H).

Examples 20-21: (6aR,7aS)-cyclopropyl 2-(1-(4-fluorobenzamido)cyclopropyl)-6,6a,7,7a-tetrahydro-5H-cyclopropa[c][1,5]naphthyridine-5-carboxylate (Isomer 1 and Isomer 2)

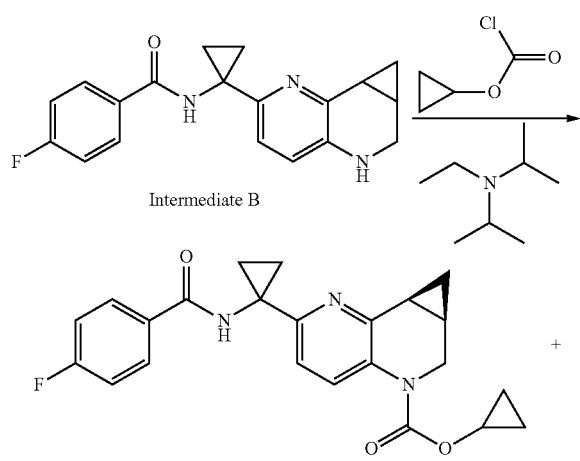

Intermediate B

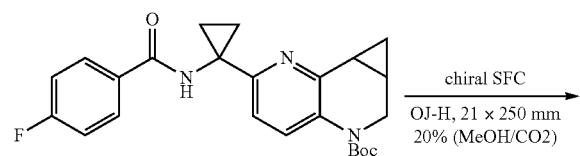

chiral SFC
OJ-H, 21 × 250 mm
20% (MeOH/CO2)

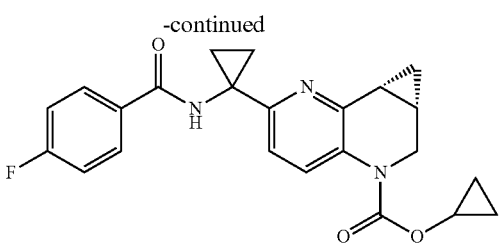

To a solution of 4-fluoro-N-(1-(6,6a,7,7a-tetrahydro-5H-cyclopropa[c][1,5]naphthyridin-2-yl)cyclopropyl)benzamide (150 mg, 0.464 mmol) and N-ethyl-N-isopropylpropan-2-amine (0.243 ml, 1.392 mmol) in CH$_2$Cl$_2$ (5 ml) was added cyclopropyl carbonochloridate (112 mg, 0.928 mmol) dropwise and stirred at RT overnight. The reaction mixture was monitored by LC. Excess solvent was removed in-vacuo and this was purified by HPLC using gradient elution with water/ACN. This was lyophilized and a solid was obtained and separated on Chiral SFC.

Example 20 (Isomer 1, 1$^{st}$ eluting): (6aR,7aS)-cyclopropyl 2-(1-(4-fluorobenzamido)cyclopropyl)-6,6a,7,7a-tetrahydro-5H-cyclopropa[c][1,5]naphthyridine-5-carboxylate MS (ESI) m/z calc'd for $C_{23}H_{23}FN_3O_3$ [M+H]$^+$ 408.16, found 408.1.

Example 21 (Isomer 2, 2$^{nd}$ eluting): (6aS,7aR)-cyclopropyl 2-(1-(4-fluorobenzamido)cyclopropyl)-6,6a,7,7a-tetrahydro-5H-cyclopropa[c][1,5]naphthyridine-5-carboxylate MS (ESI) m/z calc'd for $C_{23}H_{23}FN_3O_3$ [M+H]$^+$ 408.16, found 408.1.

Examples 22-23 was prepared using a similar procedure as for Examples 20-21.

Examples 22-23: tetrahydro-2H-pyran-4-yl 2-(1-(4-fluorobenzamido)cyclopropyl)-6,6a,7,7a-tetrahydro-5H-cyclopropa[c][1,5]naphthyridine-5-carboxylate enantiomer1

HCl enantiomer2

HCl

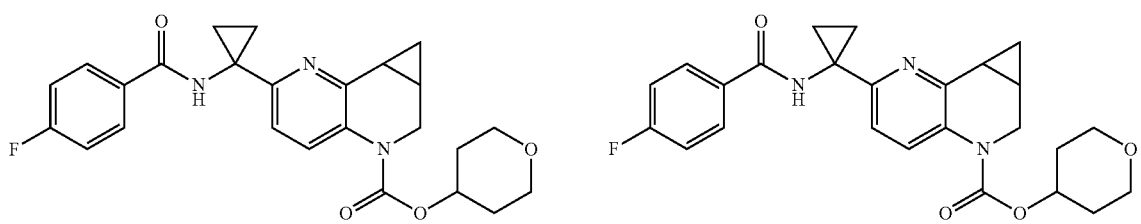

| Ex. # | Structure | Chemical Name | Mass [M + H]+ |
|---|---|---|---|
| 22 | 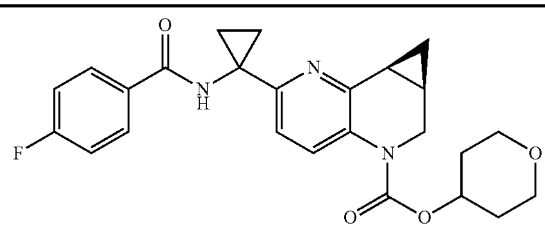 | tetrahydro-2H-pyran-4-yl (6aR,7aS)-2-(1-(4-fluorobenzamido)cyclopropyl)-6,6a,7,7a-tetrahydro-5H-cyclopropa[c][1,5]naphthyridine-5-carboxylate | 452.37 |
| 23 | 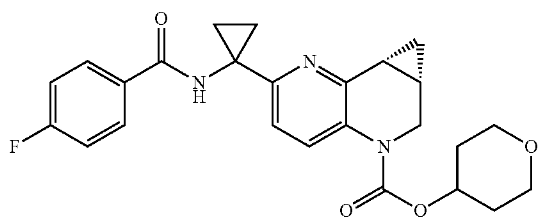 [SMILES: O=C(NC1(c2ccc3c(n2)[C@@H]2C[C@@H]2CN3C(=O)OC2CCOCC2)CC1)c1ccc(F)cc1] | tetrahydro-2H-pyran-4-yl (6aS,7aR)-2-(1-(4-fluorobenzamido)cyclopropyl)-6,6a,7,7a-tetrahydro-5H-cyclopropa[c][1,5]-naphthyridine-5-carboxylate | 452.37 |

Examples 24-28: tert-butyl 2-(1-(4-fluorobenzamido)ethyl)-6,6a,7,7a-tetrahydro-5H-cyclopropa[c][1,5]naphthyridine-5-carboxylate (Example 24) and cyclopropyl 2-(1-(4-fluorobenzamido)ethyl)-6,6a,7,7a-tetrahydro-5H-cyclopropa[c][1,5]naphthyridine-5-carboxylate (Examples 25-28; Isomers 1-4)

Step 1: tert-butyl 2-acetyl-6,6a,7,7a-tetrahydro-5H-cyclopropa[c][1,5]naphthyridine-5-carboxylate

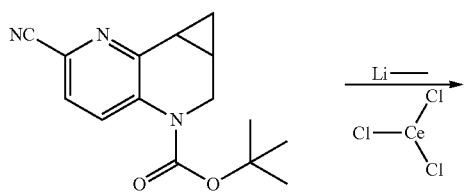

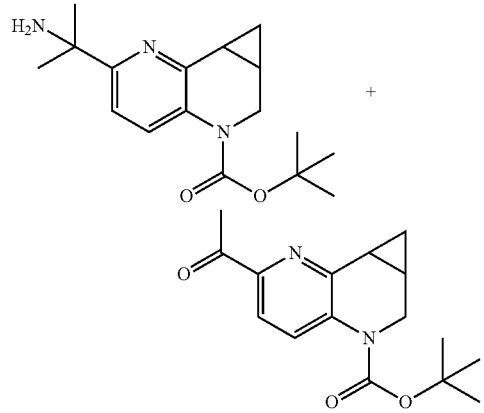

To anhydrous cerium chloride (III) (1.426 g, 5.79 mmol), THF (25 ml) was added, and the slurry was stirred under nitrogen for 30 min. The mixture was cooled to −76° C. in a dry-ice acetone bath. 1.6 M solution of methyllithium in Et₂O (3.46 ml, 5.53 mmol) was added dropwise while maintaining the internal reaction temperature below −60° C. This was stirred for 30 min after the addition. The reaction was cooled back to −76° C., then tert-butyl 2-cyano-6,6a,7,7a-tetrahydro-5H-cyclopropa[c][1,5]naphthyridine-5-carboxylate (500 mg, 1.843 mmol) was added as a solution in THF (5 ml) while controlling the addition to keep the reaction below −60° C. The mixture was stirred in the dry-ice bath for 15 min, then the bath was removed and allowed to warm to 15° C. The reaction was cooled in the dry-ice bath and ammonium hydroxide (20 mL) was added with stirring. The reaction was allowed to warm to RT with stirring overnight. The solution was decanted from the mixture, and the solids washed well with THF. The filtrate and washes were combined and evaporated to afford the title compound.

MS (ESI) m/z calc'd for $C_{16}H_{21}N_2O_3$ [M+H]$^+$ 289.19, found 289.1.

Step 2: tert-butyl 2-(1-aminoethyl)-6,6a,7,7a-tetrahydro-5H-cyclopropa[c][1,5]naphthyridine-5-carboxylate

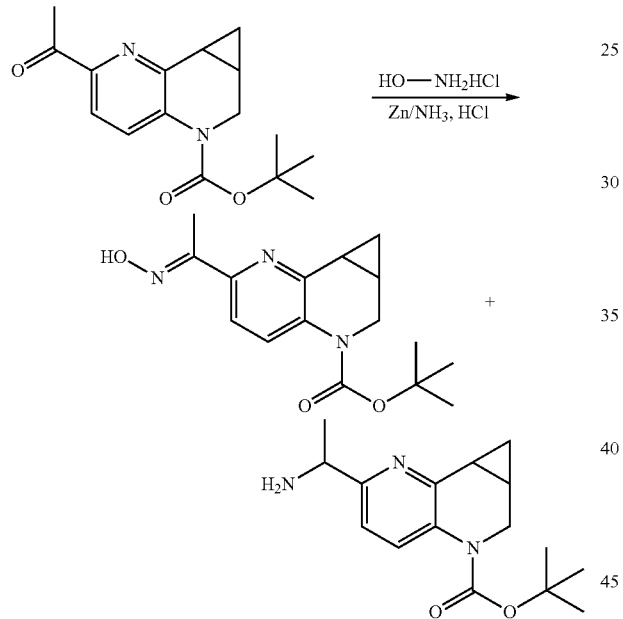

Tert-butyl 2-acetyl-6,6a,7,7a-tetrahydro-5H-cyclopropa[c][1,5]naphthyridine-5-carboxylate (550 mg, 1.907 mmol) and hydroxylamine hydrochloride (146 mg, 2.098 mmol) were dissolved in methanol (15 ml) at RT. Potassium carbonate (791 mg, 5.72 mmol) was added with stirring. The reaction mixture was stirred at RT for 4 h. The solids were filtered, and to the filtrate were added zinc (624 mg, 9.54 mmol) and ammonium chloride (510 mg, 9.54 mmol) in that order. The reaction mixture was stirred for 3 h, monitored by LCMS m/z 304 [M+H] corresponded to oxime intermediate. The reaction was heated at 50° C. overnight. LCMS showed m/z 290 [M+H] for the desired product. The solids were filtered, the organic solvent was removed by steam distillation under reduced pressure. To the crude product was added an aqueous solution of sodium hydroxide to adjust the pH ~13. This was then extracted with dichloromethane (50 mL×3). The combined organic phases were washed with saturated brine, dried over anhydrous sodium sulfate and steamed to give the title compound.

MS (ESI) m/z calc'd for $C_{16}H_{24}N_3O_2$ [M+H]$^+$, 290.18, found 290.2.

Step 3: tert-butyl 2-(1-(4-fluorobenzamido)ethyl)-6,6a,7,7a-tetrahydro-5H-cyclopropa[c][1,5]naphthyridine-5-carboxylate (Example 24)

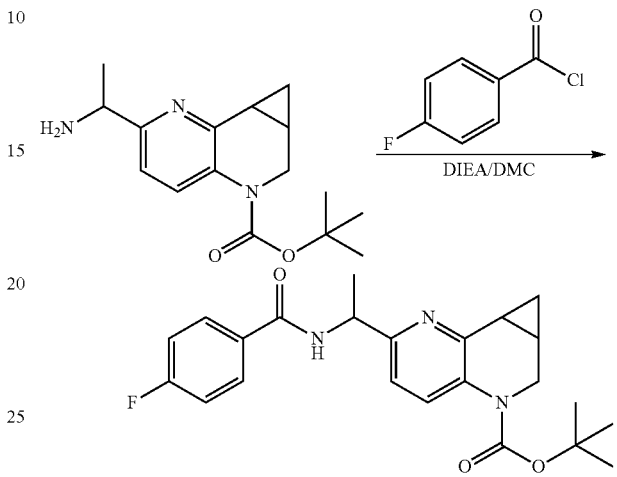

To a flask was added tert-butyl 2-(1-aminoethyl)-6,6a,7,7a-tetrahydro-5H-cyclopropa[c][1,5]naphthyridine-5-carboxylate (550 mg, 1.901 mmol), and it was dissolved in DCM (5 ml). To this were added N-ethyl-N-isopropylpropan-2-amine (1.053 ml, 5.70 mmol) followed by the 4-fluorobenzoyl chloride (0.247 ml, 2.091 mmol). This was allowed to stir at RT for 5 min. The reaction was quenched with 0.25 ml of water, evaporated in vacuo, and purified by HPLC using ACN/water to give the title compound.

MS (ESI) m/z calc'd for $C_{23}H_{26}FN_3O_3$[M+H]$^+$ 412.20, found 412.5.

Step 4: 4-fluoro-N-(1-(6,6a,7,7a-tetrahydro-5H-cyclopropa[c][1,5]naphthyridin-2-yl)ethyl)benzamide—Intermediate C

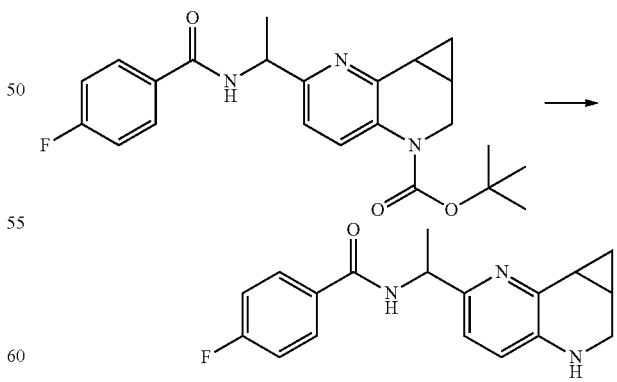

Tert-butyl 2-(1-(4-fluorobenzamido)ethyl)-6,6a,7,7a-tetrahydro-5H-cyclopropa[c][1,5]naphthyridine-5-carboxylate (200 mg, 0.486 mmol) was dissolved in DCM (5 ml) and to this hydrochloric acid 4 M in dioxane (0.122 ml, 0.486 mmol) was added and stirred at RT overnight. The reaction was monitored by LCMS. The reaction was concentrated under reduced pressure and used as is for the next step.

MS (ESI) m/z calc'd for $C_{18}H_{19}FN_3O$ $[M+H]^+$ 312.14, found 312.1.

Step 5: cyclopropyl 2-(1-(4-fluorobenzamido)ethyl)-6,6a,7,7a-tetrahydro-5H-cyclopropa[c][1,5]naphthyridine-5-carboxylate

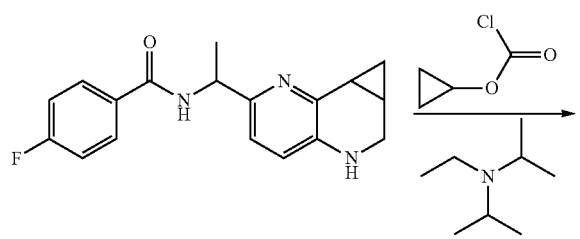

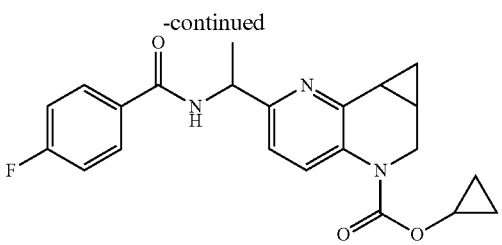

4-Fluoro-N-(1-(6,6a,7,7a-tetrahydro-5H-cyclopropa[c][1,5]naphthyridin-2-yl)ethyl)benzamide (150 mg, 0.482 mmol) was dissolved in DCM (5 ml) and N-ethyl-N-isopropylpropan-2-amine (0.421 ml, 2.409 mmol) was added, followed by cyclopropyl carbonochloridate (116 mg, 0.964 mmol). The mixture was stirred at RT overnight. The crude was concentrated in vacuo and washed with water, and extracted with EtOAC. The organic layer was washed with brine and dried over $Na_2SO_4$. The residue was purified by column chromatography using 0-60% hexane/(3:1 EtOAc:EtOH). The purified material was submitted for chiral separation, four peaks were isolated, analyzed and submitted as shown in table

| Ex. # | Structure | Chemical Name | [M + H]+ |
|---|---|---|---|
| 25 | 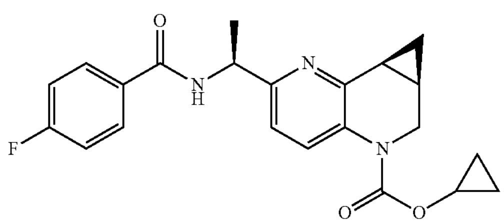 [SMILES: C[C@H](NC(=O)c1ccc(F)cc1)c1ccc2c(n1)[C@H]1C[C@H]1CN2C(=O)OC1CC1] | cyclopropyl (6aR,7aS)-2-((S)-1-(4-fluorobenzamido)-ethyl)-6,6a,7,7a-tetrahydro-5H-cyclopropa[c][1,5]-naphthyridine-5-carboxylate | 396.0 |
| 26 | 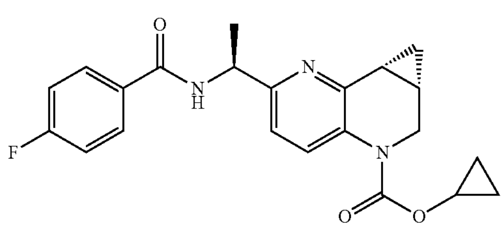 [SMILES: C[C@H](NC(=O)c1ccc(F)cc1)c1ccc2c(n1)[C@@H]1C[C@@H]1CN2C(=O)OC1CC1] | cyclopropyl (6aS,7aR)-2-((S)-1-(4-fluorobenzamido)-ethyl)-6,6a,7,7a-tetrahydro-5H-cyclopropa[c][1,5]-naphthyridine-5-carboxylate | 396.1 |
| 27 | 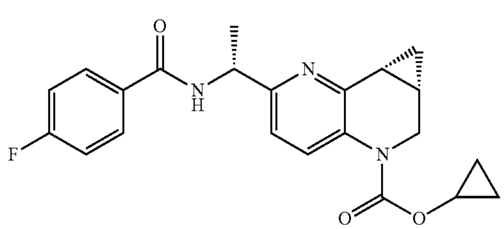 [SMILES: C[C@@H](NC(=O)c1ccc(F)cc1)c1ccc2c(n1)[C@@H]1C[C@@H]1CN2C(=O)OC1CC1] | cyclopropyl (6aS,7aR)-2-((R)-1-(4-fluorobenzamido)-ethyl)-6,6a,7,7a-tetrahydro-5H-cyclopropa[c][1,5]-naphthyridine-5-carboxylate | 396.1 |
| 28 | 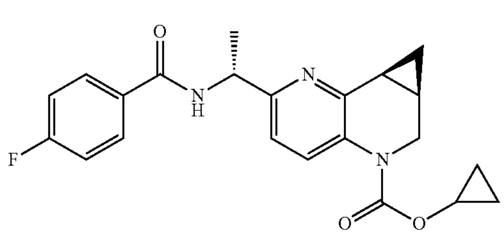 [SMILES: C[C@@H](NC(=O)c1ccc(F)cc1)c1ccc2c(n1)[C@H]1C[C@H]1CN2C(=O)OC1CC1] | cyclopropyl (6aR,7aS)-2-((R)-1-(4-fluorobenzamido)-ethyl)-6,6a,7,7a-tetrahydro-5H-cyclopropa[c][1,5]-naphthyridine-5-carboxylate | 396.1 |

Examples 29-31: 4-fluoro-N-(2-(5-(2-methylpyrimidin-4-yl)-6,6a,7,7a-tetrahydro-5H-cyclopropa[c][1,5]naphthyridin-2-yl)propan-2-yl)benzamide (Racemic, Isomer 1 and Isomer 2)

Step 1: tert-butyl 2-(2-aminopropan-2-yl)-6,6a,7,7a-tetrahydro-5H-cyclopropa[c][1,5]naphthyridine-5-carboxylate

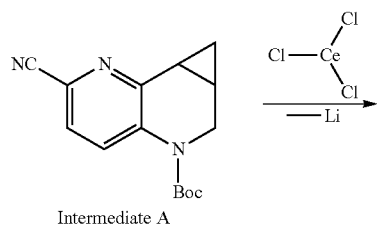

Intermediate A

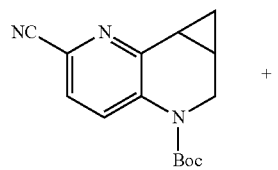

To a RBF was added cerium (III) chloride (2180 mg, 8.85 mmol) with a stir bar. The mixture was heated to 140° C. under high vacuum for 30 min, then cooled down, backfilled with N$_2$, and followed by the addition of THF (12 ml). The mixture was then stirred at −78° C., and methyl lithium (2.85 ml, 8.85 mmol) was added dropwise. After stirring at this temperature for 30 min, tert-butyl 2-cyano-6,6a,7,7a-tetrahydro-5H-cyclopropa[c][1,5]naphthyridine-5-carboxylate (300 mg, 1.106 mmol) in 1 ml THF solution was added. The reaction mixture was allowed to warm up to RT, stirred for 2 h before quenched with 50 mL of conc. NH$_4$OH (28-30%), and stirred 10 min at RT. The supernatant was decanted and the solid residue was washed 3 times with CH$_2$Cl$_2$. The combined organic layers were dried over MgSO$_4$ and concentrated under reduced pressure. The residue was purified by flash chromatography on silica gel with 0 to 100% MeOH in DCM to afford the title compound as an oil.

MS (ESI) m/z calc'd for C$_{17}$H$_{26}$N$_3$O$_2$ [M+H]$^+$, 304.41, found 304.30.

Step 2: tert-butyl 2-(2-(4-fluorobenzamido)propan-2-yl)-6,6a,7,7a-tetrahydro-5H-cyclopropa[c][1,5]naphthyridine-5-carboxylate

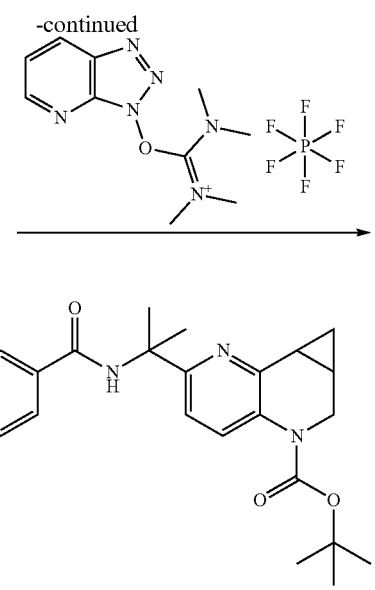

To a reaction vial was added 4-fluorobenzoic acid (84 mg, 0.602 mmol) and HATU (312 mg, 0.821 mmol), followed by DMF (2.000 ml). The mixture was stirred at RT for 5 min. Tert-butyl 2-(2-aminopropan-2-yl)-6,6a,7,7a-tetrahydro-5H-cyclopropa[c][1,5]naphthyridine-5-carboxylate (166 mg, 0.547 mmol) and DIEA (0.191 ml, 1.094 mmol) were added, after 5 min, the reaction mixture was diluted with EtOAc (5 ml) and water (5 ml). The organic layer was concentrated, purified on normal phase chromatography on silica gel with 0 to 100% EtOAc in hexane. The title compound was isolated as an oil.

MS (ESI) m/z calc'd for C$_{24}$H$_{29}$FN$_3$O$_3$ [M+H]$^+$ 426.21, found 426.3.

Step 3: 4-fluoro-N-(2-(6,6a,7,7a-tetrahydro-5H-cyclopropa[c][1,5]naphthyridin-2-yl)propan-2-yl)benzamide (Intermediate D)

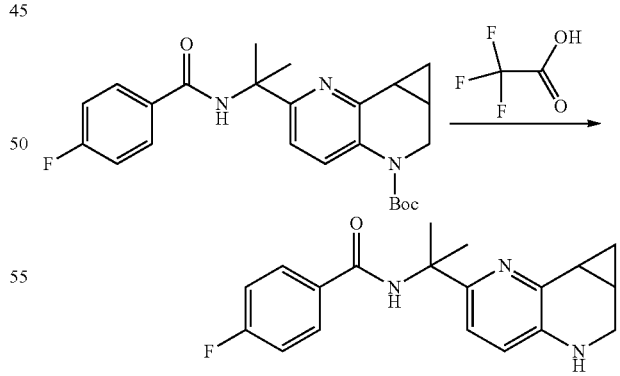

To a stirred solution of tert-butyl 2-(2-(4-fluorobenzamido)propan-2-yl)-6,6a,7,7a-tetrahydro-5H-cyclopropa[c][1,5]naphthyridine-5-carboxylate (180 mg, 0.423 mmol) in DCM (0.5 ml) was added TFA (0.815 ml, 10.58 mmol). The mixture was stirred at RT for 20 min, the solvent was then removed by rotovap, purified on normal phase chromatography on silica gel column with 0 to 100% EtOAC/

EtOH (3:1) and hexane. The title compound was isolated as a solid. MS (ESI) m/z calc'd for $C_{19}H_{21}FN_3O$ [M+H]$^+$ 326.16, found 326.2.

Step 4: 4-fluoro-N-(2-(5-(2-methylpyrimidin-4-yl)-6,6a,7,7a-tetrahydro-5H-cyclopropa[c][1,5]naphthyridin-2-yl)propan-2-yl)benzamide (Ex. 29)

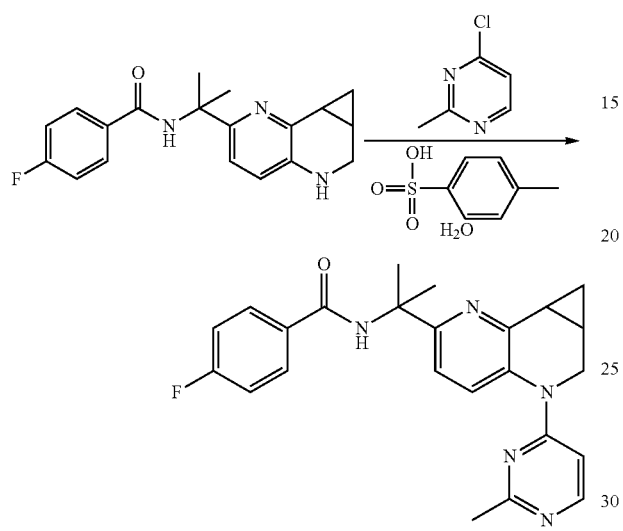

To a mixture of p-toluenesulfonic acid monohydrate (32.2 mg, 0.169 mmol), 4-chloro-2-methylpyrimidine (39.5 mg, 0.307 mmol), and 4-fluoro-N-(2-(6,6a,7,7a-tetrahydro-5H-cyclopropa[c][1,5]naphthyridin-2-yl)propan-2-yl)benzamide (50 mg, 0.154 mmol) was added N-methyl-2-pyrrolidinone (0.5 ml). The mixture was stirred at 80° C. for 7 h before cooled down to RT and diluted with EtOAc and water. The organic layer was concentrated, purified by normal phase chromatography on silica gel column with 0 to 100% EtOAc in hexane, and the resulting product was lyophilized to give the title compound a solid.

MS (ESI) m/z calc'd for $C_{24}H_{25}FN_5O$·TFA [M+H]$^+$ 418.2, found 418.2.

Step 5: 4-fluoro-N-(2-(((6aS,7aR)-5-(2-methylpyrimidin-4-yl)-6,6a,7,7a-tetrahydro-5H-cyclopropa[c][1,5]naphthyridin-2-yl)propan-2-yl)benzamide (Ex. 30 and Ex. 31)

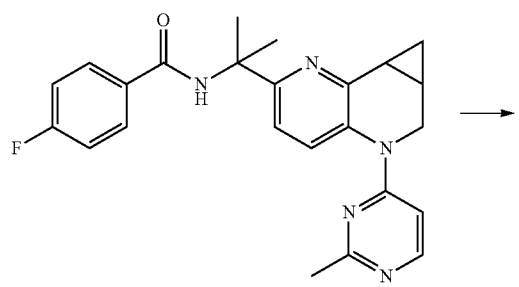

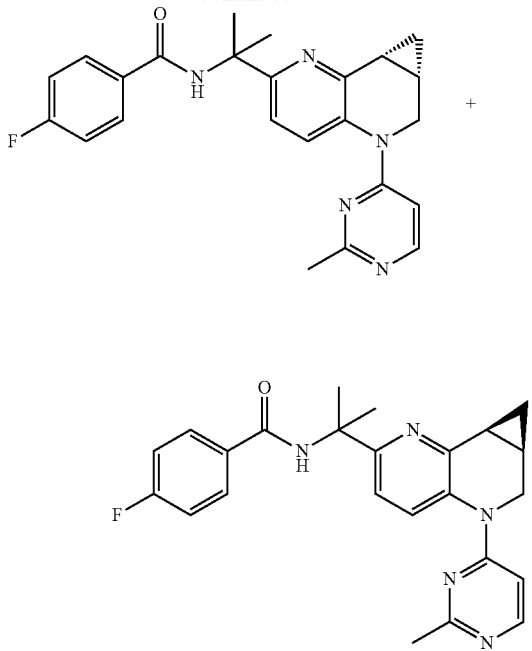

Example 29 was subjected to a chiral separation (chiral column: OD-H, co-solvent: IPA+0.1% DIPA) to give two isomers.

Example 30 (1$^{st}$ peak from chiral separation): MS (ESI) m/z calc'd for $C_{24}H_{25}FN_5O$·TFA [M+H]$^+$ 418.2, found 418.2.

$^1$H NMR (500 MHz, Chloroform-d) δ 8.71 (s, 1H), 8.41 (d, J=6.4 Hz, 1H), 8.05-7.88 (m, 1H), 7.79 (d, J=8.2 Hz, 1H), 7.51 (d, J=8.5 Hz, 1H), 7.16 (t, J=8.3 Hz, 1H), 6.92 (d, J=6.9 Hz, 1H), 5.46 (d, J=12.3 Hz, 1H), 3.22 (d, J=12.6 Hz, 1H), 2.80 (s, 2H), 2.71 (s, 1H), 2.36-2.15 (m, 1H), 1.95 (d, J=4.8 Hz, 6H), 1.49-1.34 (m, 1H), 1.28 (s, 3H), 1.01-0.78 (m, 1H).

Example 31 (2$^{nd}$ peak from chiral separation): MS (ESI) m/z calc'd for $C_{24}H_{25}FN_5O$·TFA [M+H]$^+$ 418.2, found 418.2.

$^1$H NMR (500 MHz, Chloroform-d) δ 8.71 (s, 1H), 8.41 (d, J=6.4 Hz, 1H), 8.05-7.88 (m, 1H), 7.79 (d, J=8.2 Hz, 1H), 7.51 (d, J=8.5 Hz, 1H), 7.16 (t, J=8.3 Hz, 1H), 6.92 (d, J=6.9 Hz, 1H), 5.46 (d, J=12.3 Hz, 1H), 3.22 (d, J=12.6 Hz, 1H), 2.80 (s, 2H), 2.71 (s, 1H), 2.36-2.15 (m, 1H), 1.95 (d, J=4.8 Hz, 6H), 1.49-1.34 (m, 1H), 1.28 (s, 3H), 1.01-0.78 (m, 1H).

Examples 32-34: cyclopropyl 2-(2-(4-fluorobenzamido)propan-2-yl)-6,6a,7,7a-tetrahydro-5H-cyclopropa[c][1,5]naphthyridine-5-carboxylate (Racemic, Isomer 1, and Isomer 2)

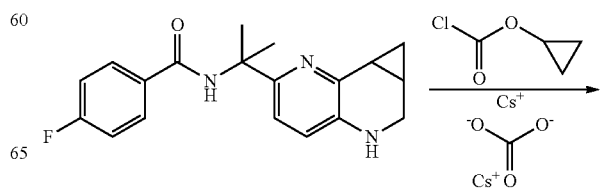

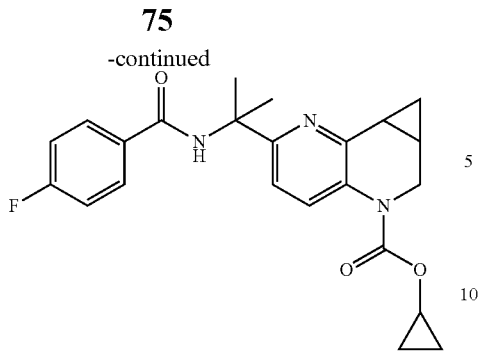

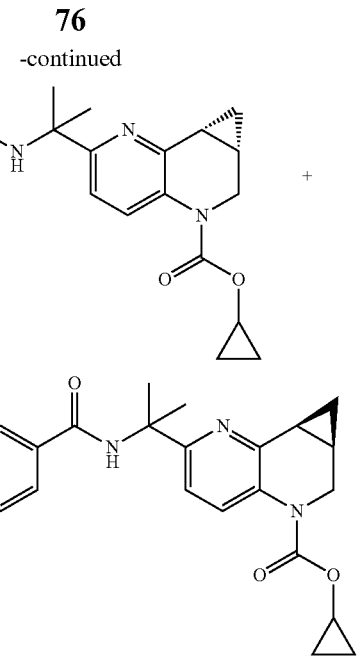

Step 1: cyclopropyl 2-(2-(4-fluorobenzamido)propan-2-yl)-6,6a,7,7a-tetrahydro-5H-cyclopropa[c][1,5]naphthyridine-5-carboxylate (Example 32)

To a stirred solution of 4-fluoro-N-(2-(6,6a,7,7a-tetrahydro-5H-yclopropa[c][1,5]naphthyridin-2-yl)propan-2-yl)benzamide (33 mg, 0.101 mmol) and $Cs_2CO_3$ (99 mg, 0.304 mmol) in $CH_2Cl_2$ (1 ml), was added cyclopropyl carbonochloridate (18.34 mg, 0.152 mmol). The mixture was stirred at RT for 30 min, then heated to 45° C. for another 20 min before filtered and rinsed with DCM (10 ml). The organic layer was concentrated, purified on reversed phase chromatography on C18 column with 10 to 100% ACN in water with 0.05% TFA. The resulting solid was isolated and lyophilized to give a racemic title compound (Ex. 24) as a solid. MS (ESI) m/z calc'd for $C_{23}H_{25}FN_3O_3$·TFA $[M+H]^+$ 410.18, found 410.2.

$^1$H NMR (500 MHz, Chloroform-d) δ 9.64 (s, 1H), 8.25 (s, 1H), 7.98 (dd, J=8.6, 5.4 Hz, 1H), 7.68-7.49 (m, 1H), 7.19-6.97 (m, 1H), 4.62 (d, J=13.1 Hz, 1H), 4.34-4.13 (m, 1H), 3.16-2.97 (m, 1H), 2.32 (d, J=6.3 Hz, 1H), 1.95 (s, 6H), 1.62-1.40 (m, 1H), 1.40-1.10 (m, 3H), 0.99-0.60 (m, 3H).

Step 2: cyclopropyl(6aS,7aR)-2-(2-(4-fluorobenzamido)propan-2-yl)-6,6a,7,7a-tetrahydro-5H-cyclopropa[c][1,5]naphthyridine-5-carboxylate (Ex. 33) and cyclopropyl(6aR,7aS)-2-(2-(4-fluorobenzamido)propan-2-yl)-6,6a,7,7a-tetrahydro-5H-cyclopropa[c][1,5]naphthyridine-5-carboxylate (Ex. 34)

The solid from Step 1 was resolved using chiral SFC column (chiral column: OD-H, co-solvent: IPA+0.1% DIPA) to give two enantiomers described below.

Example 33 (1st peak from chiral separation): cyclopropyl(6aS,7aR)-2-(2-(4-fluorobenzamido)propan-2-yl)-6,6a,7,7a-tetrahydro-5H-cyclopropa[c][1,5]naphthyridine-5-carboxylate Example 34 (2nd peak from chiral separation): cyclopropyl(6aR,7aS)-2-(2-(4-fluorobenzamido)propan-2-yl)-6,6a,7,7a-tetrahydro-5H-cyclopropa[c][1,5]naphthyridine-5-carboxylate Example 35: 2-(2-(4-fluorobenzamido)propan-2-yl)-5-(2,2,2-trifluoroacetyl)-6,6a,7,7a-tetrahydro-5H-cyclopropa[c][1,5]naphthyridin-1-ium

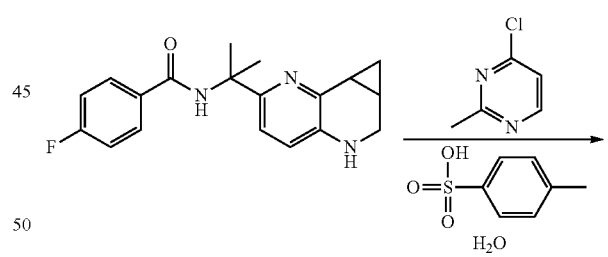

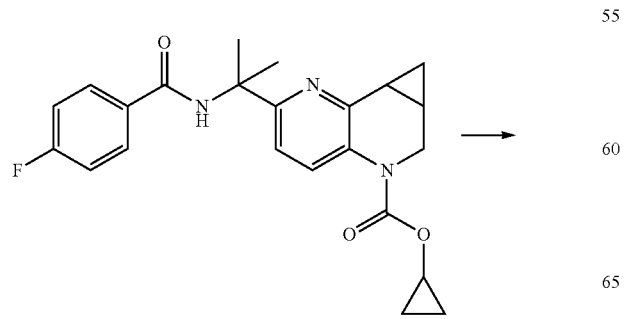

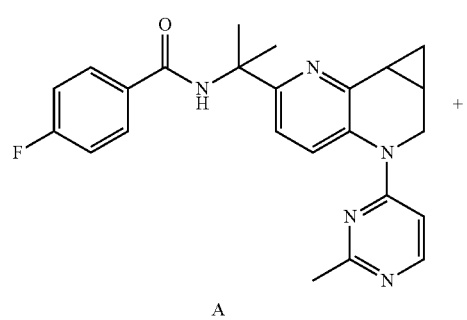

A

-continued

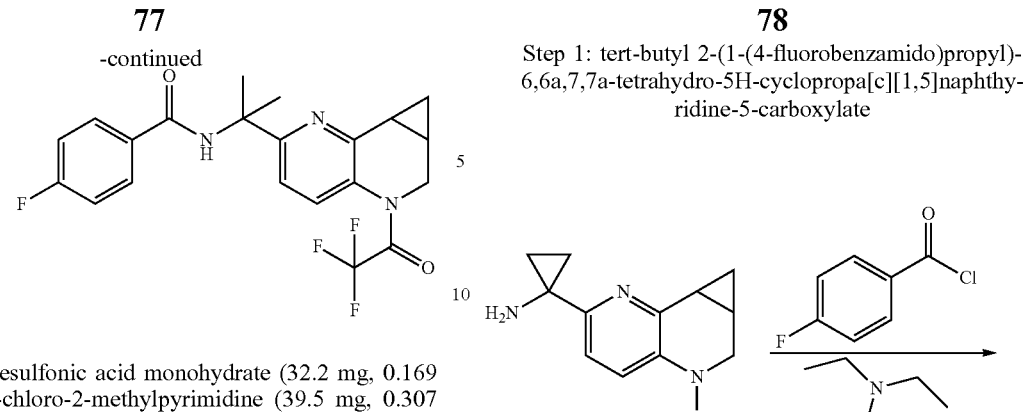

To p-toluenesulfonic acid monohydrate (32.2 mg, 0.169 mmol) and 4-chloro-2-methylpyrimidine (39.5 mg, 0.307 mmol) in a vial were added 4-fluoro-N-(2-(6,6a,7,7a-tetrahydro-5H-cyclopropa[c][1,5]naphthyridin-2-yl)propan-2-yl)benzamide (50 mg, 0.154 mmol) and N-methyl-2-pyrrolidinone (0.5 ml). The mixture was stirred at 80° C. for 7 h. LCMS showed small amount of product A and major product Ex. 27. The mixture was diluted with EtOAc and water, the organic layer was concentrated, and purified on a 12 g normal phase ISCO column with 0 to 100% EtOAc in hexane. Excess solvent was removed in-vacuo and the solids obtained were lyophilized to give the title compound.

MS (ESI) m/z calc'd for $C_{21}H_{20}F_4N_3O_2 \cdot TFA$ [M+H]$^+$ 422.2, found 422.3.

Examples 36-37: cyclopropyl 2-(1-(4-fluorobenzamido)propyl)-6,6a,7,7a-tetrahydro-5H-cyclopropa[c][1,5]naphthyridine-5-carboxylate (Racemic, Isomer 1 and Isomer 2)

Step 1: tert-butyl 2-(1-(4-fluorobenzamido)propyl)-6,6a,7,7a-tetrahydro-5H-cyclopropa[c][1,5]naphthyridine-5-carboxylate

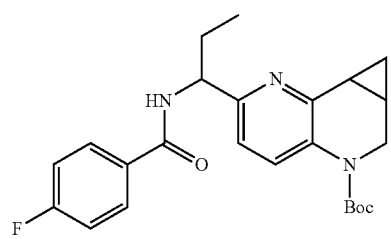

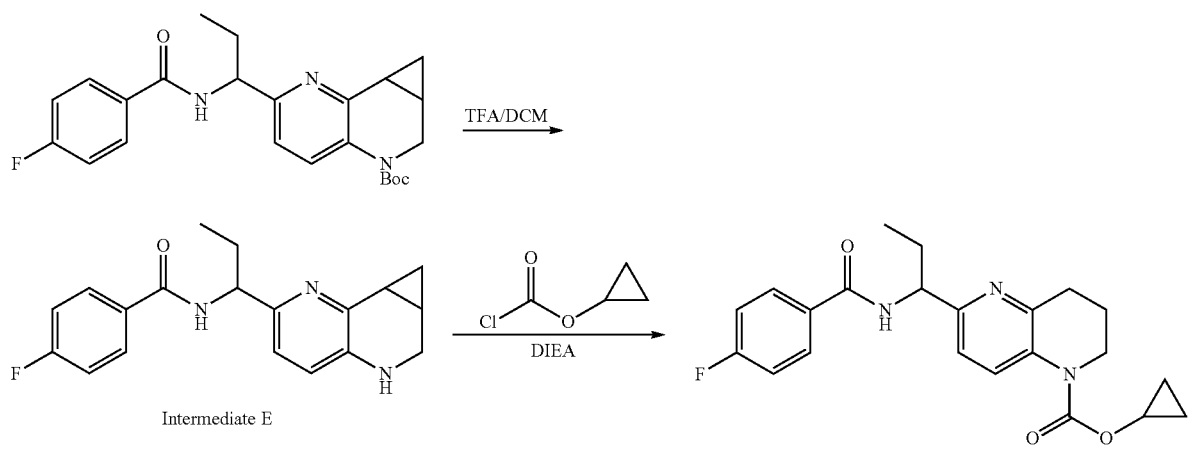

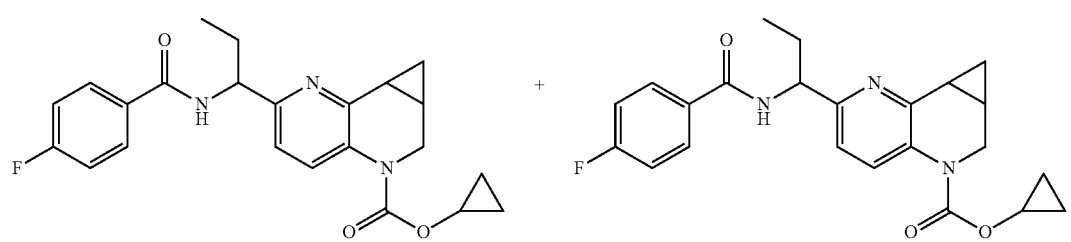

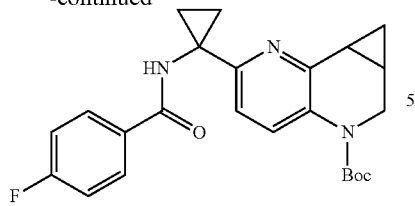

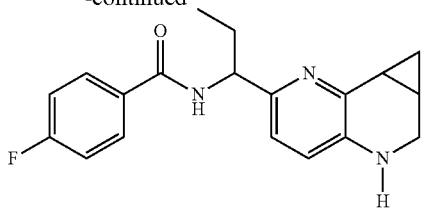

Intermediate E

To a stirred solution of tert-butyl 2-(1-aminocyclopropyl)-6,6a,7,7a-tetrahydro-5H-cyclopropa[c][1,5]naphthyridine-5-carboxylate (50.0, 148 mmol) in dichloromethane (500 mL) at RT was added triethylamine (62 mL, 445 mmol). The reaction was cooled with an ice/water bath for 15 min. A solution of 4-fluorobenzoyl chloride (18.36 mL, 155 mmol) in dichloromethane (100 mL) was added dropwise using an addition funnel on the flask. The reaction was quenched after 1.5 h with sat. aq. NaHCO$_3$(250 mL) solution. The biphasic mixture was transferred to a separatory funnel and extracted with dichloromethane (200 mL). The organic extracts were combined and dried over anhydrous Na$_2$SO$_4$. Solids were filtered off from the mixture. The filtrate was concentrated to dryness on a rotovap and the resulting solid was redissolved in DCM and purified on a silica gel column using gradient elution with ethyl acetate in hexanes in 2 portions. The product was concentrated to a small bulk and the resulting suspension (a thick slurry) from above was then triturated with DCM first, and then solvent-exchanged to hexanes. This resulted in a thick suspension. The solid obtained was isolated by filtration, and the filtrate cake was washed with hexanes. The cake obtained was air dried, the filtrate obtained was re-purified on a silica gel column using gradient elution with ethyl acetate/hexane. In addition to the expected cyclopropyl product, the ethyl isomer was also obtained. MS (ESI) m/z calc'd for C$_{24}$H$_{29}$FN$_3$O$_3$ [M+H]$^+$ 426.2, found 426.1.

Step 2: 4-fluoro-N-(1-(6,6a,7,7a-tetrahydro-5H-cyclopropa[c][1,5]naphthyridin-2-yl)propyl)benzamide (Intermediate E)

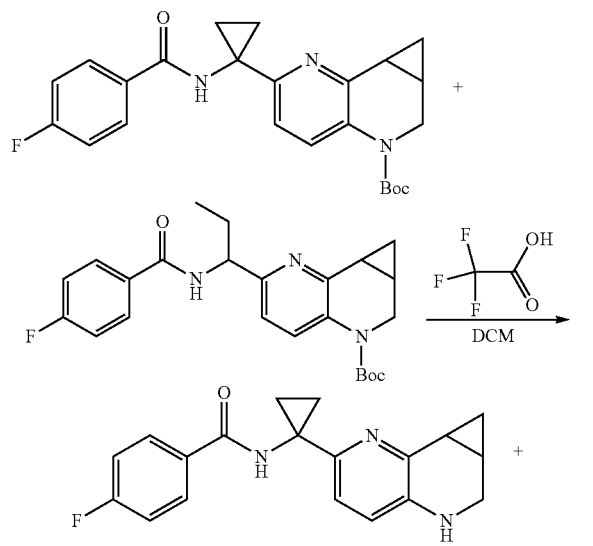

To a reaction vial were added tert-butyl 2-(1-(4-fluorobenzamido)cyclopropyl)-6,6a,7,7a-tetrahydro-5H-cyclopropa[c][1,5]naphthyridine-5-carboxylate (520 mg, 1.228 mmol), DCM (0.5 ml), and TFA (2.365 ml, 30.7 mmol). The mixture was stirred at RT for 20 min and LCMS showed completion. Solvent was removed by rotovap and purified on 24 g normal phase ISCO column with 0 to 100% EtOAC/EtOH (3:1) in hexane. The resulting product was isolated as an oil. The title compound was obtained as a mixture with 4-fluoro-N-(1-(6,6a,7,7a-tetrahydro-5H-cyclopropa[c][1,5]naphthyridin-2-yl)cyclopropyl)benzamide along with 4-fluoro-N-(1-(6,6a,7,7a-tetrahydro-5H-cyclopropa[c][1,5]naphthyridin-2-yl)cyclopropyl)benzamide.

Step 3: cyclopropyl 2-(1-(4-fluorobenzamido)propyl)-6,6a,7,7a-tetrahydro-5H-cyclopropa[c][1,5]naphthyridine-5-carboxylate

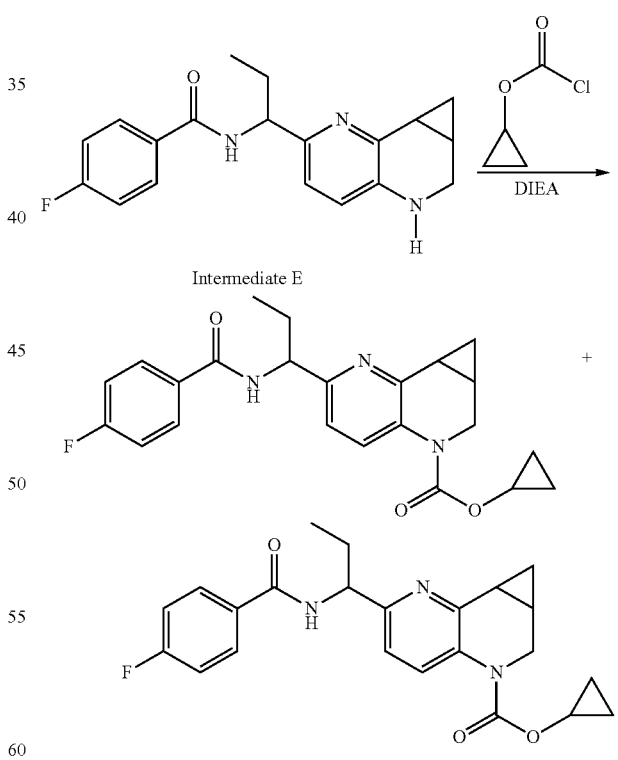

To the stirred solution of Intermediate E in CH$_2$Cl$_2$ (3414 μl) were added TEA (381 μl, 2.73 mmol) and cyclopropyl chloroformate (107 mg, 0.888 mmol) at 0° C., followed by addition of DMAP (16.68 mg, 0.137 mmol). The mixture was stirred at RT for 5 h. LCMS check showed only half of the starting material was consumed. To this mixture was added more cyclopropyl chloroformate (50 mg, 0.4141 mmol). The mixture was left stirring at RT over the weekend. LCMS check showed desired product as the major product. The mixture was concentrated, and re-dissolved in DMSO and purified by reversed phase HPLC using the following conditions (Reverse HPLC on a 19×100 mm, Waters CSH C18 column, 5μ particle size, flow rate 25 ml/min, linear gradient, 10% ACN/water to 45 ACN/water, total run time 15 min, buffering with 0.16% TFA; multiple injections) to afford the title compound as a solid.

MS (ESI) m/z calc'd for $C_{23}H_{25}FN_3O_3$·TFA $[M+H]^+$ 410.18, found 410.3.

Step 4: Chiral SFC Resolution

The compound from step 3, cyclopropyl 2-(1-(4-fluorobenzamido)propyl)-6,6a,7,7a-tetrahydro-5H-cyclopropa[c][1,5]naphthyridine-5-carboxylate, TFA (180 mg, 0.344 mmol)) was resolved by chiral SFC separation using the following conditions to give two fractions with desired mass as solids after concentration in vacuo:

Injection Volume: 1.0 ml; Co-Solvent: 30% (MeOH); UV Wavelength: 210 nm

Concentration: 180 mg in 30 ml MeOH; Column: OJ-H, 21×250 mm

Example 36 (Isomer 1, Peak 1)

MS (ESI) m/z calc'd for $C_{23}H_{25}FN_3O_3$·TFA $[M+H]^+$ 410.18, found 410.32.
$^1$H NMR (500 MHz, $CD_3OD$): 7.95-7.92 (m, 2H); 7.71-7.61 (m, 1H); 7.23-7.20 (m, 3H); 5.05-5.01 (m, 1H); 4.55-4.52 (m, 1H); 4.15-4.11 (m, 1H); 3.00-2.98 (m, 1H); 2.32-2.27 (m, 1H); 2.10-1.89 (m, 3H); 1.22-1.18 (m, 1H); 1.03-1.24 (t, J=7.4 Hz, 3H); 0.82-0.78 (m, 1H); 0.73-0.70 (m, 4H)

Example 37 (Isomer 2, Peak 2)

MS (ESI) m/z calc'd for $C_{23}H_{25}FN_3O_3$·TFA $[M+H]^+$ 410.18, found 410.32.
$^1$H NMR (500 MHz, $CD_3OD$): 7.95-7.92 (m, 2H); 7.71-7.61 (m, 1H); 7.23-7.20 (m, 3H); 7.12-7.11 (m, 1H); 5.05-5.01 (m, 1H); 4.55-4.52 (m, 1H); 4.15-4.11 (m, 1H); 3.00-2.98 (m, 1H); 2.32-2.27 (m, 1H); 2.10-1.89 (m, 3H); 1.22-1.18 (m, 1H); 1.03-1.24 (t, J=7.4 Hz, 3H); 0.82-0.78 (m, 1H); 0.73-0.70 (m, 4H)

Racemic compounds in the following table were prepared in a similar manner as Examples 36-37.

Examples 39-46: 4-fluoro-N-(2-methyl-1-(5-(2-methylpyrimidin-4-yl)-6,6a,7,7a-tetrahydro-5H-cyclopropa[c][1,5]naphthyridin-2-yl)cyclopropyl)benzamide (8 Isomers)

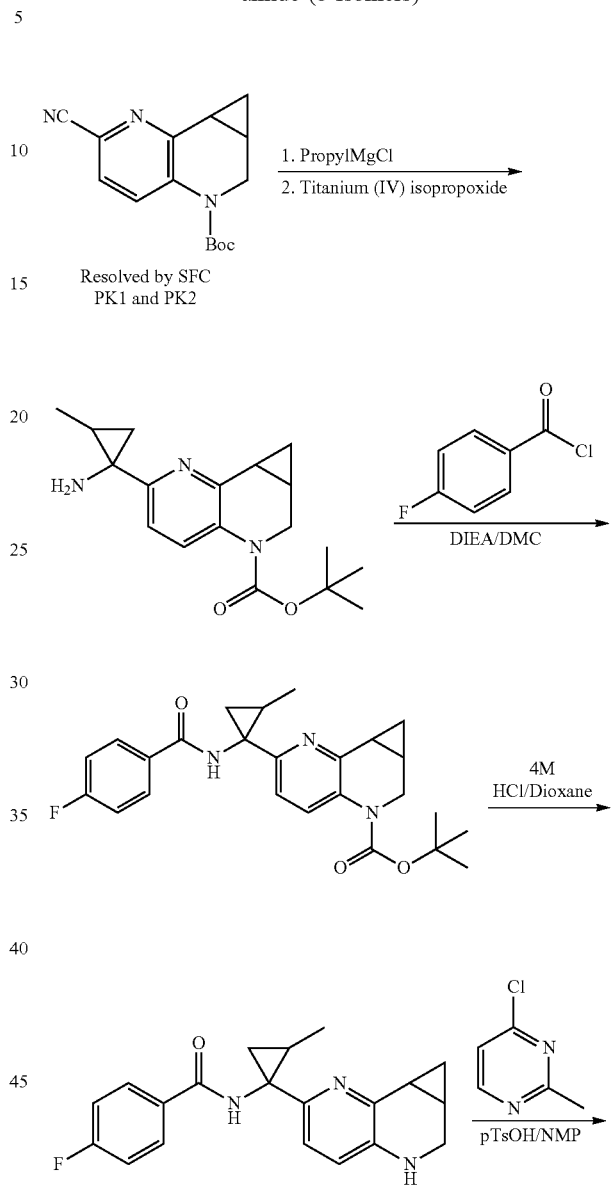

Resolved by SFC PK1 and PK2

| Ex. # | Structure | Chemical Name | Mass [M + H]+ |
|---|---|---|---|
| 38 | ![structure] | 4-fluoro-N-(1-(5-(2-methyl-pyrimidin-4-yl)-6,6a,7,7a-tetrahydro-5H-cyclopropa[c]-[1,5]naphthyridin-2-yl)propyl)-benzamide | 407.02 |

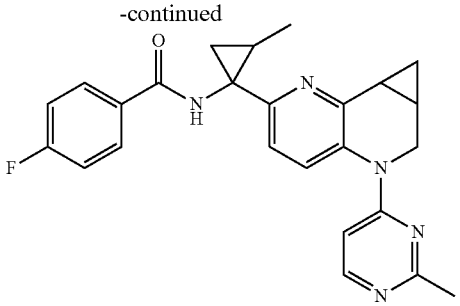

The starting nitrile compound was chirally resolved to give Peak 1 and Peak 2 for further steps. Examples 39-42 were prepared from Peak 1 following steps 1-4 described below.

Step 1: tert-butyl 2-(1-amino-2-methylcyclopropyl)-6,6a,7,7a-tetrahydro-5H-cyclopropa[c][1,5]naphthyridine-5-carboxylate

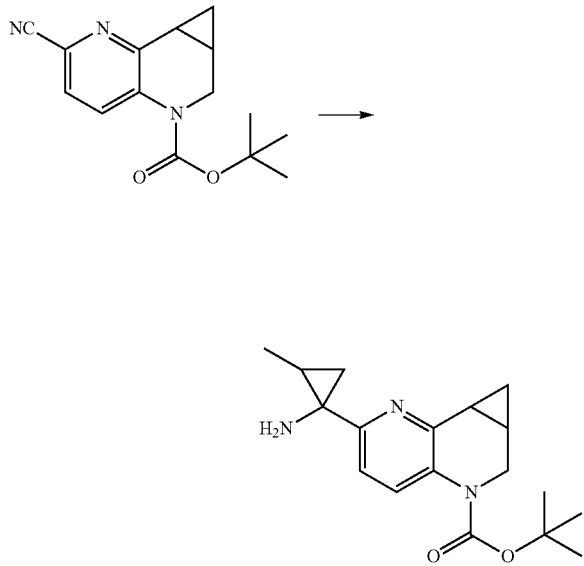

To a flask that was thoroughly purged with nitrogen and vacuum three times, a solution of tert-butyl 2-cyano-6,6a,7,7a-tetrahydro-5H-cyclopropa[c][1,5]naphthyridine-5-carboxylate (734.00 mg, 2.71 mmol) in THF (3.00 mL) was added. This was cooled to −78° C. and Titanium (IV) isopropoxide (1.602 mL, 5.41 mmol) was added and allowed to stir for 15 mins. To this stirred solution, propylmagnesium chloride (3.25 mL, 6.49 mmol) and added and allowed to warm to room temp and stirred overnight. This was quenched with 1:1 aq. 1N NaOH soln. Excess EtOAc was added. The organic layer was decanted, dried over MgSO4, filtered, and excess solvent was removed under reduced pressure. The oily solid obtained was used for the next step directly. Tert-butyl 2-(1-amino-2-methylcyclopropyl)-6,6a,7,7a-tetrahydro-5H-cyclopropa[c][1,5]naphthyridine-5-carboxylate was obtained as a solid.

MS ESI calcd. for $C_{18}H_{26}N_3O_2$ [M+H]$^+$ 316.19, found 316.2.

Step 2: tert-butyl 2-((1R,2R)-1-(4-fluorobenzamido)-2-methylcyclopropyl)-6,6a,7,7a-tetrahydro-5H-cyclopropa[c][1,5]naphthyridine-5-carboxylate

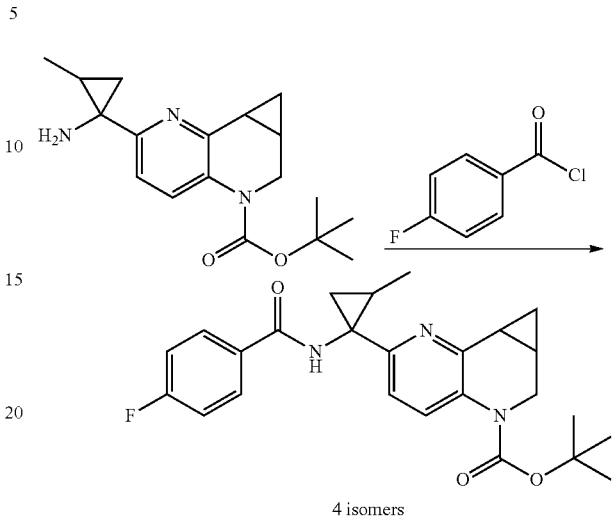

To a solution of tert-butyl 2-(1-amino-2-methylcyclopropyl)-6,6a,7,7a-tetrahydro-5H-cyclopropa[c][1,5]naphthyridine-5-carboxylate (868.00 mg, 2.75 mmol) in DCM (5.00 ml) at 0° C., were added DIEA (1.442 ml, 8.26 mmol) and 4-fluorobenzoyl chloride (0.358 ml, 3.03 mmol). The mixture was stirred at 0° C. for 1 h with an approximately 85% conversion. The mixture was diluted with sat. NaHCO3, and extracted with EtOAc. The organic layer was separated, washed with brine, dried over MgSO4, filtered, and concentrated. The residue was purified by flash chromatography (0-50% EtOAc/hexanes). Appropriate fractions were pooled together, excess solvent was removed under reduced pressure, and vacuum dried to give a solid. The solid was separated on chiral SFC to give 4 isomers.

First peak: MS ESI calcd. for $C_{25}H_{29}FN_3O_3$ [M+H]$^+$ 438.21, found 438.2.

$^1$H NMR (499 MHz, DMSO-d$_6$) δ 9.30 (s, 1H), 7.97 (d, J=8.8 Hz, 2H), 7.53 (d, J=8.5 Hz, 1H), 7.39-7.15 (m, 3H), 4.41 (d, J=12.8 Hz, 1H), 2.89 (d, J=13.9 Hz, 1H), 2.14 (d, J=21.2 Hz, 1H), 2.05-1.97 (m, 1H), 1.84-1.74 (m, 1H), 1.65-1.54 (m, 1H), 1.40 (s, 9H), 1.19-1.08 (m, 2H), 0.98 (s, 3H), 0.67-0.56 (m, 1H).

Second Peak:
1H NMR (499 MHz, DMSO-d6) δ 9.30 (s, 1H), 8.06-7.89 (m, 2H), 7.55 (d, J=8.5 Hz, 1H), 7.36-7.22 (m, 3H), 4.41 (d, J=12.7 Hz, 1H), 2.93-2.80 (m, 1H), 2.21-2.11 (m, 1H), 2.11-2.01 (m, 1H), 1.83-1.74 (m, 1H), 1.66-1.56 (m, 1H), 1.42 (s, 10H), 1.16-1.06 (m, 2H), 0.99 (d, J=6.3 Hz, 3H), 0.66-0.57 (m, 1H).

MS ESI calcd. for $C_{25}H_{29}FN_3O_3$ [M+H]$^+$ 438.21, found 438.2.

Third peak: MS ESI calcd. for $C_{25}H_{29}FN_3O_3$ [M+H]$^+$ 438.21, found 438.2.

1H NMR (499 MHz, DMSO-d6) δ 9.30 (s, 1H), 8.06-7.89 (m, 2H), 7.55 (d, J=8.5 Hz, 1H), 7.36-7.22 (m, 3H), 4.41 (d, J=12.7 Hz, 1H), 2.93-2.80 (m, 1H), 2.21-2.11 (m, 1H), 2.11-2.01 (m, 1H), 1.83-1.74 (m, 1H), 1.66-1.56 (m, 1H), 1.42 (s, 10H), 1.16-1.06 (m, 2H), 0.99 (d, J=6.3 Hz, 3H), 0.66-0.57 (m, 1H).

Fourth peak: MS ESI calcd. for $C_{25}H_{29}FN_3O_3$ [M+H]$^+$ 438.21, found 438.2.

¹H NMR (499 MHz, DMSO-d₆) δ 9.30 (s, 1H), 7.97 (d, J=8.8 Hz, 2H), 7.53 (d, J=8.5 Hz, 1H), 7.39-7.15 (m, 3H), 4.41 (d, J=12.8 Hz, 1H), 2.89 (d, J=13.9 Hz, 1H), 2.14 (d, J=21.2 Hz, 1H), 2.05-1.97 (m, 1H), 1.84-1.74 (m, 1H), 1.65-1.54 (m, 1H), 1.40 (s, 9H), 1.19-1.08 (m, 2H), 0.98 (s, 3H), 0.67-0.56 (m, 1H).

All four isomers were individually deprotected using the procedure below.

Step 3: 4-fluoro-N-(2-methyl-1-(6,6a,7,7a-tetrahydro-5H-cyclopropa[c][1,5]naphthyridin-2-yl)cyclopropyl)benzamide

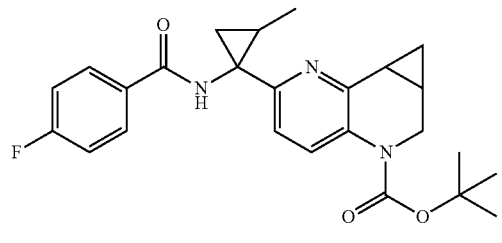

To a solution of tert-butyl 2-(1-(4-fluorobenzamido)-2-methylcyclopropyl)-6,6a,7,7a-tetrahydro-5H-cyclopropa[c][1,5]naphthyridine-5-carboxylate) (102.00 mg, 0.233 mmol) in DCM (5.00 ml) at 0° C., HCl gas or hydrochloric acid (0.291 ml, 1.166 mmol) was added. This was allowed to stir at 0° C. for 1 h, then stirred at RT. The mixture was diluted with excess DCM and concentrated. This was partitioned into ethyl acetate and aq. NaOH solution. The aq. layer was extracted twice, the organic layers were pooled together, washed with brine, dried over MgSO₄, filtered, and excess solvent was removed under reduced pressure and vacuum dried to give the free base as a solid.

Isomer 1: MS ESI calcd. for C₂₀H₂₁FN₃O [M+H]⁺ 338.16, found 338.1.

Isomer 2: MS ESI calcd. for C₂₀H₂₁FN₃O [M+H]⁺ 338.16, found 338.1.

Isomer 3: MS ESI calcd. for C₂₀H₂₁FN₃O [M+H]⁺ 338.1, found 338.1.

Isomer 4: MS ESI calcd. for C₂₀H₂₁FN₃O [M+H]⁺ 338.1, found 338.1.

All the 4 isomers were individually carried forward using the same procedure below to give the diastereomers.

Step 4: 4-fluoro-N-(2-methyl-1-(5-(2-methylpyrimidin-4-yl)-6,6a,7,7a-tetrahydro-5H-cyclopropa[c][1,5]naphthyridin-2-yl)cyclopropyl)benzamide (Examples 39-42)

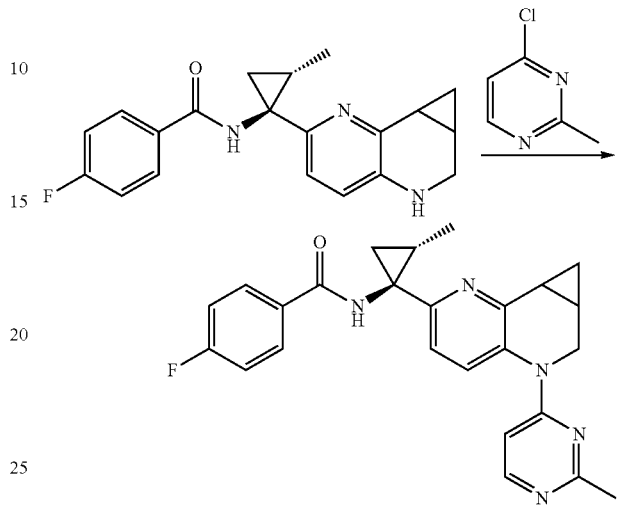

To a vial containing 4-fluoro-N-((1S,2S)-2-methyl-1-(6,6a,7,7a-tetrahydro-5H-cyclopropa[c][1,5]naphthyridin-2-yl)cyclopropyl)benzamide (72.00 mg, 0.213 mmol), 4-chloro-2-methylpyrimidine (54.9 mg, 0.427 mmol), and 4-methylbenzenesulfonic acid (36.7 mg, 0.213 mmol) was added NMP (1 mL). The mixture was allowed to stir at 65° C. for 24 h. The mixture was neutralized with sat. NaHCO₃, and extracted with ethyl acetate. The combined organics were washed with water and brine, dried over MgSO₄, filtered, and concentrated.

The residue was purified on a silica gel column using 20-80% (Hex-1:3EtOH/EtOAc)/mixture). Appropriate fractions were pooled together, excess solvent was removed under reduced pressure, and the remaining material was vacuum dried to give 4 isomers of the title compounds as solids. Absolute stereochemistry was not determined.

Isomer 1

¹H NMR (499 MHz, DMSO-d₆) δ 9.34 (s, 1H), 8.12 (d, J=6.1 Hz, 1H), 8.09-7.95 (m, 2H), 7.61 (d, J=8.4 Hz, 1H), 7.37-7.25 (m, 3H), 6.64 (d, J=6.1 Hz, 1H), 5.12 (d, J=12.8 Hz, 1H), 2.96 (d, J=12.7 Hz, 1H), 2.43 (s, 3H), 2.26-2.15 (m, 1H), 2.13-2.03 (m, 1H), 1.87-1.81 (m, 1H), 1.69-1.58 (m, 1H), 1.22-1.13 (m, 1H), 1.13-1.05 (m, 1H), 1.02 (d, J=6.3 Hz, 3H), 0.65-0.51 (m, 1H).

Isomer 2

¹H NMR (499 MHz, DMSO-d₆) δ 9.05 (s, 1H), 8.11 (d, J=6.1 Hz, 1H), 8.06-7.96 (m, 2H), 7.56 (d, J=8.4 Hz, 1H), 7.34 (t, J=8.9 Hz, 2H), 7.10 (d, J=8.4 Hz, 1H), 6.63 (d, J=6.1 Hz, 1H), 5.12 (d, J=13.1 Hz, 1H), 3.31 (s, 1H), 2.43 (s, 3H), 2.19-2.11 (m, 2H), 2.03-1.93 (m, 1H), 1.96-1.86 (m, 1H), 1.64-1.54 (m, 1H), 1.19 (d, J=6.2 Hz, 2H), 1.10-0.96 (m, 2H), 0.61-0.51 (m, 1H).

Isomer 3

¹H NMR (499 MHz, DMSO-d₆) δ 9.05 (s, 1H), 8.13 (d, J=6.1 Hz, 1H), 8.04 (d, J=5.5 Hz, 2H), 7.55 (d, J=8.4 Hz, 1H), 7.35 (t, J=8.9 Hz, 2H), 7.10 (d, J=8.4 Hz, 1H), 6.62 (d, J=6.1 Hz, 1H), 5.11 (d, J=12.5 Hz, 1H), 3.30 (d, J=7.2 Hz, 1H), 2.70 (s, 1H), 2.43 (s, 3H), 2.22-2.10 (m, 2H), 2.04 (d,

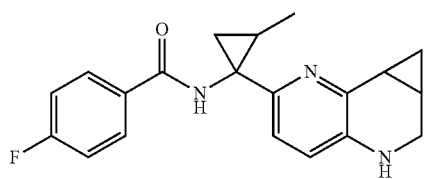

J=25.2 Hz, 1H), 1.89 (d, J=29.0 Hz, 1H), 1.24 (s, 2H), 1.19 (d, J=6.2 Hz, 1H), 1.10-0.94 (m, 1H), 0.62-0.49 (m, 1H).

Isomer 4

$^1$H NMR (499 MHz, DMSO-d$_6$) δ 9.33 (s, 1H), 8.25-8.05 (m, 1H), 8.05-7.90 (m, 2H), 7.62 (d, J=8.4 Hz, 1H), 7.40-7.25 (m, 3H), 6.66 (d, J=6.1 Hz, 1H), 5.12 (d, J=12.5 Hz, 1H), 3.32-3.27 (m, 2H), 2.93 (d, J=12.8 Hz, 1H), 2.44 (s, 3H), 2.20-2.13 (m, 1H), 2.13-2.07 (m, 1H), 1.96-1.87 (m, 1H), 1.87-1.75 (m, 1H), 1.72-1.59 (m, 1H), 1.19-1.13 (m, 1H), 1.03 (d, J=6.2 Hz, 3H), 0.59-0.50 (m, 1H).

1H), 7.31 (d, J=19.1 Hz, 3H), 6.64 (d, J=6.1 Hz, 1H), 5.12 (d, J=13.8 Hz, 1H), 2.95 (d, J=16.1 Hz, 1H), 2.43 (s, 4H), 2.28-2.15 (m, 1H), 2.15-2.04 (m, 1H), 1.89-1.78 (m, 1H), 1.70-1.58 (m, 1H), 1.27-1.12 (m, 1H), 1.12-1.04 (m, 1H), 1.02 (d, J=6.3 Hz, 3H), 0.63-0.50 (m, 1H).

Isomer 2

$^1$H NMR (499 MHz, DMSO-d$_6$) δ 9.33 (s, 1H), 8.25-8.05 (m, 1H), 8.05-7.90 (m, 2H), 7.62 (d, J=8.4 Hz, 1H), 7.40-

| Ex. # | Structure | Chemical Name | Mass [M + H]+ |
|---|---|---|---|
| 39 | 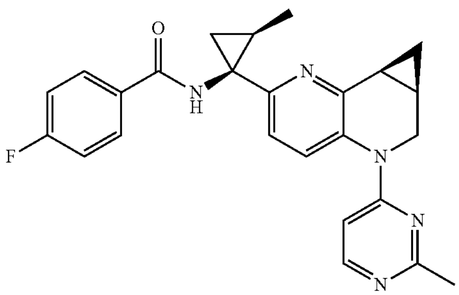 [SMILES: Cc1nccc(N2C[C@@H]3C[C@@H]3c3nc([C@]4(NC(=O)c5ccc(F)cc5)C[C@H]4C)ccc32)n1] | 4-fluoro-N-((1S,2R)-2-methyl-1-((6aR,7aS)-5-(2-methyl-pyrimidin-4-yl)-6,6a,7,7a-tetra-hydro-5H-cyclopropa[c][1,5]-naphthyridin-2-yl)cyclopropyl)-benzamide | 430.2 |
| 40 | 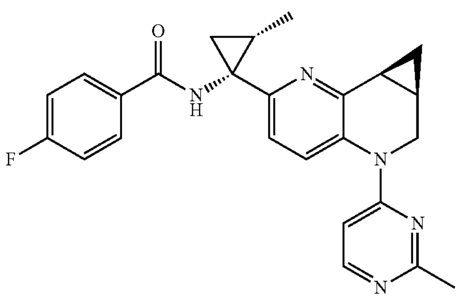 [SMILES: Cc1nccc(N2C[C@@H]3C[C@@H]3c3nc([C@@]4(NC(=O)c5ccc(F)cc5)C[C@@H]4C)ccc32)n1] | 4-fluoro-N-((1R,2S)-2-methyl-1-((6aR,7aS)-5-(2-methyl-pyrimidin-4-yl)-6,6a,7,7a-tetra-hydro-5H-cyclopropa[c][1,5]-naphthyridin-2-yl)cyclopropyl)-benzamide | 430.2 |
| 41 | 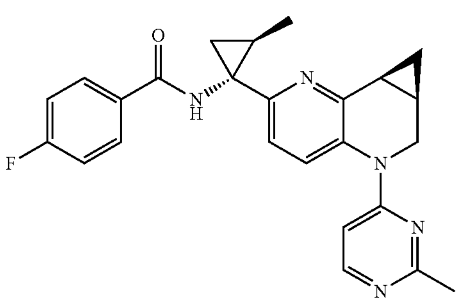 [SMILES: Cc1nccc(N2C[C@@H]3C[C@@H]3c3nc([C@@]4(NC(=O)c5ccc(F)cc5)C[C@H]4C)ccc32)n1] | 4-fluoro-N-((1R,2R)-2-methyl-1-((6aR,7aS)-5-(2-methyl-pyrimidin-4-yl)-6,6a,7,7a-tetra-hydro-5H-cyclopropa[c][1,5]-naphthyridin-2-yl)cyclopropyl)-benzamide | 430.2 |
| 42 | 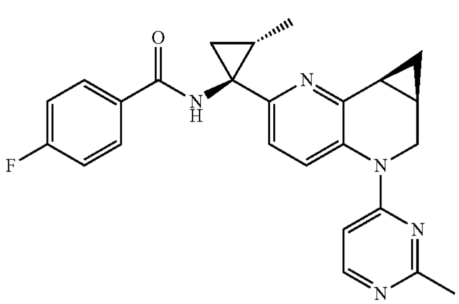 [SMILES: Cc1nccc(N2C[C@@H]3C[C@@H]3c3nc([C@]4(NC(=O)c5ccc(F)cc5)C[C@@H]4C)ccc32)n1] | 4-fluoro-N-((1S,2S)-2-methyl-1-((6aR,7aS)-5-(2-methyl-pyrimidin-4-yl)-6,6a,7,7a-tetra-hydro-5H-cyclopropa[c][1,5]-naphthyridin-2-yl)cyclopropyl)-benzamide | 430.2 |

Examples 43-46 were prepared from Peak 2 similarly following steps 1~4 described above.

Isomer 1

$^1$H NMR (499 MHz, DMSO-d$_6$) δ 9.34 (s, 1H), 8.12 (d, J=6.1 Hz, 1H), 7.99 (d, J=14.4 Hz, 2H), 7.61 (d, J=8.4 Hz, 1H), 7.25 (m, 3H), 6.66 (d, J=6.1 Hz, 1H), 5.12 (d, J=12.5 Hz, 1H), 3.32-3.27 (m, 2H), 2.93 (d, J=12.8 Hz, 1H), 2.44 (s, 3H), 2.20-2.13 (m, 1H), 2.13-2.07 (m, 1H), 1.96-1.87 (m, 1H), 1.87-1.75 (m, 1H), 1.72-1.59 (m, 1H), 1.19-1.13 (m, 1H), 1.03 (d, J=6.2 Hz, 3H), 0.59-0.50 (m, 1H).

Isomer 3

¹H NMR (499 MHz, DMSO-d₆) δ 9.34 (s, 1H), 8.12 (d, J=6.1 Hz, 1H), 8.04-7.92 (m, 2H), 7.61 (d, J=8.4 Hz, 1H), 7.39-7.24 (m, 3H), 6.64 (d, J=6.1 Hz, 1H), 5.12 (d, J=14.2 Hz, 1H), 2.97-2.91 (m, 1H), 2.43 (s, 3H), 2.26-2.15 (m, 1H), 2.15-2.04 (m, 1H), 1.88-1.79 (m, 1H), 1.68-1.56 (m, 1H), 1.21-1.13 (m, 1H), 1.10-1.04 (m, 1H), 1.02 (d, J=6.3 Hz, 3H), 0.62-0.49 (m, 1H).

Isomer 4

¹H NMR (499 MHz, DMSO-d₆) δ 9.34 (s, 1H), 8.12 (d, J=6.1 Hz, 1H), 7.99 (d, J=14.4 Hz, 2H), 7.61 (d, J=8.4 Hz, 1H), 7.41-7.20 (m, 3H), 6.64 (d, J=6.1 Hz, 1H), 5.12 (d, J=12.9 Hz, 1H), 2.96 (d, J=13.1 Hz, 1H), 2.43 (s, 3H), 2.24-2.14 (m, 1H), 2.14-2.02 (m, 1H), 1.91-1.77 (m, 1H), 1.71-1.57 (m, 1H), 1.25-1.11 (m, 1H), 1.13-1.04 (m, 1H), 1.02 (d, J=6.3 Hz, 4H), 0.63-0.53 (m, 1H).

| Ex. # | Structure | Chemical Name | Mass [M + H]+ |
|---|---|---|---|
| 43 | 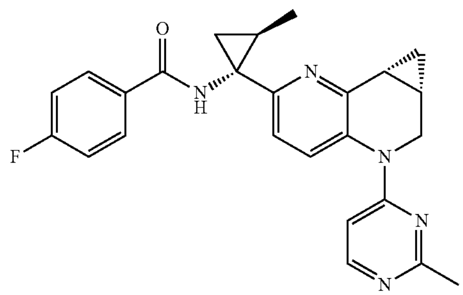 [SMILES: Cc1nccc(N2C[C@H]3C[C@H]3c3nc([C@@]4(NC(=O)c5ccc(F)cc5)C[C@H]4C)ccc32)n1] | 4-fluoro-N-((1R,2R)-2-methyl-1-((6aS,7aR)-5-(2-methyl-pyrimidin-4-yl)-6,6a,7,7a-tetra-hydro-5H-cyclopropa[c][1,5]-naphthyridin-2-yl)cyclopropyl)-benzamide | 430.2 |
| 44 | 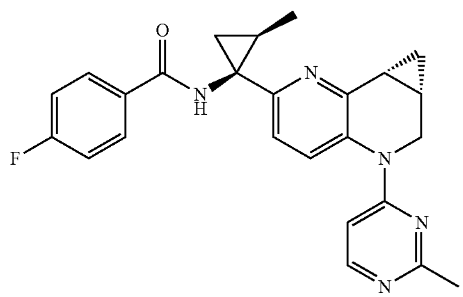 [SMILES: Cc1nccc(N2C[C@H]3C[C@H]3c3nc([C@]4(NC(=O)c5ccc(F)cc5)C[C@H]4C)ccc32)n1] | 4-fluoro-N-((1S,2R)-2-methyl-1-((6aS,7aR)-5-(2-methyl-pyrimidin-4-yl)-6,6a,7,7a-tetra-hydro-5H-cyclopropa[c][1,5]-naphthyridin-2-yl)cyclopropyl)-benzamide | 430.2 |
| 45 | 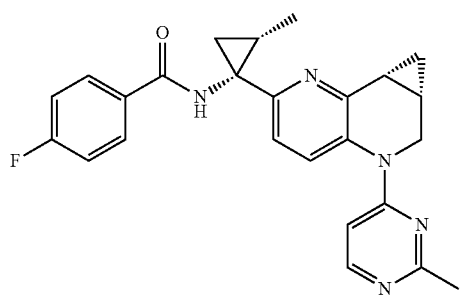 [SMILES: Cc1nccc(N2C[C@H]3C[C@H]3c3nc([C@@]4(NC(=O)c5ccc(F)cc5)C[C@@H]4C)ccc32)n1] | 4-fluoro-N-((1R,2S)-2-methyl-1-((6aS,7aR)-5-(2-methyl-pyrimidin-4-yl)-6,6a,7,7a-tetra-hydro-5H-cyclopropa[c][1,5]-naphthyridin-2-yl)cyclopropyl)-benzamide | 430.2 |
| 46 | 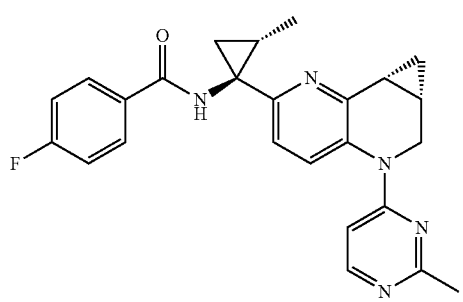 [SMILES: Cc1nccc(N2C[C@H]3C[C@H]3c3nc([C@]4(NC(=O)c5ccc(F)cc5)C[C@@H]4C)ccc32)n1] | 4-fluoro-N-((1S,2S)-2-methyl-1-((6aS,7aR)-5-(2-methyl-pyrimidin-4-yl)-6,6a,7,7a-tetra-hydro-5H-cyclopropa[c][1,5]-naphthyridin-2-yl)cyclopropyl)-benzamide | 430.2 |

Example 47: 4-fluoro-N-(2-methyl-1-(5-(2-methylpyrimidin-4-yl)-6,6a, 7,7a-tetrahydro-5H-cyclopropa[c][1, 5]naphthyridin-2-yl)cyclopropyl)benzamide

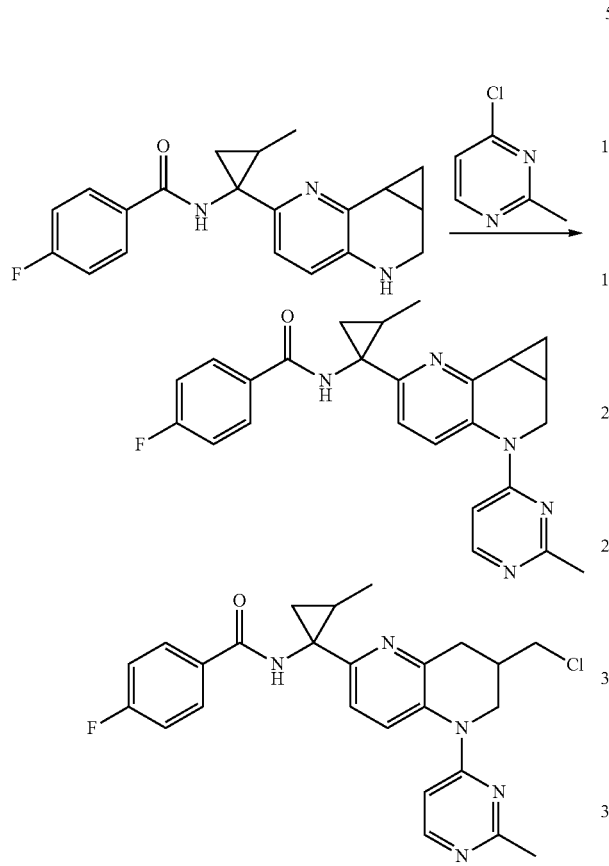

To a vial containing 4-fluoro-N-(2-methyl-1-(6,6a,7,7a-tetrahydro-5H-cyclopropa[c][1,5]naphthyridin-2-yl)cyclopropyl)benzamide (55.00 mg, 0.163 mmol), 4-chloro-2-methylpyrimidine (41.9 mg, 0.326 mmol), and 4-methylbenzenesulfonic acid (28.1 mg, 0.163 mmol) was added NMP (1 mL). The mixture was allowed to stir at 65° C. for 24 h. The mixture was neutralized with sat. NaHCO$_3$, and extracted with ethyl acetate. The combined organics were washed with water and brine, dried over MgSO$_4$, filtered, and concentrated. The residue was purified twice, once on a silica gel column using 20-80% (Hex 1:3EtOH/EtOAc)/mixture) to give a solid and then by HPLC using gradient elution with ACN-water using NH$_4$OH as a modifier. 4-Fluoro-N-(2-methyl-1-(5-(2-methylpyrimidin-4-yl)-6,6a, 7,7a-tetrahydro-5H-cyclopropa[c][1,5]naphthyridin-2-yl)cyclopropyl)benzamide was obtained as a racemic solid. MS ESI calcd. for C$_{25}$H$_{25}$FN$_5$O [M+H]$^+$ 430.2, found 430.2.

1H NMR (499 MHz, DMSO-d6) δ 9.37 (s, 1H), 8.30 (d, J=11.1 Hz, 1H), 7.99 (d, J=8.7 Hz, 2H), 7.75 (d, J=8.4 Hz, 1H), 7.42 (d, J=8.5 Hz, 1H), 7.32 (t, J=8.9 Hz, 2H), 7.03 (d, J=21.9 Hz, 1H), 3.19 (d, J=11.9 Hz, 2H), 2.57 (s, 3H), 2.32-2.23 (m, 1H), 2.23-2.10 (m, 1H), 1.92-1.80 (m, 1H), 1.80-1.60 (m, 1H), 1.28-1.11 (m, 2H), 1.03 (d, J=6.3 Hz, 3H), 0.72-0.59 (m, 1H).

Example 48: 4-fluoro-N-(1-(3-methyl-1-(2-methylpyrimidin-4-yl)-1,2,3,4-tetrahydro-2,4-methano-1,5-naphthyridin-6-yl)cyclopropyl)benzamide

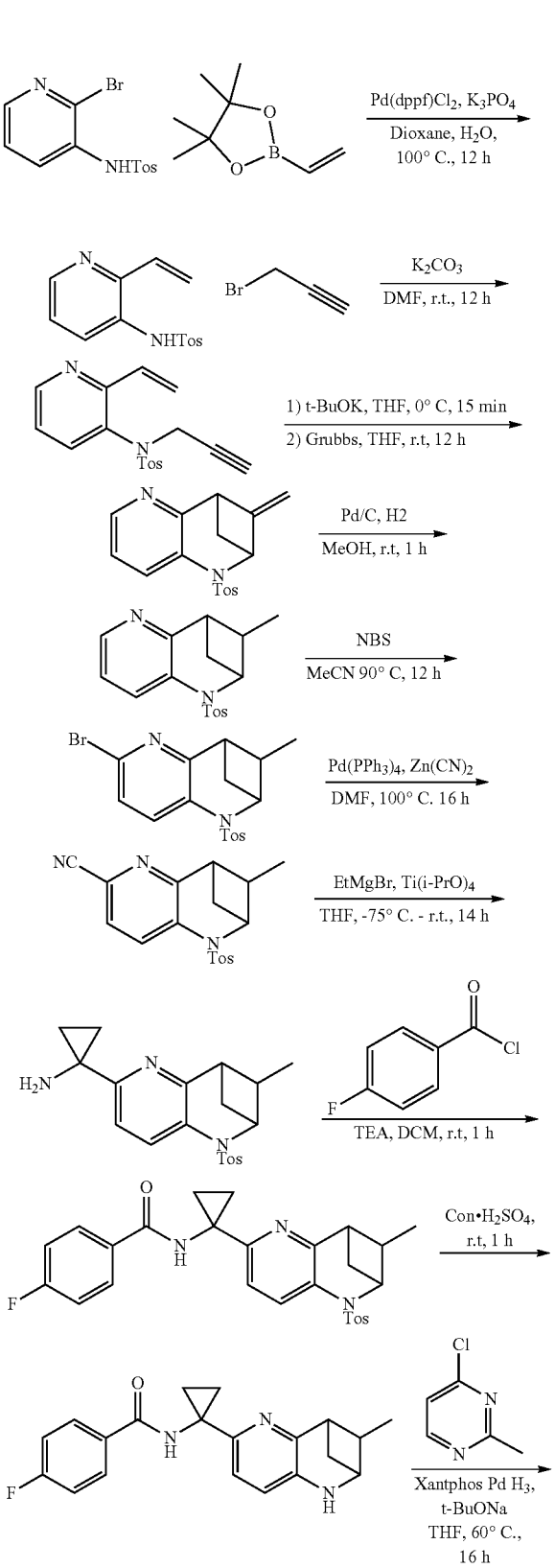

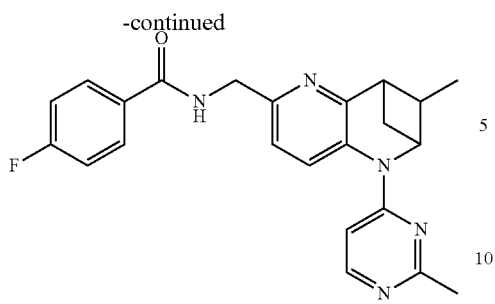

Step 1: 4-methyl-N-(2-vinylpyridin-3-yl)benzenesulfonamide

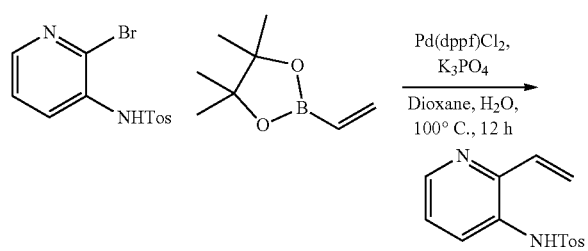

To a solution of N-(2-bromopyridin-3-yl)-4-methylbenzenesulfonamide (6.8 g, 20.78 mmol) in Dioxane (120 mL) and Water (24 mL) were added 4,4,5,5-tetramethyl-2-vinyl-1,3,2-dioxaborolane (4.80 g, 31.2 mmol), potassium phosphate (13.23 g, 62.3 mmol) and Pd (dppf) $Cl_2$ (1.521 g, 2.078 mmol). After the addition was finished, the reaction was stirred at 100° C. under $N_2$ for 12 hrs. The mixture was diluted with water (30 mL) and was extracted with EtOAc (80 mL×2). The combined organic layers were washed with brine, dried over $MgSO_4$, filtered and concentrated in vacuo, the residue was purified by flash silica gel chromatography (ISCO®; Agela® Flash Column Silica-CS (40 g)Eluent of 0-30% Ethyl acetate/Petroleum ether gradient @ 40 mL/min) to give 4-methyl-N-(2-vinylpyridin-3-yl)benzenesulfonamide as a yellow solid. MS (ESI) m/z calc'd for $C_{14}H_{15}N_2O_2S$ $[M+H]^+$ 275.08, found 275.0.

Step 2: 4-methyl-N-(prop-2-yn-1-yl)-N-(2-vinylpyridin-3-yl)benzenesulfonamide

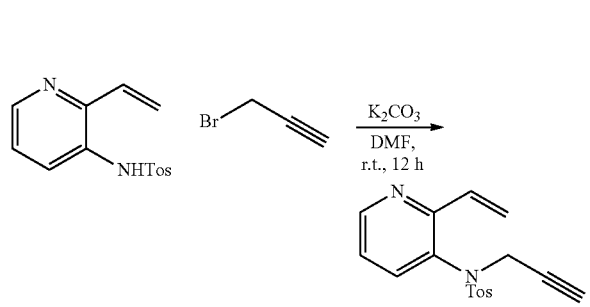

To a solution of 4-methyl-N-(2-vinylpyridin-3-yl)benzenesulfonamide (6 g, 21.87 mmol) in DMF (35 mL) were added $K_2CO_3$ (9.07 g, 65.6 mmol) and 3-bromoprop-1-yne (3.38 g, 28.4 mmol). Then the mixture was stirred at RT for 12 h. The reaction was monitored by LC-MS. The mixture was concentrated in vacuo. The residue was purified by flash silica gel chromatography (ISCO®; Agela® Flash Column Silica-CS (40 g)Eluent of 0-30% Ethyl acetate/Petroleum ether gradient @ 40 mL/min) to give the title compound as a solid.

MS (ESI) m/z calc'd for $C_{17}H_{17}N_2O_2S$ $[M+H]^+$ 313.09, found 313.0.

Step 3: 3-methylene-1-tosyl-1,2,3,4-tetrahydro-2,4-methano-1,5-naphthyridine

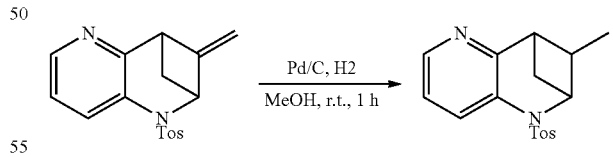

To a solution of 4-methyl-N-(prop-2-yn-1-yl)-N-(2-vinylpyridin-3-yl)benzenesulfonamide (1.2 g, 3.84 mmol) in THF (40 mL) was added t-BuOK (1.9 mL, 1.900 mmol) (1M in THF). The mixture was stirred at 0° C. for 15 min under argon atmosphere. The reaction was quenched by the addition of sat. aqueous $NH_4Cl$ (6 mL), then extracted with EtOAc (40 mL×2). The combined organic layers were washed with brine, dried over $MgSO_4$, and concentrated. The residue was dissolved in THF (100 mL) and benzylidenebis (tricyclohexyl phosphine)dichlororuthenium (0.316 g, 0.384 mmol) was added. Then the mixture was stirred at RT under argon for 12 h. The reaction was monitored by TLC. The solvent was removed in vacuo. The residue was purified by flash silica gel chromatography (ISCO®; Agela® Flash Column Silica-CS (4 g) Eluent of 0-30% Ethyl acetate/Petroleum ether gradient @ 30 mL/min) to give the title compound as an oil.

MS (ESI) m/z calc'd for $C_{17}H_{17}N_2O_2S$ $[M+H]^+$ 313, found 313.2.

Step 4: 3-methyl-1-tosyl-1,2,3,4-tetrahydro-2,4-methano-1,5-naphthyridine

To a solution of 3-methylene-1-tosyl-1,2,3,4-tetrahydro-2,4-methano-1,5-naphthyridine (1.1 g, 3.52 mmol) in MeOH (20 mL) was added Pd—C (0.6 g, 0.564 mmol). The mixture was stirred at RT under $H_2$ (15 psi) for 1 h. The reaction was monitored by LC-MS. After filtration, the filtrate was concentrated in vacuo. The residue was purified by flash silica gel chromatography (ISCO®; Agela® Flash Column Silica-CS (4 g) Eluent of 0-30% Ethyl acetate/Petroleum ether gradient @ 30 mL/min) to give the title compound as an oil.

MS (ESI) m/z calc'd for $C_{17}H_{19}N_2O_2S$ $[M+H]^+$ 315, found 315.5.

Step 5: 6-bromo-3-methyl-1-tosyl-1,2,3,4-tetrahydro-2,4-methano-1,5-naphthyridine

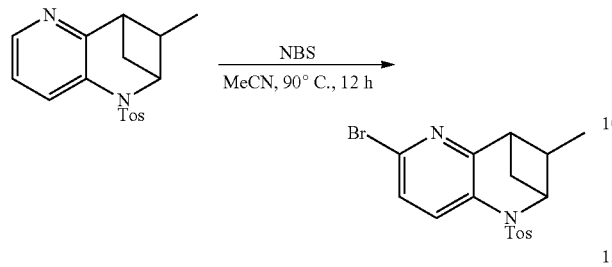

To a stirred solution of 3-methyl-1-tosyl-1,2,3,4-tetrahydro-2,4-methano-1,5-naphthyridine (800 mg, 2.54 mmol) in MeCN (15 mL) was added 1-bromopyrrolidine-2,5-dione (906 mg, 5.09 mmol) at RT and the reaction was stirred at 90° C. for 12 h. The solvent was removed in vacuo. The mixture was diluted with water (20 mL), and extracted by EtOAc (30 mL×3). The organic layers were collected, washed with brine (10 mL), and dried over $Na_2SO_4$. After filtration, the filtrate was concentrated in vacuo. The residue was purified by flash silica gel chromatography (ISCO®; Agela® Flash Column Silica-CS (4 g)Eluent of 0-30% Ethyl acetate/Petroleum ether gradient @ 30 mL/min) to give the title compound as an oil.

MS (ESI) m/z calc'd for $C_{17}H_{18}BrN_2O_2S$ [M+H]$^+$ 395, found 395.0.

Step 6: 3-methyl-1-tosyl-1,2,3,4-tetrahydro-2,4-methano-1,5-naphthyridine-6-carbonitrile

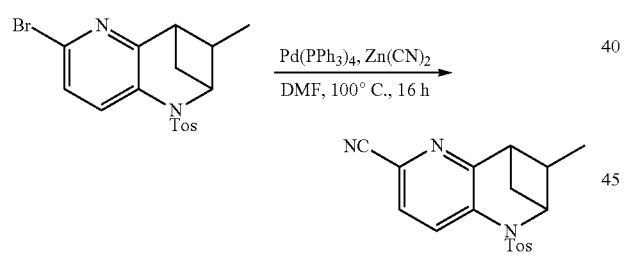

To a stirred solution of 6-bromo-3-methyl-1-tosyl-1,2,3,4-tetrahydro-2,4-methano-1,5-naphthyridine (840 mg, 2.136 mmol) in DMF (15 mL) was added $Zn(CN)_2$ (1.3 g, 11.07 mmol) and $Pd(PPh_3)_4$ (0.494 g, 0.427 mmol) at RT under nitrogen and the reaction was stirred at 100° C. for 16 h. After cooling to RT, the mixture was diluted with water (200 mL), and extracted with EtOAc (30 mL×3). The organic layers were collected, washed with brine (20 mL×2), and dried over $Na_2SO_4$. After filtration, the filtrate was concentrated in vacuo. The residue was purified by flash silica gel chromatography (ISCO®; Agela® Flash Column Silica-CS (4 g)Eluent of 0-40% Ethyl acetate/Petroleum ether gradient @ 30 mL/min) to give the title compound as a solid. MS (ESI) m/z calc'd for $C_{17}H_{18}BrN_2O_2S$ [M+H]$^+$ 395, found 395.0.

Step 7: 1-(3-methyl-1-tosyl-1,2,3,4-tetrahydro-2,4-methano-1,5-naphthyridin-6-yl)cyclopropan-1-amine

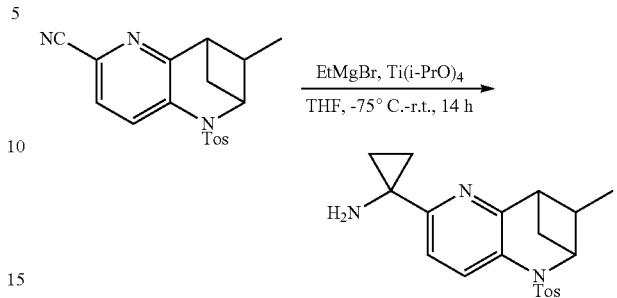

To a solution of 3-methyl-1-tosyl-1,2,3,4-tetrahydro-2,4-methano-1,5-naphthyridine-6-carbonitrile (300 mg, 0.884 mmol) in THF (10 mL) was added titanium (iv) isopropoxide (628 mg, 1.768 mmol) dropwise at −75° C. After stirring at −75° C. for 5 min, ethylmagnesium bromide (1.2 mL, 3.60 mmol) (3.0 M) was added dropwise under nitrogen. After the addition was complete, the reaction mixture was warmed to RT slowly and allowed to stir for 14 h. The reaction was monitored by LC-MS. The mixture was diluted with water (20 mL), and extracted with EtOAc (20 mL×3). The organic layers were collected, washed with brine (10 mL), and dried over $Na_2SO_4$. After filtration, the filtrate was concentrated in vacuo. The residue was purified by flash silica gel chromatography (ISCO®; Agela® Flash Column Silica-CS (4 g) Eluent of 0~100% Ethyl acetate/Petroleum ether gradient @ 30 mL/min) to give the title compound as a solid. MS (ESI) m/z calc'd for $C_{20}H_{24}N_3O_2S$ [M+H]$^+$ 370, found 370.1.

Step 8: 4-fluoro-N-(1-(3-methyl-1-tosyl-1,2,3,4-tetrahydro-2,4-methano-1,5-naphthyridin-6-yl)cyclopropyl)benzamide

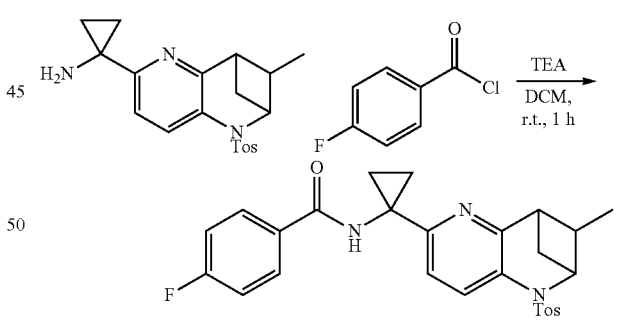

To a stirred solution of 1-(3-methyl-1-tosyl-1,2,3,4-tetrahydro-2,4-methano-1,5-naphthyridin-6-yl)cyclopropanamine (110 mg, 0.298 mmol) in DCM (2 mL) were added 4-fluorobenzoyl chloride (180 mg, 1.135 mmol) and TEA (0.34 mL, 2.471 mmol) at 0° C. The reaction was monitored by LC-MS, and allowed to stir at RT for 1 h. The solvent was removed in vacuo. The residue was purified by flash silica gel chromatography (ISCO®; Agela® Flash Column Silica-CS (4 g)Eluent of 0~100% Ethyl acetate/Petroleum ether gradient @ 30 mL/min) to give the title compound as a solid. MS (ESI) m/z calc'd for $C_{20}H_{24}N_3O_2S$ [M+H]$^+$ 492, found 492.2.

Step 9: 4-fluoro-N-(1-(3-methyl-1,2,3,4-tetrahydro-2,4-methano-1,5-naphthyridin-6-yl)cyclopropyl)benzamide

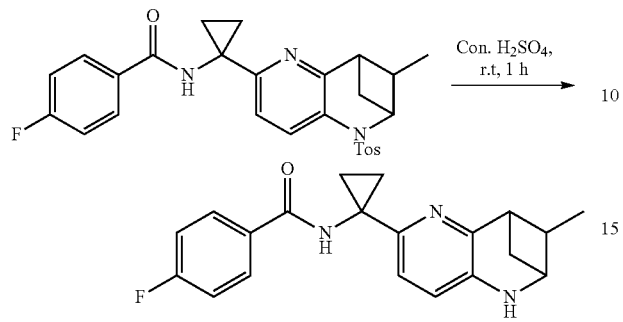

To a solution of 4-fluoro-N-(1-(3-methyl-1-tosyl-1,2,3,4-tetrahydro-2,4-methano-1,5-naphthyridin-6-yl)cyclopropyl)benzamide (80 mg, 0.163 mmol) was added H$_2$SO$_4$ (2 mL, 37.5 mmol). The mixture was stirred at RT for 1 h. The reaction was poured into ice water (4 mL), then basified with NaOH (solid), and sat. Na$_2$CO$_3$ were added at 0° C. until pH=7. The mixture was extracted with EtOAc (20 mL×3), the organic layers were collected, washed with brine (10 mL), and dried over Na$_2$SO$_4$. After filtration, the filtrate was concentrated in vacuo. The residue was purified by Prep-TLC (Petroleum ether/EtOAc=1/1) to give the title compound as a solid. MS (ESI) m/z calc'd for C$_{20}$H$_{21}$FN$_3$O [M+H]$^+$ 338, found 338.1.

Step 10: 4-fluoro-N-(1-(3-methyl-1-(2-methylpyrimidin-4-yl)-1,2,3,4-tetrahydro-2,4-methano-1,5-naphthyridin-6-yl)cyclopropyl)benzamide

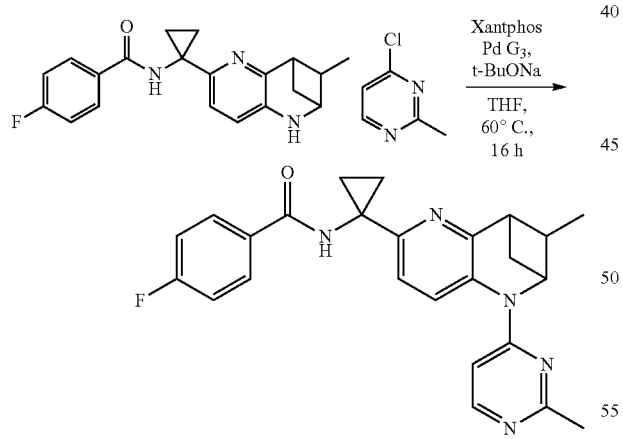

To a stirred solution of 4-fluoro-N-(1-(3-methyl-1,2,3,4-tetrahydro-2,4-methano-1,5-naphthyridin-6-yl)cyclopropyl)benzamide (10 mg, 0.030 mmol) in THF (3 mL) were added 4-chloro-2-methylpyrimidine (6 mg, 0.047 mmol), t-BuONa (9 mg, 0.094 mmol), and Xantphos precatalyst G3 (3 mg, 3.16 μmol) at RT and stirred at 60° C. under nitrogen for 16 h. After cooling to RT, the mixture was concentrated in vacuo. The residue was purified by reverse phase HPLC on a GILSON 281 instrument fitted with a YMC-Actus Pro C18 (150×30 mm×5 μm) using water (0.1% TFA) and ACN as eluents (Mobile phase A water (0.1% TFA), Mobile phase B acetonitrile, Detective wavelength: 220 nm) followed by lyophilization to give the title compound as a solid.

MS (ESI) m/z calc'd for C$_{25}$H$_{25}$FN$_5$O [M+H]$^+$ 430, found 430.2.

$^1$H NMR (400 MHz, CD$_3$OD) δ 8.50 (d, J=8.6 Hz, 1H), 8.26 (d, J=6.4 Hz, 1H), 8.07-7.93 (m, 2H), 7.35-7.16 (m, 3H), 7.06 (d, J=6.1 Hz, 1H), 5.24 (q, J=5.1 Hz, 1H), 3.45-3.39 (m, 1H), 2.80-2.68 (m, 1H), 2.54 (s, 3H), 2.49 (td, J=5.0, 10.0 Hz, 1H), 2.32 (q, J=7.6 Hz, 1H), 1.70-1.62 (m, 2H), 1.47-1.37 (m, 2H), 0.61 (d, J=6.6 Hz, 3H).

Example 49: benzyl 6-(1-(4-fluorobenzamido)cyclopropyl)-3,4-dihydro-2,4-methano-1,5-naphthyridine-1(2H)-carboxylate

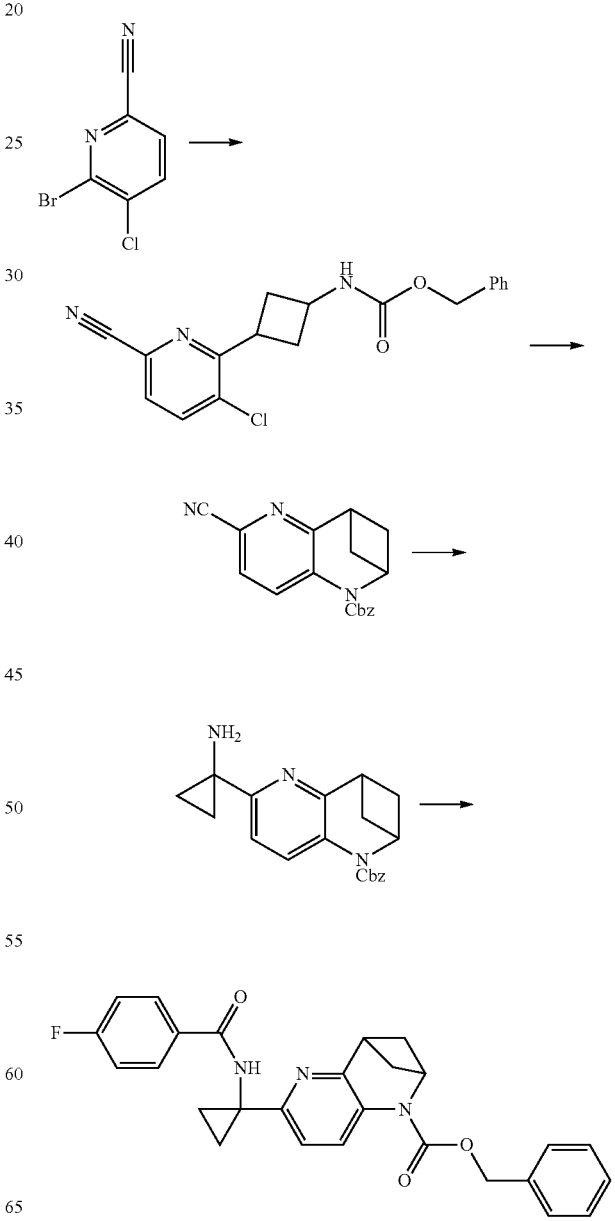

Step 1: benzyl (3-(3-chloro-6-cyanopyridin-2-yl)cyclobutyl)carbamate

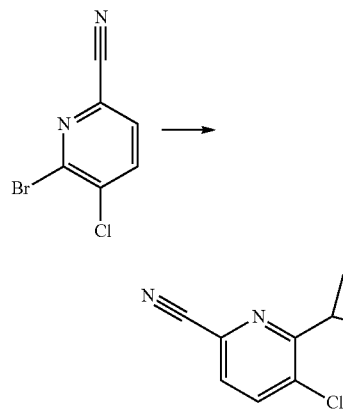

A 40 mL vial equipped with a stir bar was charged with 6-bromo-5-chloropyridine-2-carbonitrile (500 mg, 2.299 mmol), benzyl (3-bromocyclobutyl)carbamate (751 mg, 2.64 mmol), 4,4'-di-tert-butyl-2,2'-bipyridine (61.7 mg, 0.230 mmol), (Ir[dF(CF$_3$)ppy]$_2$(dtbpy))PF$_6$ (25.8 mg, 0.023 mmol), and nickel(II) chloride ethylene glycol dimethyl ether complex (50.5 mg, 0.230 mmol). The mixture was transferred into a glove box. Anhydrous 1,2-dimethoxyethane (20 mL), tris(trimethylsilyl)silane (0.706 mL, 2.299 mmol), and 2,6-dimethylpyridine (0.536 mL, 4.60 mmol) were added into the reaction mixture before it was taken out of glove box. The mixture was shone with the Royal Blue (450 nm) LED light for 3 h, with stirring at 1000 rpm. The reaction mixture was partitioned between EtOAc and water. Aqueous layer was extracted with EtOAc. The combined organic layers were concentrated to dryness. The crude was purified with ISCO silica gel column (120 g, gold) eluting with EtOAc/hexane 0-60% gradient to give the title compound.

MS (ESI) m/z calc'd for C$_{18}$H$_{17}$ClN$_3$O$_2$ [M+H]$^+$ 342.09, found 342.1.

Step 2: benzyl 6-cyano-3,4-dihydro-2,4-methano-1,5-naphthyridine-1(2H)-carboxylate

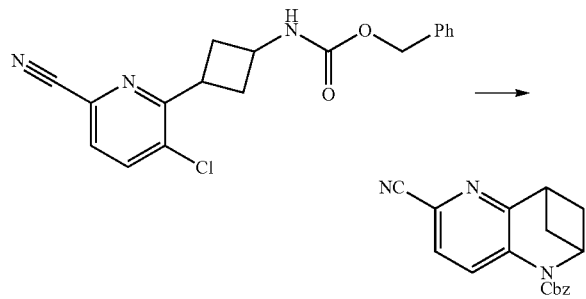

To a vial with cap was charged with chloro(2-dicyclohexylphosphino-2',6'-dimethoxy-1,1'-biphenyl)[2-(2'-amino-1,1'-biphenyl)]palladium(II) (SPhos G2, 96 mg, 0.134 mmol), potassium phosphate (0.222 mL, 2.68 mmol), benzyl (3-(3-chloro-6-cyanopyridin-2-yl)cyclobutyl)carbamate (305 mg, 0.892 mmol), and dioxane (15 mL). The mixture was degassed through nitrogen/vacuum exchange. The reaction mixture was heated at 80° C. overnight. The reaction mixture was cooled and filtered through a pad of Celite. Solvent was removed and the crude was purified with ISCO silica gel column (80 g, gold) eluting with EtOAc/hexane 0-60% gradient to give the title compound.

MS (ESI) m/z calc'd for C$_{18}$H$_{16}$N$_3$O$_2$ [M+H]$^+$ 306.12, found 306.1.

Step 3: benzyl 6-(1-aminocyclopropyl)-3,4-dihydro-2,4-methano-1,5-naphthyridine-1(2H)-carboxylate

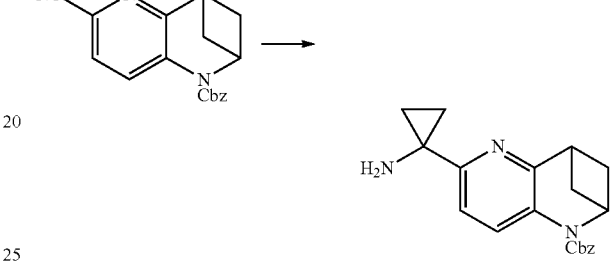

To a mixture of benzyl 6-cyano-3,4-dihydro-2,4-methano-1,5-naphthyridine-1(2H)-carboxylate (175 mg, 0.573 mmol) in THF (3.0 ml) at −78° C. was added titanium(IV) isopropoxide (339 µl, 1.146 mmol). The mixture stirred for 15 min before adding ethylmagnesium bromide (573 µl, 1.719 mmol, 3.0 M in ether) dropwise. The mixture was allowed to slowly warm to ambient temperature overnight. The mixture was quenched with a sat. solution of NaCl (10 mL). The mixture was filtered through a pad of celite, the filtrate was extracted with EtOAc (3×@ 15 mL), dried over MgSO$_4$, and concentrated to give crude benzyl 6-(1-aminocyclopropyl)-3,4-dihydro-2,4-methano-1,5-naphthyridine-1(2H)-carboxylate which was used directly without any purification.

MS (ESI) m/z calc'd for C$_{20}$H$_{22}$N$_3$O$_2$ [M+H]$^+$ 336.16, found 336.2.

Step 4: benzyl 6-(1-(4-fluorobenzamido)cyclopropyl)-3,4-dihydro-2,4-methano-1,5-naphthyridine-1(2H)-carboxylate

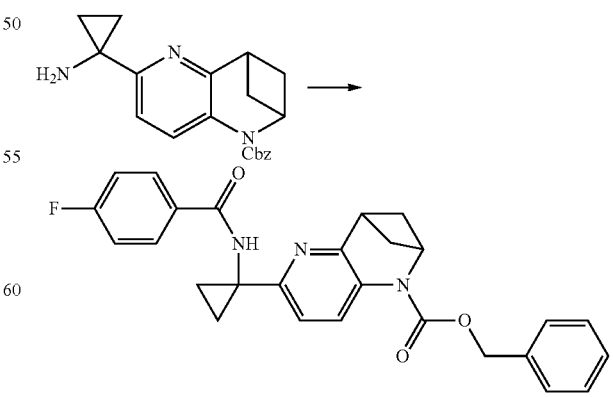

4-Fluorobenzoyl chloride (0.098 ml, 0.827 mmol) was added to a stirred mixture of benzyl 6-(1-aminocyclopropyl)-3,4-dihydro-2,4-methano-1,5-naphthyridine-1(2H)-carboxylate (185 mg, 0.552 mmol) and Hunig's Base (0.289 ml, 1.655 mmol) in CH₂Cl₂ (3 ml) and the mixture was stirred at RT for 1 h. The mixture was diluted with ethyl acetate, washed with aq. sodium hydrogen carbonate, water, brine, and dried over MgSO₄. The mixture was filtered and the solvent was evaporated under reduced pressure. The residue was purified by column chromatography on silica gel Isolute Flash Si; 100 g prepacked, eluting with EtOAc/isohexane gradient 0-60% to give the title compound.

MS (ESI) m/z calc'd for $C_{27}H_{25}FN_3O_3$ [M+H]⁺ 458.2, found 458.2.

¹H NMR (500 MHz, CD₃OD) δ 8.80 (br. s, 1H), 7.94 (dd, J=10, 5 Hz, 2H), 7.5-7.3 (m, 6H), 7.22 (t, J=10 Hz, 2H), 5.28 (s, 2H), 3.64 (br. q, 1H), 2.66 (m, 2H), 1.64 (m, 2H), 1.58 (m, 2H), 1.40 (br. q, 2H), 1.06 (t, J=10 Hz, 1H).

Example 50: cyclopropyl 6-(1-(4-fluorobenzamido)cyclopropyl)-3,4-dihydro-2,4-methano-1,5-naphthyridine-1(2H)-carboxylate Step 1: 4-fluoro-N-(1-(1,2,3,4-tetrahydro-2,4-methano-1,5-naphthyridin-6-yl)cyclopropyl)benzamide

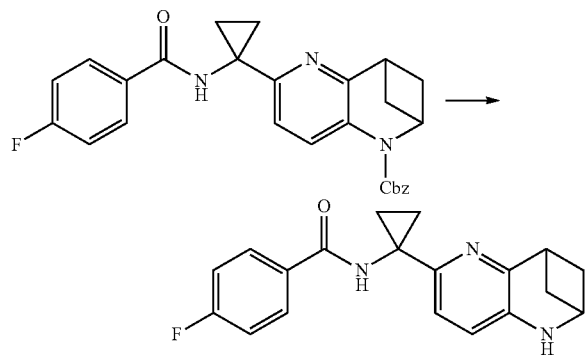

Palladium on carbon (28 mg, 0.263 mmol) was added to a stirred mixture of benzyl 6-(1-(4-fluorobenzamido)cyclopropyl)-3,4-dihydro-2,4-methano-1,5-naphthyridine-1(2H)-carboxylate (140 mg, 0.306 mmol) in ethanol (5 ml)/methanol (2 ml)/CH₂Cl₂ (2 ml)/ethyl acetate (2 ml) and the mixture was H₂/vacuum exchanged for three times before it was stirred at RT for 2.5 h. The mixture was filtered through a pad of Celite and washed with EtOAc. Solvent was removed under reduced pressure to give the title compound which was used directly for next step. MS (ESI) m/z calc'd for $C_{19}H_{19}FN_3O$ [M+H]⁺ 324.1, found 324.2.

Step 2: cyclopropyl 6-(1-(4-fluorobenzamido)cyclopropyl)-3,4-dihydro-2,4-methano-1,5-naphthyridine-1(2H)-carboxylate 2,2,2-trifluoroacetate

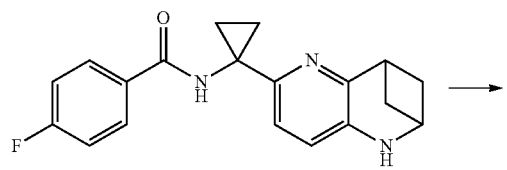

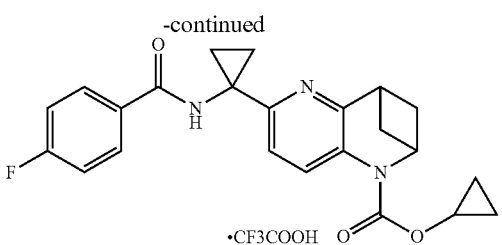

To a solution of 4-fluoro-N-(1-(1,2,3,4-tetrahydro-2,4-methano-1,5-naphthyridin-6-yl)cyclopropyl)benzamide (19.1 mg, 0.059 mmol) and DIEA (0.031 mL, 0.177 mmol) in CH₂Cl₂ (0.6 mL) was added cyclopropyl carbonochloridate (14.24 mg, 0.118 mmol) dropwise. The mixture was stirred at RT for 2 h. Solvent was removed and the residue was purified with reversed phase HPLC to give the title compound.

MS (ESI) m/z calc'd for $C_{23}H_{23}FN_3O_3$ CF₃COOH [M+H]⁺ 408.2, found 408.1.

¹H NMR (500 MHz, CD₃OD) δ 8.85 (s, 1H), 7.95 (dd, J=10, 5 Hz, 2H), 7.53 (d, J=5 Hz, 1H), 7.22 (t, J=10 Hz, 2H), 5.18 (dd, J=10, 5 Hz, 1H), 4.21 (m, 1H), 3.69 (dd, J=10, 5 Hz, 1H), 2.67 (m, 2H), 1.65 (dt, J=5 Hz, 2H), 1.57 (dq, J=10, 5 Hz, 2H), 1.42 (dd, J=5 Hz, 2H), 0.79 (m, 4H).

Example 51: 4-fluoro-N-(1-(1-(2-methylpyrimidin-4-yl)-1,2,3,4-tetrahydro-2,4-methano-1,5-naphthyridin-6-yl)cyclopropyl)benzamide

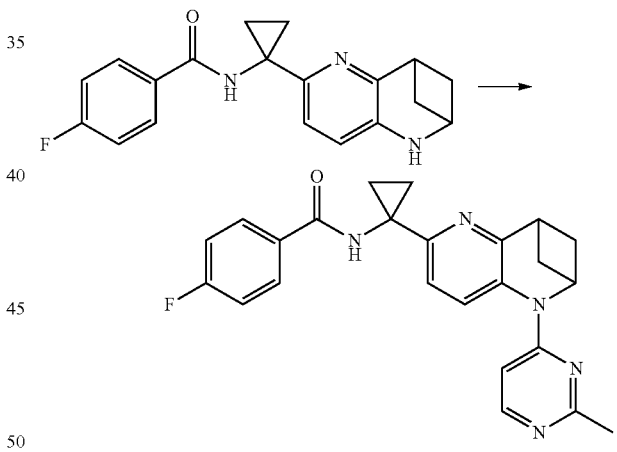

To a vial containing 4-fluoro-N-(1-(1,2,3,4-tetrahydro-2,4-methano-1,5-naphthyridin-6-yl)cyclopropyl)benzamide (20 mg, 0.062 mmol), 4-chloro-2-methylpyrimidine (15.90 mg, 0.124 mmol), and 4-methylbenzenesulfonic acid hydrate (12.35 mg, 0.065 mmol) was added NMP (0.60 mL). The mixture was allowed to stir at 75° C. for 20 h before 15.9 mg of chloropyrimidine was added. The mixture was neutralized with sat. NaHCO₃ and extracted with ethyl acetate. The combined organics was washed with water and brine, and dried over MgSO₄. The mixture was filtered and concentrated. The residue was purified with reversed phase HPLC to give the title compound. MS (ESI) m/z calc'd for $C_{24}H_{23}FN_5O$ [M+H]⁺ 416.2, found 416.2.

¹H NMR (500 MHz, CD₃OD) δ 8.77 (br. s, 1H), 8.33 (d, J=5 Hz, 1H), 7.99 (dd, J=10, 5 Hz, 2H), 7.34 (d, J=10 Hz, 1H), 7.34 (d, J=10 Hz, 1H), 7.24 (d, J=10 Hz, 2H), 5.59 (m,

1H), 3.55 (dd, J=10, 5 Hz, 1H), 2.82 (m, 2H), 2.69 (s, 3H), 1.76 (dd, J=10, 5 Hz, 2H), 1.72 (q, J=5 Hz, 2H), 1.36 (q, J=5 Hz, 2H).

The examples in the following table were prepared in an analogous manner to Example 10 using appropriate starting materials described previously or commercially available Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

| Ex. # | Structure | Chemical Name | Mass [M + H]+ |
|---|---|---|---|
| 52 | 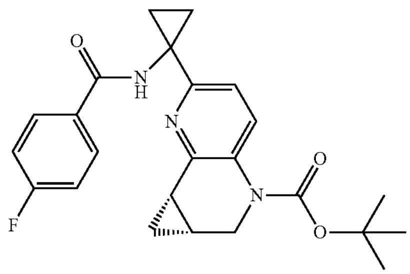 [SMILES: CC(C)(C)OC(=O)N1C[C@@H]2C[C@@H]2c2nc(C3(NC(=O)c4ccc(F)cc4)CC3)ccc21] | tert-butyl (6aR,7aS)-2-(1-(4-fluorobenzamido)cyclopropyl)-6,6a,7,7a-tetrahydro-5H-cyclopropa[c][1,5]naphthyridine-5-carboxylate | 424.2 |
| 53 | 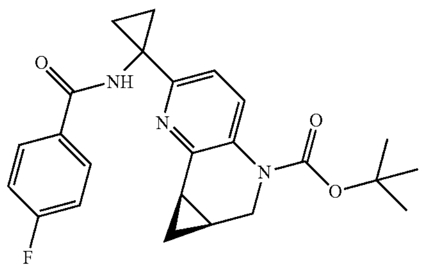 [SMILES: CC(C)(C)OC(=O)N1C[C@H]2C[C@H]2c2nc(C3(NC(=O)c4ccc(F)cc4)CC3)ccc21] | tert-butyl (6aS,7aR)-2-(1-(4-fluorobenzamido)cyclopropyl)-6,6a,7,7a-tetrahydro-5H-cyclopropa[c][1,5]naphthyridine-5-carboxylate | 424.2 |

The examples in the following table were prepared in an analogous manner to Example 29 using appropriate starting materials described previously or commercially available.

Frozen HeLa cells were thawed and transferred into HeLa assay medium (99% complete HeLa culture medium, 1% Pen/Strep) with 20 mL medium/vial of cells. The cells were

| Ex. # | Structure | Chemical Name | Mass [M + H]+ |
|---|---|---|---|
| 54 | 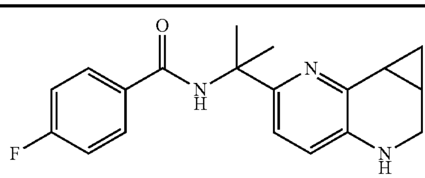 | 4-fluoro-N-(2-(6,6a,7,7a-tetrahydro-5H-cyclopropa[c][1,5]-naphthyridin-2-yl)propan-2-yl)-benzamide | 326.2 |
| 55 | 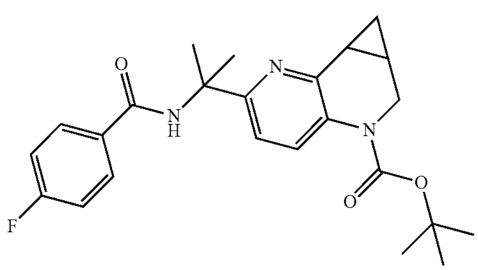 [SMILES: CC(C)(C)OC(=O)N1CC2CC2c2nc(C(C)(C)NC(=O)c3ccc(F)cc3)ccc21] | tert-butyl 2-(2-(4-fluorobenzamido)propan-2-yl)-6,6a,7,7a-tetrahydro-5H-cyclopropa[c]-[1,5]naphthyridine-5-carboxylate | 426.2 |

Biological Assays
IDO1 Cellular Assay in HeLa Cells Stimulated with IFNγ

HeLa cells were cultured in complete HeLa culture medium (90% EMEM, 10% heat-inactivated fetal bovine serum) and expanded to about $1\times10^9$ cells. The cells were then collected and frozen down at $1\times10^7$ cells/vial in 1 mL frozen medium (90% complete HeLa culture medium, 10% DMSO).

spun down at 250 g in a table top centrifuge for 5 min and suspended in same volume of HeLa assay medium. The cells were then counted and adjusted to a density of $2\times10^5$ cells/mL in HeLa assay medium. Sterile L-tryptophan were added to the cells with final concentration of 300 uM L-tryptophan. A small aliquot (2 mL/plate) of HeLa cells were set aside and were not treated with IFNγ, to serve as the Max-E control. The rest of HeLa cells were added with sterile IFNγ (Cat #285-IF, R & D systems) with a final concentration of 100 ng/mL.

HeLa cells with and without IFNγ were dispensed to the respective wells of 384-well assay plates containing the compounds. The plates were incubated for about 48 hours at a 37° C., 5% $CO_2$ incubator. Afterwards, 12 μL of 0.5 M methyl isonipecotate in dimethyl sulfoxide were added into each well and the plates were sealed and incubated at 37° C. without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

The biological activity data using the IDO1 cellular assay described above are summarized in the table below. Compounds disclosed herein generally have $IC_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Specific $IC_{50}$ activity data for the exemplified compounds disclosed herein is provided in the following table.

IDO1 Human Whole Blood Assay

Compounds to be tested were serially diluted in ten 3-fold steps in DMSO starting from 10 mM. 3 μL of compound dilutions or DMSO alone were then dispensed from the dilution plate into a polypropylene 96-well assay plate containing 97 μL of RPMI medium using an Echo 555 acoustic liquid handler (Labcyte). LPS and IFNγ was prepared in RPMI medium to a 10× of final conc. (1000 ng/mL), final concentration is 100 ng/mL.

Human whole blood was drawn in sodium heparin coated tubes from healthy internal donors. 240 μL of blood was transferred to each of the wells of a v-bottom 96 well plate. 30 μL of compound was transferred from intermediate dilution plate, and incubated for 15 min. 30 μL from stimulants was then transferred to blood and mixed thoroughly. Plate was covered with breathable membrane and incubated at 37° C. for overnight (18 h).

On day 2, isotope labeled standard solutions of kynurenine and tryptophan was made in water at 10× concentration and 30 μL was added to the blood at 3 μM final concentration. The assay plates were centrifuged at 300×G for 10 min with no brake to separate plasma from red blood cells. 60 μL of plasma samples was removed without disturbing red blood cells. Plasma was diluted with RPMI in 1:1 ratio and proteins were precipitated out with two volumes of Acetonitrile. The plates were centrifuged at 4000×G for 60 min. 20 μL of supernatant was carefully transferred to a 384 well plate containing 40 μL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 μL were injected onto an Atlantis T3 column (2.1 mm×150 mm, 3 μm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data were acquired in positive mode using a HESI interface. The operational parameters for the TSQ Quantum Ultra instrument were a spray voltage of 4000 V, capillary temperature of 380° C., vaporizer temperature 400° C., sheath gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and $IC_{50}$ values. Compounds were titrated and $IC_{50}$'s were calculated by 4 parameter sigmoidal curve fitting formula.

The biological activity data of selective compounds using the IDO1 human whole blood assay described above are summarized in the table below.

| Ex. # | IDO1 HELA Cell Assay, $IC_{50}$, nM | Whole Blood Assay, $IC_{50}$, nM |
|---|---|---|
| 1 | 1.67 | |
| 2 | 1.5 | |
| 3 | 44.02 | |
| 4 | 2.92 | 37 |
| 5 | 4.71 | |
| 6 | | |
| 7 | | |
| 8 | 2.91 | |
| 9 | 8.21 | |
| 10 | 96.68 | |
| 11 | 2300 | |
| 12 | 1.91 | |
| 13 | 1.07 | |
| 14 | 3.5 | 105 |
| 15 | 4.4 | 50.0 |
| 16 | 2.6 | 32 |
| 17 | 9.02 | |
| 18 | 12.05 | 248 |
| 19 | 10.98 | 151 |
| 20 | | |
| 21 | 6.03 | 946 |
| 22 | 61.62 | |
| 23 | 17.01 | |
| 24 | 20.92 | |
| 25 | 15.38 | |
| 26 | 34.96 | |
| 27 | 3.23 | 463 |
| 28 | 29.35 | |
| 29 | 90 | |
| 30 | 6.6 | 126 |
| 31 | 80.63 | |
| 32 | 7.56 | 778 |
| 33 | 4.05 | 465 |
| 34 | 221 | |
| 35 | 1300 | 778 |
| 36 | 211.2 | |
| 37 | 2.83 | 54 |
| 38 | 6.77 | |
| 39 | 10.52 | |
| 40 | 2.83 | |
| 41 | 2.36 | |
| 42 | 3.17 | |
| 43 | 3.27 | |
| 44 | 4.34 | |
| 45 | 3.39 | |
| 46 | 24.41 | |
| 47 | 51.98 | |
| 48 | 76.35 | |
| 49 | 20.4 | |
| 50 | 5.76 | |
| 51 | 8.08 | |
| 52 | 96.6 | |
| 53 | 4.62 | |

-continued

| Ex. # | IDO1 HELA Cell Assay, IC$_{50}$, nM | Whole Blood Assay, IC$_{50}$, nM |
|---|---|---|
| 54 | 4900 | |
| 55 | 16.56 | |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

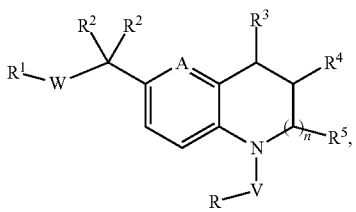

(I)

wherein:
n is 0 or 1;
A is selected from (1) —CH═ and (2) —N═;
V is selected from (1) absent and (2) —C(O)—;
W is selected from (1) —C(O)—NH— and (2) —NH—C(O)—;
$R^1$ is selected from (1) aryl and (2) heteroaryl, wherein each of the aryl and heteroaryl is optionally substituted with 1-3 substituents independently selected from:
  (a) halogen, and
  (b) $C_{1-6}$ alkyl, optionally substituted with 1-4 halogens;
each occurrence of $R^2$ is independently selected from: (1) hydrogen and (2) $C_{1-6}$ alkyl;
or alternatively, the two $R^2$ groups together with the carbon to which they are attached form a $C_{3-4}$ cycloalkyl, wherein the $C_{3-4}$ cycloalkyl is optionally substituted with $C_{1-6}$ alkyl;
$R^3$ is hydrogen, n is 1, and $R^4$ and $R^5$ together with the carbons to which they are attached form a $C_{3-4}$ cycloalkyl;
or alternatively, $R^5$ is hydrogen, n is 1, and $R^3$ and $R^4$ together with the carbons to which they are attached form a $C_{3-4}$ cycloalkyl;
or alternatively, $R^5$ is absent, n is 0, and $R^3$ and $R^4$ together with the carbons to which they are attached form a $C_{3-4}$ cycloalkyl;
or alternatively, $R^4$ is selected from (1) hydrogen and (2) $C_{1-6}$ alkyl optionally substituted with 1-3 halogens, n is 1, and $R^3$ and $R^5$ together with the carbons to which they are attached and the carbon to which $R^4$ is attached form a $C_{4-5}$ cycloalkyl;
R is selected from:
  (1) hydrogen,
  (2) aryl,
  (3) $C_{1-6}$ alkyl, optionally substituted with 1-4 substituents halogens,
  (4) $C_{3-6}$ cycloalkyl,
  (5) —O—$C_{1-6}$ alkyl, optionally substituted with phenyl,
  (6) —O—$C_{3-6}$ cycloalkyl,
  (7) —O-heterocyclyl, and
  (8) heteroaryl,
wherein each of the aryl of (2) and heteroaryl of (8) is optionally substituted with 1-3 substituents independently selected from:
  (a) halogen,
  (b) —OH,
  (c) $C_{1-6}$ alkyl, optionally substituted with 1-4 substituents independently selected from (i) —OH and (ii) halogen,
  (d) —O—$C_{1-6}$ alkyl, optionally substituted with 1-4 substituents independently selected from (i) —OH and (ii) halogen,
  (e) $C_{3-6}$ cycloalkyl,
  (f) —O—$C_{3-6}$ cycloalkyl, and
  (g) —C(O)—O—$C_{1-6}$ alkyl.

2. The compound of claim 1, or a pharmaceutically acceptable salt thereof, wherein $R^1$ is phenyl, optionally substituted with 1-3 halogens.

3. The compound of claim 1, or a pharmaceutically acceptable salt thereof, wherein:
each occurrence of $R^2$ is independently selected from: (1) hydrogen and (2) $C_{1-4}$ alkyl;
or alternatively, the two $R^2$ groups together with the carbon to which they are attached form a $C_{3-4}$ cycloalkyl, wherein the $C_{3-4}$ cycloalkyl is optionally substituted with methyl or ethyl.

4. The compound of claim 1, or a pharmaceutically acceptable salt thereof, wherein:
each occurrence of $R^2$ is independently selected from: (1) hydrogen, (2) methyl, and (3) ethyl;
or alternatively, the two $R^2$ groups together with the carbon to which they are attached form a cyclopropyl or cyclobutyl, wherein each of the cyclopropyl and cyclobutyl is optionally substituted with methyl.

5. The compound of claim 1, or a pharmaceutically acceptable salt thereof, wherein:
$R^3$ is hydrogen, n is 1, and $R^4$ and $R^5$ together with the carbons to which they are attached form a cyclopropyl or cyclobutyl;
or alternatively, $R^5$ is hydrogen, n is 1, and $R^3$ and $R^4$ together with the carbons to which they are attached form a cyclopropyl or cyclobutyl;
or alternatively, $R^5$ is absent, n is 0, and $R^3$ and $R^4$ together with the carbons to which they are attached form a cyclopropyl or cyclobutyl;
or alternatively, $R^4$ is selected from (1) hydrogen, (2) methyl, and (3) ethyl, n is 1, and $R^3$ and $R^5$ together with the carbons to which they are attached and the carbon to which $R^4$ is attached form a cyclobutyl or cyclopentyl.

6. The compound of claim 1 or a pharmaceutically acceptable salt thereof, wherein:
$R^3$ is hydrogen, n is 1, and $R^4$ and $R^5$ together with the carbons to which they are attached form a cyclobutyl;
or alternatively, $R^5$ is hydrogen, n is 1, and $R^3$ and $R^4$ together with the carbons to which they are attached form a cyclopropyl;
or alternatively, $R^5$ is absent, n is 0, and $R^3$ and $R^4$ together with the carbons to which they are attached form a cyclopropyl or cyclobutyl;
or alternatively, $R^4$ is selected from (1) hydrogen and (2) methyl, n is 1, and $R^3$ and $R^5$ together with the carbons to which they are attached and the carbon to which R⁴ is attached form a cyclobutyl.

7. The compound of claim 1, or a pharmaceutically acceptable salt thereof, wherein:
R is selected from:
(1) hydrogen,
(2) phenyl,
(3) $C_{1-4}$ alkyl, optionally substituted with 1-3 halogens,
(4) $C_{3-4}$ cycloalkyl,
(5) —O—$C_{1-4}$ alkyl, optionally substituted with phenyl,
(6) —O—$C_{3-4}$ cycloalkyl,
(7) —O-heterocyclyl, wherein the heterocyclyl is a 6-membered saturated monocyclic ring containing 1-3 hetero atoms independently selected from O, S, and N, and
(8) a 5- or 6-membered monocyclic heteroaryl containing 1-3 hetero atoms independently selected from O, S, and N,
wherein each of the phenyl of (2) and the heteroaryl of (8) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) $C_{3-4}$ cycloalkyl,
(f) —O—$C_{3-4}$ cycloalkyl, and
(g) —C(O)—O—$C_{1-4}$ alkyl.

8. The compound of claim 1, or a pharmaceutically acceptable salt thereof, wherein:
R is selected from:
(1) hydrogen,
(2) $C_{1-4}$ alkyl, optionally substituted with 1-3 halogens,
(3) $C_{3-4}$ cycloalkyl,
(4) —O—$C_{1-4}$ alkyl, optionally substituted with phenyl,
(5) —O-cyclopropyl,
(6) —O-heterocyclyl, wherein the heterocyclyl is a 6-membered saturated monocyclic ring containing 1-2 hetero atoms independently selected from O, S, and N, and
(7) a heteroaryl selected from (a) pyridinyl and (b) pyrimidinyl,
wherein the heteroaryl of (7) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

9. The compound of claim 1, or a pharmaceutically acceptable salt thereof, wherein:
R is selected from:
(1) hydrogen,
(2) $C_{1-4}$ alkyl, optionally substituted with 1-3 halogens,
(3) cyclopropyl,
(4) —O—$C_{1-4}$ alkyl, optionally substituted with phenyl,
(5) —O-cyclopropyl,
(6) —O-heterocyclyl, wherein the heterocyclyl is tetrahydropyranyl, and
(7) a heteroaryl selected from (a) pyridinyl and (b) pyrimidinyl,
wherein the heteroaryl of (7) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

10. The compound of claim 1, or a pharmaceutically acceptable salt thereof, of formula (Ia):

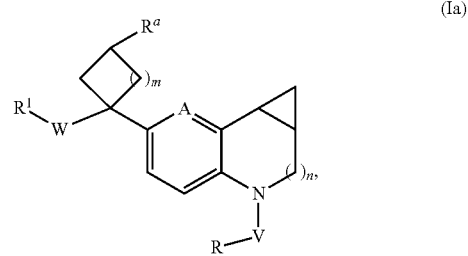

wherein:
m is 0 or 1; n is 0 or 1;
A is selected from (1) —CH= and (2) —N=;
$R^a$ is selected from: (1) hydrogen and (2) $C_{1-4}$ alkyl;
$R^1$ is phenyl, optionally substituted with 1-3 halogens;
V is selected from (1) absent and (2) —C(O)—;
W is selected from (1) —C(O)—NH— and (2) —NH—C(O)—; and
R is selected from:
(1) hydrogen,
(2) $C_{1-4}$ alkyl, optionally substituted with 1-3 halogens,
(3) $C_{3-4}$ cycloalkyl,
(4) —O—$C_{1-4}$ alkyl, optionally substituted with phenyl,
(5) —O-cyclopropyl,
(6) —O-heterocyclyl, wherein the heterocyclyl is a 6-membered saturated monocyclic ring containing 1-2 hetero atoms independently selected from O, S, and N, and
(7) a heteroaryl selected from (a) pyridinyl and (b) pyrimidinyl,
wherein the heteroaryl of (7) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen, (e) cyclopropyl,
(f) —O-cyclopropyl, and
(g) —C(O)—O-methyl.

11. The compound of claim 10, or a pharmaceutically acceptable salt thereof, wherein:
$R^a$ is selected from: (1) hydrogen and (2) methyl;
$R^1$ is phenyl, optionally substituted with a halogen; and
R is selected from:
(1) hydrogen,
(2) $C_{1-4}$ alkyl, optionally substituted with 1-3 halogens,
(3) cyclopropyl,
(4) —O—$C_{1-4}$ alkyl, optionally substituted with phenyl,
(5) —O-cyclopropyl,
(6) —O-heterocyclyl, wherein the heterocyclyl is tetrahydropyranyl, and
(7) a heteroaryl selected from (a) pyridinyl and (b) pyrimidinyl,
wherein heteroaryl of (7) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

12. The compound of claim 1, or a pharmaceutically acceptable salt thereof, of formula (Ib):

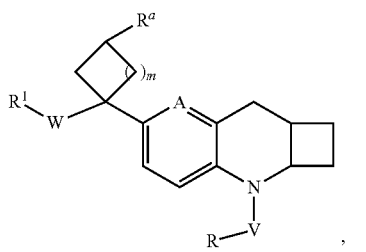

(Ib)

wherein:
m is 0 or 1;
A is selected from (1) —CH= and (2) —N=;
$R^a$ is selected from: (1) hydrogen and (2) $C_{1-4}$ alkyl;
$R^1$ is phenyl, optionally substituted with 1-3 hydrogens;
V is selected from (1) absent and (2) —C(O)—;
W is selected from (1) —C(O)—NH— and (2) —NH—C(O)—; and
R is selected from:
(1) hydrogen,
(2) $C_{1-4}$ alkyl, optionally substituted with 1-3 halogens,
(3) $C_{3-4}$ cycloalkyl,
(4) —O—$C_{1-4}$ alkyl, optionally substituted with phenyl,
(5) —O-cyclopropyl,
(6) —O-heterocyclyl, wherein the heterocyclyl is a 6-membered saturated monocyclic ring containing 1-2 hetero atoms independently selected from O, S, and N, and
(7) a heteroaryl selected from (a) pyridinyl and (b) pyrimidinyl,
wherein the heteroaryl of (7) is optionally substituted with 1-3 substituents independently selected from:
(a) halogen,
(b) —OH,
(c) $C_{1-4}$ alkyl, optionally substituted with 1-3 substituents independently selected from (i) —OH and (ii) halogen,
(d) —O—$C_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

13. The compound of claim 12, or a pharmaceutically acceptable salt thereof, wherein:
A is —CH=;
$R^a$ is hydrogen;
$R^1$ is phenyl, optionally substituted with a halogen; and
R is selected from:
(1) —O—$C_{1-4}$ alkyl,
(2) —O-cyclopropyl, and
(3) a heteroaryl selected from (a) pyridinyl and (b) pyrimidinyl, each of which is optionally substituted with a $C_{1-4}$ alkyl.

14. The compound of claim 1, or a pharmaceutically acceptable salt thereof, of formula (Ic):

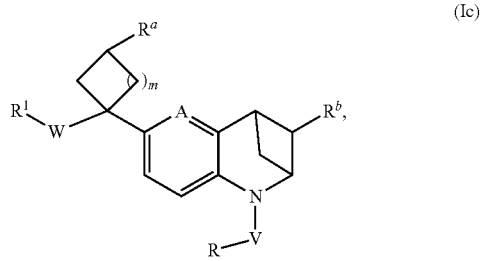

(Ic)

wherein:
m is 0 or 1;
A is selected from (1) —CH= and (2) —N=;
$R^a$ is selected from: (1) hydrogen and (2) $C_{1-4}$ alkyl;
$R^b$ is selected from: (1) hydrogen and (2) $C_{1-4}$ alkyl;
$R^1$ is phenyl, optionally substituted with 1-3 halogens;
V is selected from (1) absent and (2) —C(O)—;
W is selected from (1) —C(O)—NH— and (2) —NH—C(O)—; and
R is selected from:
(1) hydrogen,
(2) $C_{3-4}$ cycloalkyl,
(3) —O—$C_{1-4}$ alkyl, optionally substituted with phenyl,
(4) —O-cyclopropyl,
(5) —O-heterocyclyl, wherein the heterocyclyl is a 6-membered saturated monocyclic ring containing 1-2 hetero atoms independently selected from O, S, and N, and
(6) a heteroaryl selected from (a) pyridinyl and (b) pyrimidinyl,
wherein the heteroaryl of (6) is optionally substituted with 1-3 substituents independently selected from:
(a) halogen,
(b) —OH, (c) C$_{1-4}$ alkyl, optionally substituted with 1-3 substituents independently selected from (i) —OH and (ii) halogen,
(d) —O—C$_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

15. The compound of claim 14, or a pharmaceutically acceptable salt thereof, wherein:
m is 0;
A is —N=;
R$^a$ is hydrogen;
R$^b$ is selected from: (1) hydrogen and (2) methyl;
R$^1$ is phenyl, optionally substituted with a halogen; and
R is selected from:
(1) hydrogen,
(2) cyclopropyl,
(3) —O—C$_{1-4}$ alkyl, optionally substituted with phenyl,
(4) —O-cyclopropyl, and
(5) a heteroaryl selected from (a) pyridinyl and (b) pyrimidinyl,
wherein the heteroaryl of (5) is optionally substituted with 1-3 substituents independently selected from:
(a) halogen,
(b) —OH, and
(c) C$_{1-4}$ alkyl.

16. The compound of claim 1, or a pharmaceutically acceptable salt thereof, of formula (Id):

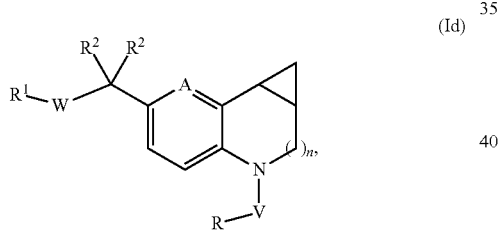

(Id)

wherein:
n is 0 or 1;
A is selected from (1) —CH= and (2) —N=;
R$^1$ is phenyl, optionally substituted with 1-3 halogens;
R$^2$ is selected from: (1) hydrogen and (2) C$_{1-4}$ alkyl;
V is selected from (1) absent and (2) —C(O)—;
W is selected from (1) —C(O)—NH— and (2) —NH—C(O)—; and
R is selected from:
(1) hydrogen,
(2) C$_{1-4}$ alkyl, optionally substituted with 1-3 halogens,
(3) C$_{3-4}$ cycloalkyl,
(4) —O—C$_{1-4}$ alkyl, optionally substituted with phenyl,
(5) —O-cyclopropyl,
(6) —O-heterocyclyl, wherein the heterocyclyl is a 6-membered saturated monocyclic ring containing 1-2 hetero atoms independently selected from O, S, and N, and
(7) a heteroaryl selected from (a) pyridinyl and (b) pyrimidinyl, wherein the heteroaryl of (7) is optionally substituted with 1-3 substituents independently selected from:
(a) halogen,
(b) —OH,
(c) C$_{1-4}$ alkyl, optionally substituted with 1-3 substituents independently selected from (i) —OH and (ii) halogen,
(d) —O—C$_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

17. The compound of claim 16, or a pharmaceutically acceptable salt thereof, wherein:
R$^1$ is phenyl, optionally substituted with a halogen;
R$^2$ is selected from: (1) hydrogen, (2) methyl, and (e) ethyl; and
R is selected from:
(1) hydrogen,
(2) C$_{1-4}$ alkyl, optionally substituted with 1-3 halogens,
(3) cyclopropyl,
(4) —O—C$_{1-4}$ alkyl, optionally substituted with phenyl,
(5) —O-cyclopropyl,
(6) —O-heterocyclyl, wherein the heterocyclyl is tetrahydropyranyl, and
(7) a heteroaryl selected from (a) pyridinyl and (b) pyrimidinyl,
wherein heteroaryl of (7) is optionally substituted with 1-3 substituents independently selected from:
(a) halogen,
(b) —OH,
(c) C$_{1-4}$ alkyl, optionally substituted with 1-3 substituents independently selected from (i) —OH and (ii) halogen,
(d) —O—C$_{1-4}$ alkyl, optionally substituted with 1-3 substituents independently selected from (i) —OH and (ii) halogen,
(e) cyclopropyl,
(f) —O-cyclopropyl, and
(g) —C(O)—O-methyl.

18. The compound of claim 1 selected from the group consisting of:
4-fluoro-N-(1-((1aR,7bS)-3-(2-methylpyrimidin-4-yl)-1a,2,3,7b-tetrahydro-1H-cyclopropa[c]quinolin-6-yl)cyclopropyl)benzamide,
1-(3-(cyclopropanecarbonyl)-1a,2,3,7b-tetrahydro-1H-cyclopropa[c]quinolin-6-yl)-N-(4-fluorophenyl)cyclobutanecarboxamide,
4-fluoro-N-(1-(3-(2-methylpyrimidin-4-yl)-1,2,2a,3,8,8a-hexahydrocyclobuta[b]quinolin-6-yl)cyclopropyl)benzamide,
methyl 6-(1-(4-fluorobenzamido)cyclopropyl)-1,2,2a,7b-tetrahydro-3H-cyclobuta[b]indole-3-carboxylate,
4-fluoro-N-(1-(2-(2-methylpyrimidin-4-yl)-1,1a,2,6b-tetrahydrocyclopropa[b]indol-5-yl)cyclopropyl)benzamide,
4-fluoro-N-(1-(5-(2-methylpyrimidin-4-yl)-6,6a,7,7a-tetrahydro-5H-cyclopropa[c][1,5]naphthyridin-2-yl)cyclopropyl)benzamide,
N-(1-(5-(2-ethylpyrimidin-4-yl)-6,6a,7,7a-tetrahydro-5H-cyclopropa[c][1,5]naphthyridin-2-yl)cyclopropyl)-4-fluorobenzamide,
N-(1-(5-(2-cyclopropylpyrimidin-4-yl)-6,6a,7,7a-tetrahydro-5H-cyclopropa[c][1,5]naphthyridin-2-yl)cyclopropyl)-4-fluorobenzamide, methyl 4-(2-(1-(4-fluorobenzamido)cyclopropyl)-6,6a,7,7a-tetrahydro-5H-cyclopropa[c][1,5]naphthyridin-5-yl)pyrimidine-2-carboxylate, 4-fluoro-N-(1-(5-(2-(2-hydroxypropan-2-yl)pyrimidin-4-yl)-6,6a,7,7a-tetrahydro-5H-cyclopropa[c][1,5]naphthyridin-2-yl)cyclopropyl)benzamide, 4-fluoro-N-(1-(5-(2-(hydroxymethyl)pyrimidin-4-yl)-6,6a,7,7a-tetrahydro-5H-cyclopropa[c][1,5]naphthyridin-2-yl)cyclopropyl)benzamide, (6aR, 7aS)-cyclopropyl 2-(1-(4-fluorobenzamido)cyclopropyl)-6,6a,7,7a-tetrahydro-5H-cyclopropa[c][1,5]naphthyridine-5-carboxylate, tetrahydro-2H-pyran-4-yl (6aR, 7aS)-2-(1-(4-fluorobenzamido)cyclopropyl)-6,6a,7,7a-tetrahydro-5H-cyclopropa[c][1,5]naphthyridine-5-carboxylate, tetrahydro-2H-pyran-4-yl (6aS,7aR)-2-(1-(4-fluorobenzamido)cyclopropyl)-6,6a, 7,7a-tetrahydro-5H-cyclopropa[c][1,5]naphthyridine-5-carboxylate, tert-butyl 2-(1-(4-fluorobenzamido)ethyl)-6,6a, 7,7a-tetrahydro-5H-cyclopropa[c][1,5]naphthyridine-5-carboxylate, cyclopropyl (6aR,7aS)-2-((S)-1-(4-fluorobenzamido)ethyl)-6,6a, 7,7a-tetrahydro-5H-cyclopropa[c][1,5]naphthyridine-5-carboxylate, cyclopropyl (6aS,7aR)-2-((S)-1-(4-fluorobenzamido)ethyl)-6,6a,7,7a-tetrahydro-5H-cyclopropa[c][1,5]naphthyridine-5-carboxylate, cyclopropyl (6aS,7aR)-2-((R)-1-(4-fluorobenzamido)ethyl)-6,6a,7,7a-tetrahydro-5H-cyclopropa[c][1,5]naphthyridine-5-carboxylate, cyclopropyl (6aR,7aS)-2-((R)-1-(4-fluorobenzamido)ethyl)-6,6a,7,7a-tetrahydro-5H-cyclopropa[c][1,5]naphthyridine-5-carboxylate, 4-fluoro-N-(2-(5-(2-methylpyrimidin-4-yl)-6,6a,7,7a-tetrahydro-5H-cyclopropa[c][1,5]naphthyridin-2-yl)propan-2-yl)benzamide, cyclopropyl 2-(2-(4-fluorobenzamido)propan-2-yl)-6,6a,7,7a-tetrahydro-5H-cyclopropa[c][1,5]naphthyridine-5-carboxylate, 2-(2-(4-fluorobenzamido)propan-2-yl)-5-(2,2,2-trifluoroacetyl)-6,6a, 7,7a-tetrahydro-5H-cyclopropa[c][1,5]naphthyridin-1-ium, cyclopropyl 2-(1-(4-fluorobenzamido)propyl)-6,6a,7,7a-tetrahydro-5H-cyclopropa[c][1,5]naphthyridine-5-carboxylate, 4-fluoro-N-(1-(5-(2-methylpyrimidin-4-yl)-6,6a,7,7a-tetrahydro-5H-cyclopropa[c][1,5]naphthyridin-2-yl)propyl)benzamide, (6aR,7aS) or(6aS,7aR)-tetrahydro-2H-pyran-4-yl 2-(1-(4-fluorobenzamido)cyclopropyl)-6,6a, 7,7a-tetrahydro-5H-cyclopropa[c][1,5]naphthyridine-5-carboxylate, (6aS,7aR) or(6aR,7aS)-tetrahydro-2H-pyran-4-yl 2-(1-(4-fluorobenzamido)cyclopropyl)-6,6a, 7,7a-tetrahydro-5H-cyclopropa[c][1,5]naphthyridine-5-carboxylate, 4-fluoro-N-(2-methyl-1-(5-(2-methylpyrimidin-4-yl)-6,6a,7,7a-tetrahydro-5H-cyclopropa[c][1,5]naphthyridin-2-yl)cyclopropyl)benzamide, 4-fluoro-N-(1-(3-methyl-1-(2-methylpyrimidin-4-yl)-1,2,3,4-tetrahydro-2,4-methano-1,5-naphthyridin-6-yl)cyclopropyl)benzamide, benzyl 6-(1-(4-fluorobenzamido)cyclopropyl)-3,4-dihydro-2,4-methano-1,5-naphthyridine-1(2H)-carboxylate, cyclopropyl 6-(1-(4-fluorobenzamido)cyclopropyl)-3,4-dihydro-2,4-methano-1,5-naphthyridine-1(2H)-carboxylate, 4-fluoro-N-(1-(1-(2-methylpyrimidin-4-yl)-1,2,3,4-tetrahydro-2,4-methano-1,5-naphthyridin-6-yl)cyclopropyl)benzamide, tert-butyl (6aR,7aS)-2-(1-(4-fluorobenzamido)cyclopropyl)-6,6a, 7,7a-tetrahydro-5H-cyclopropa[c][1,5]naphthyridine-5-carboxylate, tert-butyl (6aS,7aR)-2-(1-(4-fluorobenzamido)cyclopropyl)-6,6a,7,7a-tetrahydro-5H-cyclopropa[c][1,5]naphthyridine-5-carboxylate, 4-fluoro-N-(2-(6,6a, 7,7a-tetrahydro-5H-cyclopropa[c][1,5]naphthyridin-2-yl)propan-2-yl)benzamide, and tert-butyl 2-(2-(4-fluorobenzamido)propan-2-yl)-6,6a, 7,7a-tetrahydro-5H-cyclopropa[c][1,5]naphthyridine-5-carboxylate;

or a pharmaceutically acceptable salt thereof.

19. A composition which comprises an inert carrier and a compound of claim 1, or a pharmaceutically acceptable salt thereof.

* * * * *